(12) United States Patent
Schlemminger et al.

(10) Patent No.: US 8,609,848 B2
(45) Date of Patent: Dec. 17, 2013

(54) PYRAZOLONE-DERIVATIVES AND THEIR USE AS PDE-4 INHIBITORS

(75) Inventors: Imre Schlemminger, Constance (DE);
Beate Schmidt, Allensbach (DE); Dieter Flockerzi, Allensbach (DE); Hermann Tenor, Radolfzell (DE); Christof Zitt, Constance (DE); Armin Hatzelmann, Constance (DE); Degenhard Marx, Moos (DE); Clemens Braun, Constance (DE); Raimund Külzer, Constance (DE); Anke Heuser, Hamburg (DE); Hans-Peter Kley, Allensbach (DE); Geert Jan Sterk, Utrecht (NL)

(73) Assignee: Takeda GmbH, Constance (DE)

( * ) Notice: Subject to any disclaimer, the term of this patent is extended or adjusted under 35 U.S.C. 154(b) by 412 days.

(21) Appl. No.: 13/128,051

(22) PCT Filed: Nov. 12, 2009

(86) PCT No.: PCT/EP2009/065031
§ 371 (c)(1),
(2), (4) Date: May 6, 2011

(87) PCT Pub. No.: WO2010/055083
PCT Pub. Date: May 20, 2010

(65) Prior Publication Data
US 2011/0218201 A1    Sep. 8, 2011

Related U.S. Application Data

(60) Provisional application No. 61/193,333, filed on Nov. 19, 2008.

(30) Foreign Application Priority Data

Nov. 14, 2008 (EP) .................... 08169143

(51) Int. Cl.
*C07D 401/00* (2006.01)
*A61K 31/445* (2006.01)

(52) U.S. Cl.
USPC .......................... 546/211; 514/326

(58) Field of Classification Search
USPC .......................... 546/211; 514/326
See application file for complete search history.

(56) References Cited

U.S. PATENT DOCUMENTS

| | | | |
|---|---|---|---|
| 2,903,460 | A | 9/1959 | Jucker et al. |
| 6,103,718 | A | 8/2000 | Sterk |
| 6,953,853 | B2 | 10/2005 | Grundler et al. |
| 7,179,810 | B2 | 2/2007 | Grundler et al. |
| 7,186,710 | B2 | 3/2007 | Sterk |
| 7,220,746 | B2 | 5/2007 | Sterk |
| 7,494,990 | B2 | 2/2009 | Menge et al. |
| 7,531,540 | B2 | 5/2009 | Grundler et al. |
| 7,632,838 | B2 | 12/2009 | Xiang et al. |
| 7,820,669 | B2 | 10/2010 | Menge et al. |
| 2006/0094710 | A1 | 5/2006 | Sterk |
| 2006/0167001 | A1 | 7/2006 | Sterk |
| 2010/0029648 | A1 | 2/2010 | Xiang et al. |
| 2010/0120757 | A1 | 5/2010 | Schmidt et al. |
| 2010/0130738 | A1 | 5/2010 | Kohno et al. |

FOREIGN PATENT DOCUMENTS

| | | |
|---|---|---|
| EP | 0 126 651 A2 | 11/1984 |
| WO | 98/31674 A1 | 7/1998 |
| WO | 02/064584 A1 | 8/2002 |
| WO | 02/085906 A2 | 10/2002 |
| WO | 2004/017974 A1 | 3/2004 |
| WO | 2004/018449 A1 | 3/2004 |
| WO | 2004/018451 A1 | 3/2004 |
| WO | 2004/018457 A1 | 3/2004 |
| WO | 2005/075456 A1 | 8/2005 |
| WO | 2005/075457 A1 | 8/2005 |
| WO | 2007/092435 A2 | 8/2007 |
| WO | 2008/138939 A1 | 11/2008 |
| WO | 2008/156102 A1 | 12/2008 |

*Primary Examiner* — John Mabry
(74) *Attorney, Agent, or Firm* — Nath, Goldberg & Meyer; Sheldon M. McGee

(57) ABSTRACT

The compounds of Formula (I),

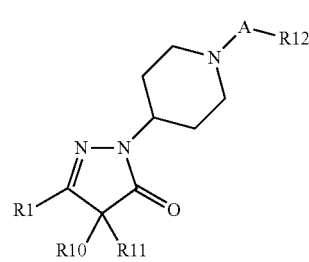

are novel effective inhibitors of the type 4 phosphodiesterase.

15 Claims, No Drawings

PYRAZOLONE-DERIVATIVES AND THEIR USE AS PDE-4 INHIBITORS

This application is filed under 35 U.S.C. 371 as the national stage of PCT/EP2009/065031, filed Nov. 12, 2009, which claims priority to EP 08169143.8, filed Nov. 14, 2008 and also claims priority to U.S. 61/193,333, filed Nov. 19, 2008.

FIELD OF APPLICATION OF THE INVENTION

The invention relates to novel pyrazolone compounds, which are used in the pharmaceutical industry for the manufacture of pharmaceutical compositions.

KNOWN TECHNICAL BACKGROUND

In the International patent application WO98/31674 phthalazinone compounds are described as PDE4 inhibitors. In the International patent applications WO02/064584, WO02/085906, WO2004/017974, WO2004/018449, WO2004/018451, WO2004/018457, WO2005/075456 and WO2005/075457 phthalazinone- or pyridazinone-compounds with a piperidinyl substituent are described as PDE4 inhibitors. In the European patent application EP0126651 2,4-dihydro-5-[(substituted) phenyl]-4,4-disubstituted-3H-pyrazol-3-ones and 2,4-dihydro-5-[(substituted) phenyl]-4,4-disubstituted-3H-pyrazol-3-thiones are disclosed for use as cardiotonic and antihypertensive agents. In U.S. Pat. No. 2,903,460 pyrazolone compounds with a piperidinyl substituent are described as analgetic and antipyretic compounds. In the International patent application WO2008138939 pyrazolone compounds with a piperidinyl substituent are described as PDE4 inhibitors. In the International patent application WO2008156102 compounds having a pyrazolone core structure attached to a fused heterocyclic ring system are described as PDE3/4 inhibitors.

DESCRIPTION OF THE INVENTION

It has now been found that the pyrazolone compounds, which are described in greater details below, have surprising and particularly advantageous properties.

The invention relates to a compound of formula 1

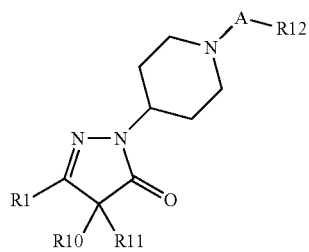

(1)

wherein
R1 represents a phenyl derivative of formulae (a), (b) or (c)

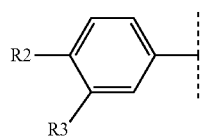

(a)

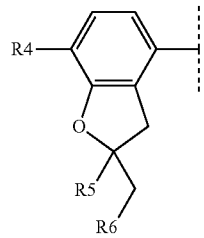

(b)

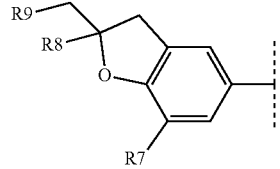

(c)

wherein
R2 is 1-2C-alkoxy or 1-2C-alkoxy which is completely or predominantly substituted by fluorine,
R3 is 1-2C-alkoxy, 3-5C-cycloalkoxy, 3-5C-cycloalkylmethoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O) or S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy,
R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino, R15 is hydrogen, halogen or 1-4C-alkyl,
R16 is hydrogen or 1-4C-alkyl,
R17 is halogen, 1-4C-alkyl, trifluoromethyl, 1-4C-alkoxy, amino, mono- or di-1-4C-alkylamino, piperidinyl or morpholinyl,
R18 is hydrogen, halogen, 1-4C-alkyl or 1-4C-alkoxy,
R19 is halogen, hydroxy, 1-4C-alkyl, 1-4C-alkoxy, amino or mono- or di-1-4C-alkylamino,
R20 is hydrogen, 1-4C-alkyl or 1-4C-alkoxy,
R21 is 1-4C-alkyl,
R22 is 1-4C-alkyl,
or a salt, a stereoisomer or a salt of a stereoisomer of the compound.

1-4C-Alkyl is a straight-chain or branched alkyl group having 1 to 4 carbon atoms. Examples are butyl, isobutyl, sec-butyl, tert-butyl, propyl, isopropyl, ethyl and methyl.

1-3C-Alkyl is a straight-chain or branched alkyl group having 1 to 3 carbon atoms. Examples are propyl, isopropyl, ethyl and methyl.

1-2C-Alkyl is a straight-chain alkyl group having 1 to 2 carbon atoms. Examples are ethyl and methyl.

1-4C-Alkoxy is a group which, in addition to the oxygen atom, contains a straight-chain or branched alkyl group having 1 to 4 carbon atoms. Alkoxy groups having 1 to 4 carbon atoms which may be mentioned in this context are, for example, butoxy, isobutoxy, sec-butoxy, tert-butoxy, propoxy, isopropoxy, ethoxy and methoxy.

1-2C-Alkoxy is a group, which in addition to the oxygen atom, contains a straight-chain alkyl group having 1 to 2 carbon atoms. Examples are ethoxy and methoxy.

1-4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy group are replaced by fluorine atoms.

1-2C-Alkoxy which is completely or predominantly substituted by fluorine is, for example, the perfluoroethoxy, the 1,2,2-trifluoroethoxy, the 1,1,2,2-tetrafluoroethoxy, the 2,2,2-trifluoroethoxy, the trifluoromethoxy and the difluoromethoxy radical, of which the difluoromethoxy radical is preferred.

"Predominantly" in this connection means that more than half of the hydrogen atoms of the 1-2C-alkoxy group are replaced by fluorine atoms.

An 1-4C-Alkylcarbonylamino group is, for example, the propionylamino [$C_3H_7C(O)NH-$] and the acetylamino group [$CH_3C(O)NH-$].

1-4C-Alkylcarbonyl is a carbonyl group to which one of the abovementioned 1-4C-alkyl groups is bonded. An example is the acetyl group [$CH_3C(O)-$].

1-4C-Alkylcarbonyloxy groups contain, in addition to the oxygen atom, one of the above-mentioned 1-4C-alkylcarbonyl groups. An example is the acetoxy group [$CH_3C(O)-O-$].

1-4C-Alkoxycarbonyl is a carbonyl group to which one of the abovementioned 1-4C-alkoxy groups is bonded. Examples are the methoxycarbonyl [$CH_3O-C(O)-$] and the ethoxycarbonyl [$CH_3CH_2O-C(O)-$] group.

1-4C-Alkoxycarbonyl-1-4C-alkoxy is a 1-4C-alkoxy group to which one of the above-mentioned 1-4C-alkoxycarbonyl groups is bonded. Examples are the ethoxycarbonylmethoxy [$CH_3-CH_2-O-C(O)-CH_2-O-$] and the methoxycarbonylmethoxy [$CH_3O-C(O)-CH_2-O-$] group.

Aminocarbonyl-1-4C-alkoxy is a 1-4C-alkoxy group to which an aminocarbonyl group is bonded. An example is aminocarbonylmethoxy [$H_2N-C(O)-CH_2-O-$].

Mono- or di-1-4C-alkylamino radicals contain in addition to the nitrogen atom, one or two of the above-mentioned 1-4C-alkyl radicals. Preferred are the di-1-4C-alkylamino radicals, especially the dimethylamino, the diethylamino and the diisopropylamino radical.

Mono- or di-1-4C-alkylaminocarbonyl is a carbonyl group to which one of the above-mentioned mono- or -di-1-4C-alkylamino groups is bonded. Examples are the methylaminocarbonyl group and the dimethylaminocarbonyl group.

3-7C-Cycloalkoxy stands for cyclopropyloxy, cyclobutyloxy, cyclopentyloxy, cyclohexyloxy or cycloheptyloxy.

3-5C-Cycloalkoxy stands for cyclopropyloxy, cyclobutyloxy or cyclopentyloxy.

3-7C-Cycloalkylmethoxy stands for cyclopropylmethoxy, cyclobutylmethoxy, cyclopentylmethoxy, cyclohexylmethoxy or cycloheptylmethoxy.

3-5C-Cycloalkylmethoxy stands for cyclopropylmethoxy, cyclobutylmethoxy or cyclopentylmethoxy.

Halogen includes fluorine, chlorine, bromine and iodine, with fluorine, chlorine and bromine being preferred.

As spiro-linked 5- or 6-membered hydrocarbon rings may be mentioned the cyclopentane and the cyclohexane ring.

As spiro-linked 3-, 4-, 5- or 6-membered hydrocarbon rings may be mentioned the cyclopropane, the cyclobutane, the cyclopentane and the cyclohexane ring.

Exemplary phenyl radicals substituted by R13, R14, R15 and R16, which may be mentioned are 2-cyanophenyl, 2-fluorophenyl, 3-fluorophenyl, 2-bromophenyl, 4-bromophenyl, 2-chlorophenyl, 3-chlorophenyl, 4-chlorophenyl, 3-chloro-4-fluorophenyl, 2,3-dichlorophenyl, 2,4-dichlorophenyl, 2,5-dichlorophenyl, 3,5-dichlorophenyl, 2,6-dichlorophenyl, 2,3-difluorophenyl, 2,6-difluorophenyl, 2,4,6-trichlorophenyl, 2-methylphenyl, 3-methylphenyl, 4-methylphenyl, 2-ethylphenyl, 4-isopropylphenyl, 4-tert-butylphenyl, 2-trifluoromethylphenyl, 3-trifluoromethylphenyl, 2,5-dimethylphenyl, 2,3,5,6-tetramethylphenyl, 2,4,6-triisopropylphenyl, 2-methyl-4-fluorophenyl, 2-hydroxyphenyl, 3-hydroxyphenyl, 2-methoxyphenyl, 3-methoxyphenyl, 4-methoxyphenyl, 3-ethoxyphenyl, 3-isopropoxyphenyl, 2-trifluoromethoxyphenyl, 2,5-dimethoxyphenyl, 2,4-dimethoxyphenyl, 2,6-dimethoxyphenyl, 3-(2,2,2-trifluoroethoxy)phenyl, 4-(difluoromethoxy)phenyl, 2-methoxy-5-chlorophenyl, 5-isopropoxy-2-methylphenyl, 2-cyclopentyloxyphenyl, 5-tert-butoxy-2-methylphenyl, 5-difluoromethoxy-2-methylphenyl, 5-trifluoromethoxy-2-methylphenyl, 5-cyclopropylmethoxy-2-methylphenyl, 3-cyclopropylmethoxy-4-difluoromethoxyphenyl, 2-fluoro-5-hydroxyphenyl, 2-chloro-5-hydroxyphenyl, 2-chloro-4-trifluoromethylphenyl, 5-benzyloxy-2-chlorophenyl, 2-chloro-5-ethoxyphenyl, 2-chloro-5-isopropoxyphenyl, 2-chloro-5-(methylcarbonylamino)phenyl, 2-chloro-5-(ethoxycarbonylmethoxy)phenyl, 2-methyl-5-(ethoxycarbonylmethoxy)phenyl, 4-hydroxy-2-methylphenyl, 5-hydroxy-2-methylphenyl, 3-aminophenyl, 3-dimethylaminophenyl, 4-amino-3-trifluoromethylphenyl, 5-amino-2-chlorophenyl, 2-(aminocarbonylmethoxy)phenyl, 5-benzyloxy-2-methylphenyl, 5-[(2,6-dichlorobenzyl)oxy]-2-methylphenyl, 2-(methylcarbonyloxy)phenyl, 3-(methylcarbonyloxy)phenyl, 4-(methylcarbonyloxy)phenyl, 3-methylcarbonylaminophenyl, 2-(hydroxycarbonyl)phenyl, 3-(hydroxycarbonyl)

phenyl, 2-(methoxycarbonyl)phenyl, 3-(methoxycarbonyl)phenyl and 3,5-bis-(methoxycarbonyl)phenyl.

Exemplary pyridinyl radicals substituted by R17 and R18, which may be mentioned are 3-methylpyridin-2-yl, 4-(trifluoromethyl)pyridin-3-yl, 2-methoxypyridin-3-yl, 3-chloropyridin-4-yl, 3,5-difluoropyridin-2-yl, 2,6-dimethoxypyridin-3-yl, 2-(piperidin-1-yl)pyridin-4-yl and 2-(morpholin-4-yl)pyridin-4-yl.

Exemplary naphthalenyl radicals substituted by R19 and R20, which may be mentioned are 1-bromonaphthalen-2-yl, 8-bromo-naphthalen-1-yl, 1-methoxynaphthalen-2-yl, 2-methoxynaphthalen-1-yl, 2-methylnaphthalen-1-yl, 3-methoxynaphthalen-2-yl, 6-hydroxy-naphthalen-1-yl, 4-dimethylamino-naphthalen-1-yl and 4,7-dimethoxy-naphthalen-2-yl.

An exemplary quinolinyl radical substituted by R21, which may be mentioned is 4-methyl-quinolin-2-yl.

Exemplary indolyl radicals substituted by R22, which may be mentioned are 1-methyl-1H-indol-4-yl and 1-methyl-1H-indol-5-yl.

It is to be understood that the pyridinyl, quinolinyl, isoquinolinyl, quinoxalinyl, 1,6-naphthyridinyl, 1,8-naphthyridinyl or indolyl radical is bonded to the carbonyl or sulfonyl group via a ring carbon atom. Therefore pyridinyl refers, unless otherwise noted, to pyridin-2-yl, pyridin-3-yl or pyridin-4-yl. Quinolinyl refers, unless otherwise noted, to quinolin-2-yl, quinolin-3-yl, quinolin-4-yl, quinolin-5-yl, quinolin-6-yl, quinolin-7-yl or quinolin-8-yl. Isoquinoline refers, unless otherwise noted, to isoquinolin-1-yl, isoquinolin-3-yl, isoquinolin-4-yl, isoquinolin-5-yl, isoquinolin-6-yl, isoquinolin-7-yl or isoquinolin-8-yl. Quinoxalinyl refers, unless otherwise noted, to quinoxalin-2-yl, quinoxalin-5-yl or quinoxalin-6-yl. 1,6-Naphthyridinyl refers, unless otherwise noted, to 1,6-naphthyridin-2-yl, 1,6-naphthyridin-3-yl, 1,6-naphthyridin-4-yl, 1,6-naphthyridin-5-yl, 1,6-naphthyridin-7-yl or 1,6-naphthyridin-8-yl. 1,8-naphthyridinyl refers, unless otherwise noted, to 1,8-naphthyridin-2-yl, 1,8-naphthyridin-3-yl or 1,8-naphthyridin-4-yl. Indolyl refers, unless otherwise noted, to indol-2-yl, indol-3-yl, indol-4-yl, indol-5-yl, indol-6-yl or indol-7-yl.

In a preferred embodiment, the invention relates to a compound of formula 1, wherein R1 represents a phenyl derivative of formulae (a), (b) or (c)

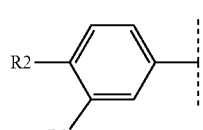

(a)

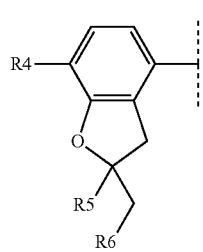

(b)

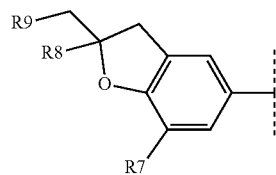

(c)

wherein
R2 is 1-2C-alkoxy or 1-2C-alkoxy which is completely or predominantly substituted by fluorine,
R3 is 1-2C-alkoxy, 3-5C-cycloalkoxy, 3-5C-cycloalkylmethoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O) or S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16 or pyridinyl substituted by R17 and R18,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, amino, mono- or di-1-4C-alkylamino, piperidinyl or morpholinyl,
R18 is hydrogen, halogen, 1-4C-alkyl or 1-4C-alkoxy,
or a salt, a stereoisomer or a salt of a stereoisomer of the compound.

In another preferred embodiment, the invention relates to a compound of formula 1, wherein
R1 represents a phenyl derivative of formulae (a), (b) or (c)

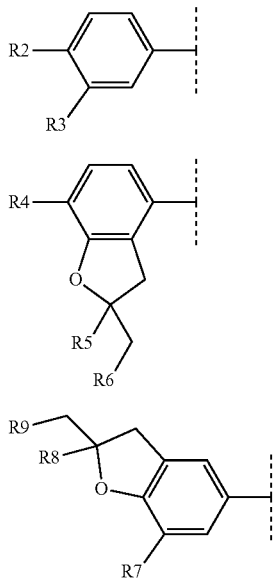

R2 is 1-2C-alkoxy or 1-2C-alkoxy which is completely or predominantly substituted by fluorine,
R3 is 1-2C-alkoxy, 3-5C-cycloalkoxy, 3-5C-cycloalkyl-methoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O),
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, amino, mono- or di-1-4C-alkylamino, piperidinyl or morpholinyl,
R18 is hydrogen, halogen, 1-4C-alkyl or 1-4C-alkoxy,
R19 is halogen, hydroxy, 1-4C-alkyl, 1-4C-alkoxy, amino or mono- or di-1-4C-alkylamino,
R20 is hydrogen, 1-4C-alkyl or 1-4C-alkoxy,
R21 is 1-4C-alkyl,
R22 is 1-4C-alkyl,
or a salt, a stereoisomer or a salt of a stereoisomer of the compound.

In another preferred embodiment, the invention relates to a compound of formula 1, wherein
R1 represents a phenyl derivative of formulae (a), (b) or (c)

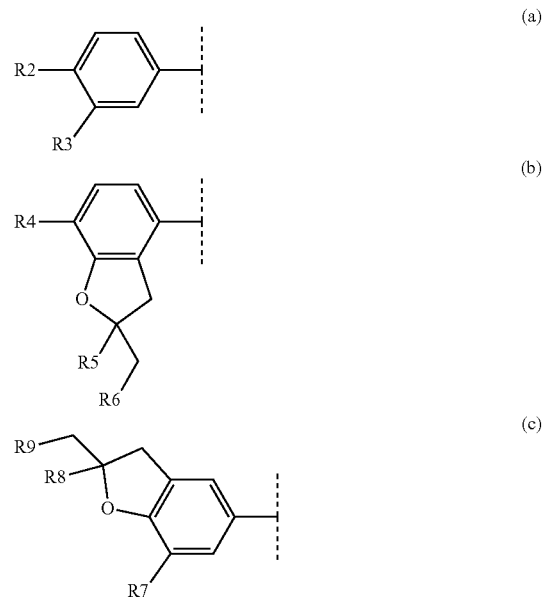

R2 is 1-2C-alkoxy or 1-2C-alkoxy which is completely or predominantly substituted by fluorine,
R3 is 1-2C-alkoxy, 3-5C-cycloalkoxy, 3-5C-cycloalkyl-methoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring, R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O),
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16 or pyridinyl substituted by R17 and R18,
wherein
   R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
   R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
   R15 is hydrogen, halogen or 1-4C-alkyl,
   R16 is hydrogen or 1-4C-alkyl,
   R17 is halogen, 1-4C-alkyl, trifluoromethyl, 1-4C-alkoxy, amino, mono- or di-1-4C-alkylamino, piperidinyl or morpholinyl,
   R18 is hydrogen, halogen, 1-4C-alkyl or 1-4C-alkoxy,
or a salt, a stereoisomer or a salt of a stereoisomer of the compound.

In another preferred embodiment, the invention relates to a compound of formula 1, wherein
R1 represents a phenyl derivative of formulae (a), (b) or (c)

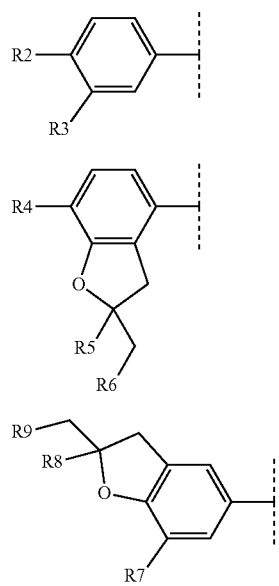

wherein
   R2 is 1-2C-alkoxy or 1-2C-alkoxy which is completely or predominantly substituted by fluorine,
   R3 is 1-2C-alkoxy, 3-5C-cycloalkoxy, 3-5C-cycloalkylmethoxy or 1-2C-alkoxy which is completely or predominantly substituted by fluorine,
   R4 is 1-2C-alkoxy or 1-2C-alkoxy which is completely or predominantly substituted by fluorine;
   R5 is 1-2C-alkyl and
   R6 is hydrogen or 1-2C-alkyl,
   or R5 and R6 together and with inclusion of the two carbon atoms, to which they are bonded, form a spiro-linked 5- or 6-membered hydrocarbon ring,
   R7 is 1-2C-alkoxy or 1-2C-alkoxy which is completely or predominantly substituted by fluorine,
   R8 is 1-2C-alkyl and
   R9 is hydrogen or 1-2C-alkyl,
   or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
   R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
   R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
   R15 is hydrogen, halogen or 1-4C-alkyl,
   R16 is hydrogen or 1-4C-alkyl,
   R17 is halogen, 1-4C-alkyl, trifluoromethyl, 1-4C-alkoxy, amino, mono- or di-1-4C-alkylamino, piperidinyl or morpholinyl,
   R18 is hydrogen, halogen, 1-4C-alkyl or 1-4C-alkoxy,
   R19 is halogen, hydroxy, 1-4C-alkyl, 1-4C-alkoxy, amino or mono- or di-1-4C-alkylamino,
   R20 is hydrogen, 1-4C-alkyl or 1-4C-alkoxy,
   R21 is 1-4C-alkyl,
   R22 is 1-4C-alkyl,
or a salt, a stereoisomer or a salt of a stereoisomer of the compound.

In another preferred embodiment, the invention relates to a compound of formula 1, wherein
R1 represents a phenyl derivative of formulae (a), (b) or (c)

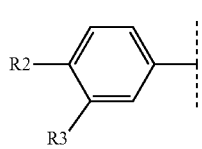

-continued

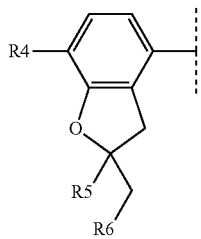
(b)

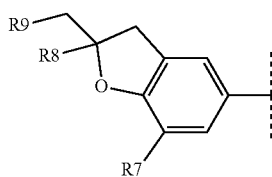
(c)

wherein
- R2 is 1-2C-alkoxy or 1-2C-alkoxy which is completely or predominantly substituted by fluorine,
- R3 is 1-2C-alkoxy, 3-5C-cycloalkoxy, 3-5C-cycloalkylmethoxy or 1-2C-alkoxy which is completely or predominantly substituted by fluorine,
- R4 is 1-2C-alkoxy or 1-2C-alkoxy which is completely or predominantly substituted by fluorine;
- R5 is 1-2C-alkyl and
- R6 is hydrogen or 1-2C-alkyl,
- or R5 and R6 together and with inclusion of the two carbon atoms, to which they are bonded, form a spiro-linked 5- or 6-membered hydrocarbon ring,
- R7 is 1-2C-alkoxy or 1-2C-alkoxy which is completely or predominantly substituted by fluorine,
- R8 is 1-2C-alkyl and
- R9 is hydrogen or 1-2C-alkyl,
- or R8 and R9 together and with inclusion of the two carbon atoms, to which they are bonded, form a spiro-linked 5- or 6-membered hydrocarbon ring,
- R10 is 1-3C-alkyl and
- R11 is 1-3C-alkyl,
- or R10 and R11 together with the carbon atom, to which they are bonded, form a spiro-linked 3-, 4-, 5- or 6-membered hydrocarbon ring,
- A is S(O)$_2$,
- R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16 or pyridinyl substituted by R17 and R18,
wherein
- R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
- R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
- R15 is hydrogen, halogen or 1-4C-alkyl,
- R16 is hydrogen or 1-4C-alkyl,
- R17 is halogen, 1-4C-alkyl, trifluoromethyl, 1-4C-alkoxy, amino, mono- or di-1-4C-alkylamino, piperidinyl or morpholinyl,
- R18 is hydrogen, halogen, 1-4C-alkyl or 1-4C-alkoxy,
or a salt, a stereoisomer or a salt of a stereoisomer of the compound.

In another preferred embodiment, the invention relates to a compound of formula 1, wherein R1 represents a phenyl derivative of formulae (a), (b) or (c)

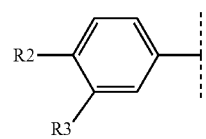
(a)

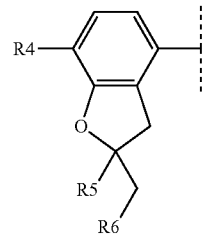
(b)

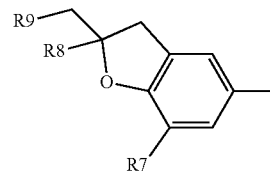
(c)

wherein
- R2 is 1-2C-alkoxy or 1-2C-alkoxy which is completely or predominantly substituted by fluorine,
- R3 is 1-2C-alkoxy or 3-5C-cycloalkylmethoxy,
- R4 is 1-2C-alkoxy,
- R5 is 1-2C-alkyl and
- R6 is hydrogen or 1-2C-alkyl,
- or R5 and R6 together and with inclusion of the two carbon atoms, to which they are bonded, form a spiro-linked 5- or 6-membered hydrocarbon ring,
- R7 is 1-2C-alkoxy,
- R8 is 1-2C-alkyl and
- R9 is hydrogen or 1-2C-alkyl,
- or R8 and R9 together and with inclusion of the two carbon atoms, to which they are bonded, form a spiro-linked 5- or 6-membered hydrocarbon ring,
- R10 is 1-2C-alkyl and
- R11 is 1-3C-alkyl,
- or R10 and R11 together with the carbon atom, to which they are bonded, form a spiro-linked 5- or 6-membered hydrocarbon ring,
- A is C(O),
- R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
- R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy, R14 is hydrogen, halogen, amino, 1-4C-alkyl, 1-4C-alkoxy, 1-4C-alkoxy which is completely or predominantly substituted by fluorine, or 1-4C-alkoxycarbonyl, R15 is hydrogen, halogen or 1-4C-alkyl, R16 is hydrogen or 1-4C-alkyl, R17 is halogen, 1-4C-alkyl, trifluoromethyl, 1-4C-alkoxy, di-1-2C-alkylamino, piperidinyl or morpholinyl, R18 is hydrogen, halogen, 1-4C-alkyl or 1-4C-alkoxy, R19 is halogen, 1-4C-alkyl, 1-4C-alkoxy or di-1-2C-alkylamino, R20 is hydrogen, 1-4C-alkyl or 1-4C-alkoxy, R21 is 1-4C-alkyl, R22 is 1-4C-alkyl, or a salt, a stereoisomer or a salt of a stereoisomer of the compound.

In another preferred embodiment, the invention relates to a compound of formula 1, wherein R1 represents a phenyl derivative of formulae (a), (b) or (c)

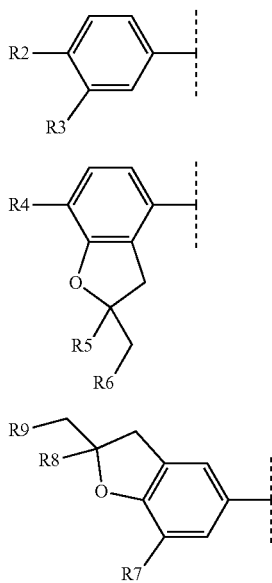

wherein
R2 is 1-2C-alkoxy,
R3 is 1-2C-alkoxy or 3-5C-cycloalkylmethoxy,
R4 is 1-2C-alkoxy,
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-2C-alkyl and
R11 is 1-2C-alkyl,
or R10 and R11 together with the carbon atom, to which they are bonded, form a spiro-linked 5- or 6-membered hydrocarbon ring, A is C(O), R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16 or pyridinyl substituted by R17 and R18, wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy, R14 is hydrogen, halogen, amino, 1-4C-alkyl, 1-4C-alkoxy, 1-4C-alkoxy which is completely or predominantly substituted by fluorine, or 1-4C-alkoxycarbonyl, R15 is hydrogen, halogen or 1-4C-alkyl, R16 is hydrogen or 1-4C-alkyl, R17 is halogen, 1-4C-alkyl, trifluoromethyl, 1-4C-alkoxy, di-1-2C-alkylamino, piperidinyl or morpholinyl, R18 is hydrogen, halogen, 1-4C-alkyl or 1-4C-alkoxy, or a salt, a stereoisomer or a salt of a stereoisomer of the compound.

In another preferred embodiment, the invention relates to a compound of formula 1, wherein
R1 represents a phenyl derivative of formulae (a), (b) or (c)

wherein
R2 is 1-2C-alkoxy or 1-2C-alkoxy which is completely or predominantly substituted by fluorine,
R3 is 1-2C-alkoxy or 3-5C-cycloalkylmethoxy,
R4 is 1-2C-alkoxy,
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring, R7 is 1-2C-alkoxy,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-2C-alkyl and
R11 is 1-3C-alkyl,
or R10 and R11 together with the carbon atom, to which they are bonded, form a spiro-linked 5- or 6-membered hydrocarbon ring,
A is S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy,
R14 is hydrogen, halogen, amino, 1-4C-alkyl, 1-4C-alkoxy, 1-4C-alkoxy which is completely or predominantly substituted by fluorine, or 1-4C-alkoxycarbonyl,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, di-1-2C-alkylamino, piperidinyl or morpholinyl,
R18 is hydrogen, halogen, 1-4C-alkyl or 1-4C-alkoxy,
R19 is halogen, 1-4C-alkyl, 1-4C-alkoxy or di-1-2C-alkylamino,
R20 is hydrogen, 1-4C-alkyl or 1-4C-alkoxy,
R21 is 1-4C-alkyl,
R22 is 1-4C-alkyl,
or a salt, a stereoisomer or a salt of a stereoisomer of the compound.

In another preferred embodiment, the invention relates to a compound of formula 1, wherein
R1 represents a phenyl derivative of formulae (a), (b) or (c)

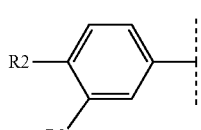

(a)

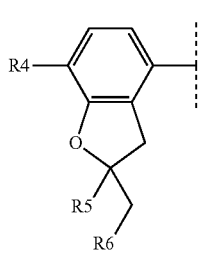

(b)

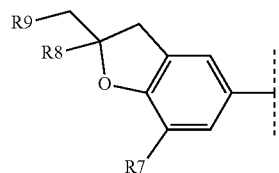

(c)

wherein
R2 is 1-2C-alkoxy;
R3 is 1-2C-alkoxy or 3-5C-cycloalkylmethoxy,
R4 is 1-2C-alkoxy;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-2C-alkyl and
R11 is 1-2C-alkyl,
or R10 and R11 together with the carbon atom, to which they are bonded, form a spiro-linked 5- or 6-membered hydrocarbon ring,
A is S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl which is substituted by R13, R14, R15 and R16 or pyridinyl which is substituted by R17 and R18,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy,
R14 is hydrogen, halogen, amino, 1-4C-alkyl, 1-4C-alkoxy, 1-4C-alkoxy which is completely or predominantly substituted by fluorine, or 1-4C-alkoxycarbonyl,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, di-1-2C-alkylamino, piperidinyl or morpholinyl,
R18 is hydrogen, halogen, 1-4C-alkyl or 1-4C-alkoxy,
or a salt, a stereoisomer or a salt of a stereoisomer of the compound.

In another preferred embodiment, the invention relates to a compound of formula 1, wherein
R1 represents a phenyl derivative of formulae (a), (b) or (c)

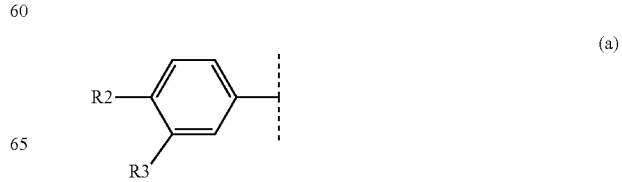

(a)

-continued

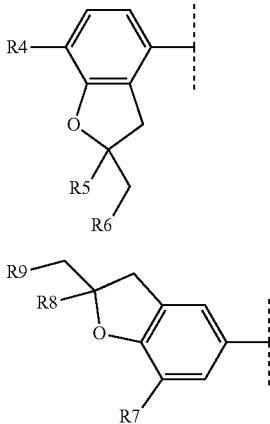
(b)

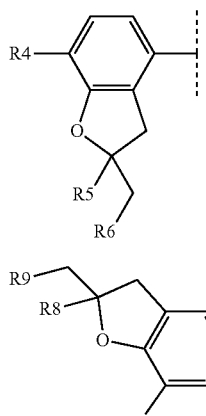

wherein
- R2 is methoxy, ethoxy or difluoromethoxy,
- R3 is methoxy, ethoxy or cyclopropylmethoxy,
- R4 is methoxy,
- R5 is methyl,
- R6 is hydrogen,
- or R5 and R6 together and with inclusion of the two carbon atoms, to which they are bonded, form a spiro-linked cyclopentane ring,
- R7 is methoxy
- R8 is methyl,
- R9 is hydrogen,
- R10 is methyl or ethyl,
- R11 is methyl, ethyl or propyl,
- or R10 and R11 together with the carbon atom, to which they are bonded, form a spiro-linked cyclopentane ring,
- A is C(O),
- R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20 or quinolinyl substituted by R21, wherein
- R13 is fluorine, chlorine, bromine, hydroxy, 1-2C-alkyl, trifluoromethyl, 1-4C-alkoxy, 1-4C-alkoxy which is completely or predominantly substituted by fluorine, cyclopentyloxy, cyclopropylmethoxy, benzyloxy, 2,6-dichlorobenzyloxy, amino, di-1-2C-alkylamino, aminocarbonylmethoxy, 1-2C-alkylcarbonylamino, 1-2C-alkylcarbonyloxy, 1-2C-alkoxycarbonyl or 1-2C-alkoxycarbonylmethoxy,
- R14 is hydrogen, fluorine, chlorine, amino, 1-2C-alkyl, 1-2C-alkoxy or 1-2C-alkoxy which is completely or predominantly substituted by fluorine,
- R15 is hydrogen, chlorine or 1-2C-alkyl,
- R16 is hydrogen or 1-2C-alkyl,
- R17 is fluorine, chlorine, 1-2C-alkyl, trifluoromethyl, 1-2C-alkoxy, di-1-2C-alkylamino, piperidinyl or morpholinyl,
- R18 is hydrogen, fluorine, 1-2C-alkyl or 1-2C-alkoxy,
- R19 is bromine, 1-2C-alkyl, 1-2C-alkoxy, di-1-2C-alkylamino,
- R20 is hydrogen, 1-2C-alkyl or 1-2C-alkoxy,
- R21 is 1-2C-alkyl, or a salt, a stereoisomer or a salt of a stereoisomer of the compound.

In a further preferred embodiment, the invention relates to a compound of formula 1, wherein R1 represents a phenyl derivative of formulae (a), (b) or (c)

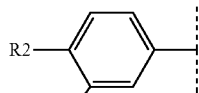
(a)

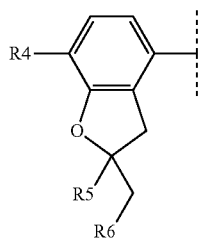
(b)

(c)

wherein
- R2 is methoxy,
- R3 is methoxy or cyclopropylmethoxy,
- R4 is methoxy,
- R5 is methyl,
- R6 is hydrogen,
- R7 is methoxy
- R8 is methyl,
- R9 is hydrogen,
- R10 is methyl,
- R11 is methyl,
- A is C(O),
- R12 phenyl, naphthalenyl, pyridinyl, quinolinyl, isoquinolinyl, quinoxalinyl, 1,8-naphthyridinyl, 1,6-naphthyridinyl, indolyl, phenyl which is substituted by R13, R14, R15 and R16 or pyridinyl which is substituted by R17 and R18, wherein
- R13 is fluorine, chlorine, bromine, hydroxy, 1-2C-alkyl, trifluoromethyl, 1-4C-alkoxy, 1-4C-alkoxy which is completely or predominantly substituted by fluorine, cyclopentyloxy, cyclopropylmethoxy, benzyloxy, amino, aminocarbonylmethoxy, 1-2C-alkylcarbonylamino, 1-2C-alkylcarbonyloxy, 1-2C-alkoxycarbonyl or 1-2C-alkoxycarbonylmethoxy,
- R14 is hydrogen, fluorine, chlorine, amino, 1-2C-alkyl, 1-2C-alkoxy or 1-2C-alkoxy which is completely or predominantly substituted by fluorine,
- R15 is hydrogen, chlorine or 1-2C-alkyl,
- R16 is hydrogen or 1-2C-alkyl,
- R17 is fluorine, chlorine, 1-2C-alkyl, trifluoromethyl, 1-2C-alkoxy, di-1-2C-alkylamino, piperidinyl or morpholinyl,
- R18 is hydrogen, fluorine, 1-2C-alkyl or 1-2C-alkoxy, or a salt of the compound.

In another preferred embodiment, the invention relates to a compound of formula 1, wherein
R1 represents a phenyl derivative of formulae (a), (b) or (c)

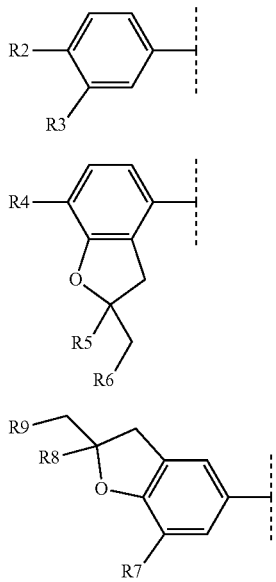

wherein
R2 is methoxy, ethoxy or difluoromethoxy,
R3 is methoxy, ethoxy or cyclopropylmethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy
R8 is methyl,
R9 is hydrogen,
R10 is methyl or ethyl,
R11 is methyl, ethyl or propyl,
or R10 and R11 together with the carbon atom, to which they are bonded, form a spiro-linked cyclopentane ring,
A is C(O),
R12 is phenyl, 3-dimethylaminophenyl, 2-ethylphenyl, 3-methylphenyl, 2,5-dimethylphenyl, 2-chloro-5-ethoxyphenyl, 2-chloro-5-isopropoxyphenyl, 3-(acetyloxy)phenyl, 3-methylcarbonylaminophenyl, 2-methyl-4-hydroxyphenyl, 2,4,6-trichlorophenyl, 2-methoxyphenyl, 3-methoxyphenyl, 4-methoxyphenyl, 3-ethoxyphenyl, 3-isopropoxyphenyl, 2,4-dimethoxyphenyl, 3-(2,2,2-trifluoroethoxy)phenyl, 2-trifluoromethoxyphenyl, 3-(cyclopropylmethoxy)-4-(difluoromethoxy)phenyl, 5-cyclopropylmethoxy-2-methylphenyl, 5-isopropoxy-2-methylphenyl, 5-isopropoxy-2-chlorophenyl, 2,4-dimethoxyphenyl, 2,6-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 5-tert-butoxy-2-methylphenyl, 5-difluoromethoxy-2-methylphenyl, 5-trifluoromethoxy-2-methylphenyl, 2-fluorophenyl, 3-fluorophenyl, 2-chlorophenyl, 3-chlorophenyl, 2-bromophenyl, 2,3-difluorophenyl, 2,6-difluorophenyl, 4-amino-3-trifluoromethylphenyl, 5-amino-2-chlorophenyl, 2-(aminocarbonylmethoxy)phenyl, 5-benzyloxy-2-chlorophenyl, 5-benzyloxy-2-methylphenyl, 5-(2,6-dichlorobenzyl)oxy-2-methylphenyl, 2-methoxycarbonylphenyl, 2-(methylcarbonyloxy)phenyl, 3-(methylcarbonyloxy)phenyl, naphthalen-1-yl, naphthalen-2-yl, 1-bromo-naphthalen-1-yl, 8-bromo-naphthalen-1-yl, 2-methyl-naphthalen-1-yl, 6-hydroxy-naphthalen-1-yl, 1-methoxy-naphthalen-2-yl, 2-methoxy-naphthalen-1-yl, 3-methoxy-naphthalen-2-yl, 4,7-dimethoxy-naphthalen-2-yl, 4-(dimethylamino)-naphthalen-1-yl, 4-(trifluoromethyl)pyridin-3-yl, 2-methoxypyridin-3-yl, 3-chloropyridin-4-yl, 3,5-difluoropyridin-2-yl, 3-methylpyridin-2-yl, 2,6-dimethoxypyridin-3-yl, 2-(piperidin-1-yl)pyridin-4-yl, 2-(morpholin-4-yl)pyridin-4-yl, quinolin-2-yl, quinolin-4-yl, quinolin-5-yl, quinolin-6-yl, quinolin-7-yl, quinolin-8-yl, 4-methyl-quinolin-2-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl,
or a salt, a stereoisomer or a salt of a stereoisomer of the compound.

In a further preferred embodiment, the invention relates to a compound of formula 1, wherein R1 represents a phenyl derivative of formulae (a), (b) or (c)

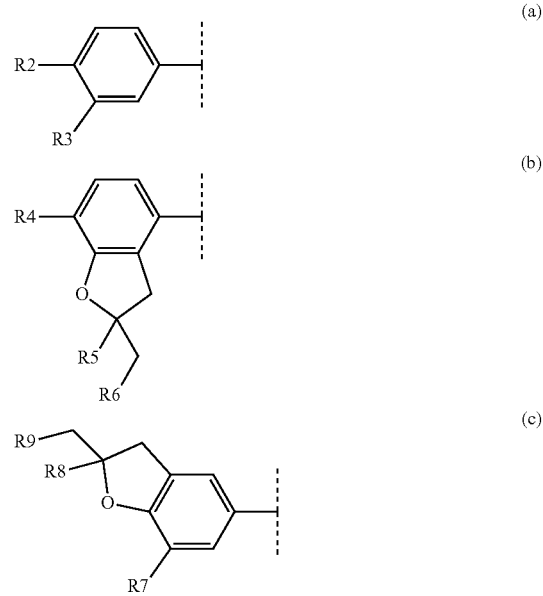

wherein
R2 is methoxy,
R3 is methoxy,
R4 is methoxy,
R5 is methyl,
R6 is hydrogen,
R7 is methoxy,
R8 is methyl,
R9 is hydrogen,
R10 is methyl,
R11 is methyl,
A is C(O),
R12 is 2,4,6-trichlorophenyl, 2-methoxyphenyl, 3-methoxyphenyl, 3-ethoxyphenyl, 3-isopropoxyphenyl, 3-(2,2,2-trifluoroethoxy)phenyl, 3-(cyclopropylmethoxy)-4-(difluoromethoxy)phenyl, 5-isopropoxy-2-methylphenyl, 2,4-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 3-fluorophenyl, 3-chlorophenyl, 4-amino-3-trifluoromethylphenyl, 5-amino-2-chlorophenyl, 2-(aminocarbonylmethoxy)phenyl, 5-benzyloxy-2-methylphenyl, 2-methoxycarbonylphenyl, 2-(methylcarbonyloxy)phenyl, 3-(methylcarbonyloxy)phenyl, naphthalen-1-yl, 4-(trifluoromethyl)pyridin-3-yl, 2-methoxypyridin-3-yl, 3-chloropyridin-4-yl, 3,5-difluoropyridin-2-yl, 3-methylpyridin-2-yl, 2,6-dimethoxypyridin-3-yl, 2-(piperidin-1-yl)pyridin-4-yl, 2-(morpholin-4-yl)pyridin-4-yl, quinolin-2-yl, quinolin-4-yl, quinolin-5-yl, quinolin-6-yl, quinolin-7-yl, quinolin-8-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl;

or a salt of the compound.

In another preferred embodiment, the invention relates to a compound of formula 1, wherein R1 represents a phenyl derivative of formula (a)

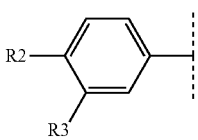

wherein
R2 is methoxy, ethoxy or difluoromethoxy,
R3 is methoxy, ethoxy or cyclopropylmethoxy,
R10 is methyl or ethyl,
R11 is methyl, ethyl or propyl,
or R10 and R11 together with the carbon atom, to which they are bonded, form a spiro-linked cyclopentane ring,
A is C(O),
R12 is phenyl, 3-dimethylaminophenyl, 2-ethylphenyl, 3-methylphenyl, 2-chloro-5-ethoxyphenyl, 2-chloro-5-isopropoxyphenyl, 3-(acetyloxy)phenyl, 3-methylcarbonylaminophenyl, 2-methyl-4-hydroxyphenyl, 2,4,6-trichlorophenyl, 2-methoxyphenyl, 3-methoxyphenyl, 4-methoxyphenyl, 3-ethoxyphenyl, 3-isopropoxyphenyl, 2,4-dimethoxyphenyl, 3-(2,2,2-trifluoroethoxy)phenyl, 2-trifluoromethoxyphenyl, 3-(cyclopropylmethoxy)-4-(difluoromethoxy)phenyl, 5-cyclopropylmethoxy-2-methylphenyl, 5-isopropoxy-2-methylphenyl, 5-isopropoxy-2-chlorophenyl, 2,4-dimethoxyphenyl, 2,6-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 5-tert-butoxy-2-methylphenyl, 5-difluoromethoxy-2-methylphenyl, 5-trifluoromethoxy-2-methylphenyl, 3-fluorophenyl, 2-chlorophenyl, 3-chlorophenyl, 2-bromophenyl, 2,3-difluorophenyl, 2,6-difluorophenyl, 4-amino-3-trifluoromethylphenyl, 5-amino-2-chlorophenyl, 2-(aminocarbonylmethoxy)phenyl, 5-benzyloxy-2-chlorophenyl, 5-benzyloxy-2-methylphenyl, 5-(2,6-dichlorobenzyl)oxy-2-methylphenyl, 2-methoxycarbonylphenyl, 2-(methylcarbonyloxy)phenyl, 3-(methylcarbonyloxy)phenyl, naphthalen-1-yl, naphthalen-2-yl, 1-bromo-naphthalen-1-yl, 8-bromo-naphthalen-1-yl, 2-methyl-naphthalen-1-yl, 6-hydroxy-naphthalen-1-yl, 1-methoxy-naphthalen-2-yl, 2-methoxy-naphthalen-1-yl, 3-methoxy-naphthalen-2-yl, 4,7-dimethoxy-naphthalen-2-yl or 4-(dimethylamino)-naphthalen-1-yl, or a salt, a stereoisomer or a salt of a stereoisomer of the compound.

In another preferred embodiment, the invention relates to a compound of formula 1, wherein R1 represents a phenyl derivative of formula (a)

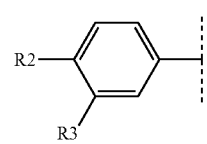

wherein
R2 is methoxy,
R3 is methoxy,
R10 is methyl,
R11 is methyl,
A is C(O),
R12 is 2,4,6-trichlorophenyl, 2-methoxyphenyl, 3-methoxyphenyl, 3-ethoxyphenyl, 3-isopropoxyphenyl, 3-(2,2,2-trifluoroethoxy)phenyl, 3-(cyclopropylmethoxy)-4-(difluoromethoxy)phenyl, 5-isopropoxy-2-methylphenyl, 2,4-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 3-fluorophenyl, 3-chlorophenyl, 4-amino-3-trifluoromethylphenyl, 5-amino-2-chlorophenyl, 2-(aminocarbonylmethoxy)phenyl, 5-benzyloxy-2-methylphenyl, 2-methoxycarbonylphenyl, 2-(methylcarbonyloxy)phenyl, 3-(methylcarbonyloxy)phenyl or naphthalen-1-yl, or a salt of the compound.

In another preferred embodiment, the invention relates to a compound of formula 1, wherein R1 represents a phenyl derivative of formula (a)

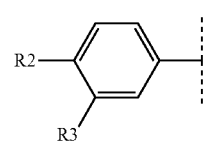

wherein
R2 is methoxy,
R3 is methoxy,
R10 is methyl,
R11 is methyl,
A is C(O),
R12 is 4-(trifluoromethyl)pyridin-3-yl, 2-methoxypyridin-3-yl, 3-chloropyridin-4-yl, 3,5-difluoropyridin-2-yl, 3-methylpyridin-2-yl, 2,6-dimethoxypyridin-3-yl, 2-(piperidin-1-yl)pyridine-4-yl or 2-(morpholin-4-yl)pyridine-4-yl, or a salt of the compound.

In another preferred embodiment, the invention relates to a compound of formula 1, wherein
R1 represents a phenyl derivative of formula (a)

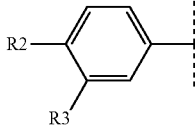

wherein
R2 is methoxy,
R3 is methoxy,
R10 is methyl,
R11 is methyl,
A is C(O),
R12 is quinolin-2-yl, quinolin-4-yl, quinolin-5-yl, quinolin-6-yl, quinolin-7-yl, quinolin-8-yl, 4-methyl-quinolin-2-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl;
or a salt of the compound.

In another preferred embodiment, the invention relates to a compound of formula 1, wherein
R1 represents a phenyl derivative of formula (a)

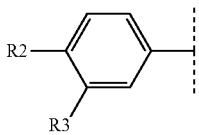

wherein
R2 is methoxy,
R3 is methoxy,
R10 is methyl,
R11 is methyl,
A is C(O),
R12 is quinolin-2-yl, quinolin-4-yl, quinolin-5-yl, quinolin-6-yl, quinolin-7-yl, quinolin-8-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl,
or a salt of the compound.

In another preferred embodiment, the invention relates to a compound of formula 1, wherein
R1 represents a phenyl derivative of formula (b)

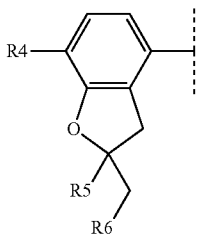

wherein
R4 is methoxy,
R5 is methyl,
R6 is hydrogen,
or R5 and R6 together and with inclusion of the two carbon atoms, to which they are bonded, form a spiro-linked cyclopentane ring,
R10 is methyl,
R11 is methyl,
A is C(O),
R12 is 2-hydroxyphenyl, 2-fluorophenyl, 2,5-dimethylphenyl, 2-methoxyphenyl, 2,4-dimethoxyphenyl, 5-hydroxy-2-methylphenyl, 5-benzyloxy-2-methylphenyl, 5-difluoromethoxy-2-methylphenyl, 5-trifluoromethoxy-2-methylphenyl, or 2-(methylcarbonyloxy)phenyl,
or a salt of the compound.

In another preferred embodiment, the invention relates to a compound of formula 1, wherein R1 represents a phenyl derivative of formula (b)

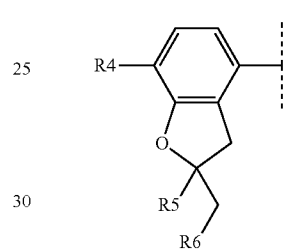

wherein
R4 is methoxy,
R5 is methyl,
R6 is hydrogen,
R10 is methyl,
R11 is methyl,
A is C(O),
R12 is 2-hydroxyphenyl, 2-methoxyphenyl or 2-(methylcarbonyloxy)phenyl,
or a salt of the compound.

In another preferred embodiment, the invention relates to a compound of formula 1, wherein R1 represents a phenyl derivative of formula (c)

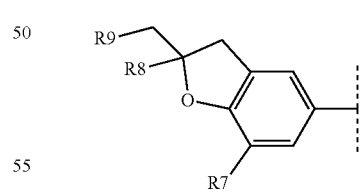

wherein
R7 is methoxy,
R8 is methyl,
R9 is hydrogen,
R10 is methyl,
R11 is methyl,
A is C(O),
R12 is 5-(benzyloxy)-2-methylphenyl or 5-hydroxy-2-methylphenyl,
or a salt of the compound.

In another preferred embodiment, the invention relates to a compound of formula 1, wherein R1 represents a phenyl derivative of formulae (a), (b) or (c)

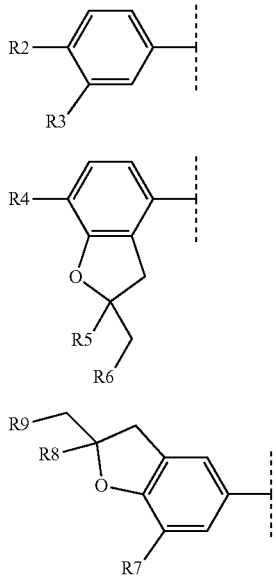

wherein
R2 is methoxy or difluoromethoxy,
R3 is methoxy or cyclopropylmethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy,
R8 is methyl,
R9 is hydrogen,
R10 is methyl or ethyl,
R11 is methyl, ethyl or propyl,
or R10 and R11 together with the carbon atom, to which they are bonded, form a spiro-linked cyclopentane ring,
A is S(O)$_2$,
R12 is phenyl, naphthalenyl, quinolinyl, indolyl, phenyl which is substituted by R13, R14, R15 and R16 or indolyl substituted by R22,
wherein
R13 is fluorine, chlorine, bromine, cyano, hydroxycarbonyl, 1-4C-alkyl, trifluoromethyl, 1-2C-alkoxycarbonyl, 1-2C-alkoxy or 1-2C-alkoxy which is completely or predominantly substituted by fluorine,
R14 is hydrogen, chlorine, 1-4C-alkyl, 1-2C-alkoxy or 1-2C-alkoxycarbonyl;
R15 is hydrogen or 1-4C-alkyl,
R16 is hydrogen or 1-2C-alkyl,
R22 is 1-2C-alkyl,
or a salt, a stereoisomer or a salt of a stereoisomer of the compound.

In another preferred embodiment, the invention relates to a compound of formula 1, wherein R1 represents a phenyl derivative of formulae (a), (b) or (c)

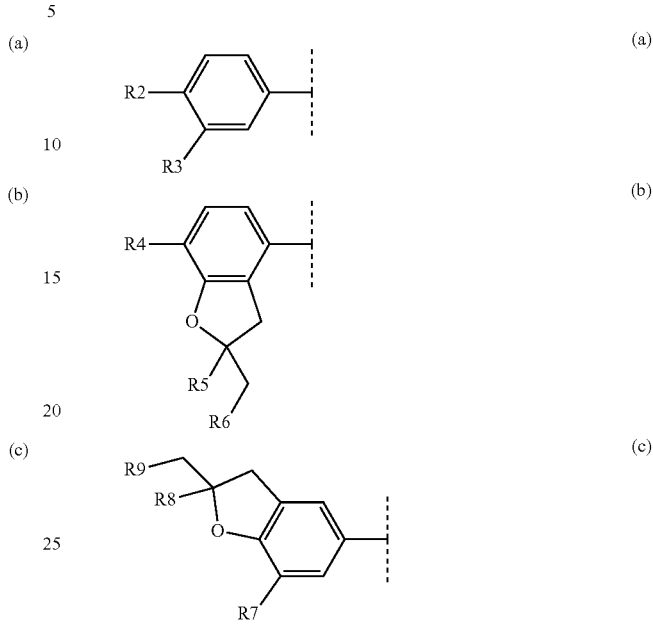

wherein
R2 is methoxy,
R3 is methoxy,
R4 is methoxy,
R5 is methyl,
R6 is hydrogen,
R7 is methoxy,
R8 is methyl,
R9 is hydrogen,
R10 is methyl,
R11 is methyl,
or R10 and R11 together with the carbon atom, to which they are bonded, form a spiro-linked cyclopentane ring,
A is S(O)$_2$,
R12 is phenyl, naphthalenyl, quinolinyl, or phenyl which is substituted by R13, R14, R15 and R16,
wherein
R13 is fluorine, chlorine, bromine, cyano, hydroxycarbonyl, 1-4C-alkyl, trifluoromethyl, 1-2C-alkoxycarbonyl, 1-2C-alkoxy or 1-2C-alkoxy which is completely or predominantly substituted by fluorine,
R14 is hydrogen, chlorine, 1-4C-alkyl, 1-2C-alkoxy or 1-2C-alkoxycarbonyl;
R15 is hydrogen or 1-4C-alkyl,
R16 is hydrogen or 1-2C-alkyl,
or a salt of the compound.

In another preferred embodiment, the invention relates to a compound of formula 1, wherein R1 represents a phenyl derivative of formulae (a), (b) or (c)

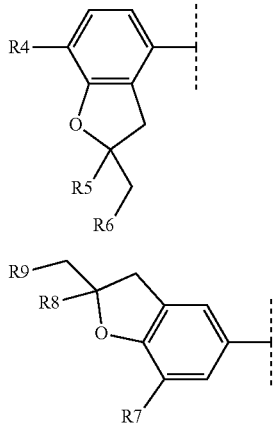

(b)

(c)

wherein
R2 is methoxy or ethoxy,
R3 is methoxy or ethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy,
R8 is methyl,
R9 is hydrogen,
R10 is methyl and
R11 is methyl, ethyl or propyl,
or R10 and R11 together with the carbon atom, to which they are bonded, form a spiro-linked cyclopentane ring,
A is S(O)$_2$,
R12 is phenyl, 2-cyanophenyl, 2-fluorophenyl, 2-bromophenyl, 2-chlorophenyl, 4-chlorophenyl, 2,5-dichlorophenyl, 2,3-dichlorophenyl, 2,4-dichlorophenyl, 3,5-dichlorophenyl, 2,6-dichlorophenyl, 3-chloro-4-fluorophenyl, 4-fluoro-2-methylphenyl, 2-chloro-4-trifluoromethylphenyl, 2-methylphenyl, 3-methylphenyl, 4-methylphenyl, 4-isopropylphenyl, 2-trifluoromethylphenyl, 3-trifluoromethylphenyl, 2,3,5,6-tetramethylphenyl, 2,4,6-triisopropylphenyl, 2-trifluoromethoxyphenyl, 2,5-dimethoxyphenyl, 5-chloro-2-methoxyphenyl, 3-(methoxycarbonyl)phenyl, 3,5-bis-(methoxycarbonyl)phenyl, naphthalen-1-yl, naphthalen-2-yl, 1-methyl-1H-indol-4-yl, 1-methyl-1H-indol-5-yl or quinolin-8-yl,
or a salt, a stereoisomer or a salt of a stereoisomer of the compound.

In another preferred embodiment, the invention relates to a compound of formula 1, wherein
R1 represents a phenyl derivative of formulae (a), (b) or (c)

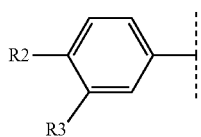

(a)

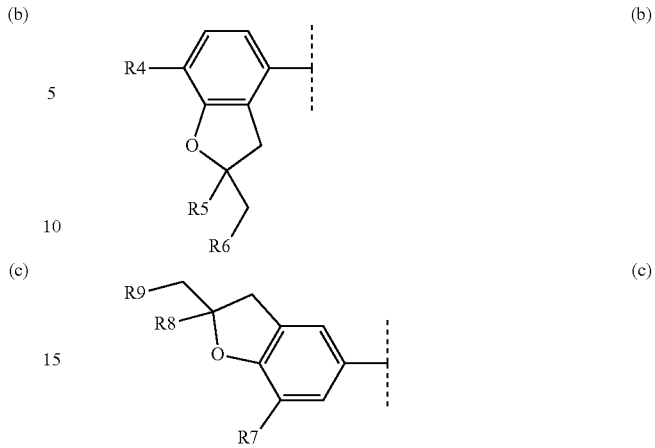

wherein
R2 is methoxy or ethoxy,
R3 is methoxy or ethoxy,
R10 is methyl and
R11 is methyl, ethyl or propyl,
or R10 and R11 together with the carbon atom, to which they are bonded, form a spiro-linked cyclopentane ring,
A is S(O)$_2$,
R12 is phenyl, 2-cyanophenyl, 2-fluorophenyl, 2-bromophenyl, 2-chlorophenyl, 4-chlorophenyl, 2,5-dichlorophenyl, 2,3-dichlorophenyl, 2,4-dichlorophenyl, 3,5-dichlorophenyl, 2,6-dichlorophenyl, 3-chloro-4-fluorophenyl, 4-fluoro-2-methylphenyl, 2-chloro-4-trifluoromethylphenyl, 2-methylphenyl, 3-methylphenyl, 4-methylphenyl, 4-isopropylphenyl, 2-trifluoromethylphenyl, 3-trifluoromethylphenyl, 2,3,5,6-tetramethylphenyl, 2,4,6-triisopropylphenyl, 2-trifluoromethoxyphenyl, 2,5-dimethoxyphenyl, 5-chloro-2-methoxyphenyl, 3-(methoxycarbonyl)phenyl, 3,5-bis-(methoxycarbonyl)phenyl, naphthalen-1-yl or naphthalen-2-yl, or a stereoisomer of the compound.

In a further preferred embodiment, the invention relates to a compound of formula 1, wherein R1 represents a phenyl derivative of formula (a)

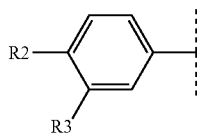
(a)

wherein
R2 is methoxy,
R3 is methoxy,
R10 is methyl,
R11 is methyl,
A is S(O)$_2$, and
R12 is phenyl, 2-cyanophenyl, 2-fluorophenyl, 2-bromophenyl, 2-chlorophenyl, 4-chlorophenyl, 2,5-dichlorophenyl, 3-methylphenyl, 4-methylphenyl, 2-trifluoromethylphenyl, 2,3,5,6-tetramethylphenyl, 2,4,6-triisopropylphenyl, 4-methoxyphenyl, 2-trifluoromethoxyphenyl, 2,5-dimethoxyphenyl, 3-(methoxycarbonyl)phenyl, 3,5-bis-(methoxycarbonyl)phenyl, naphthalen-1-yl or naphthalen-2-yl.

In another preferred embodiment, the invention relates to a compound of formula 1, wherein
R1 represents a phenyl derivative of formula (a)

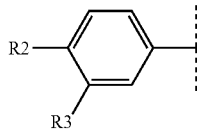
(a)

wherein
R2 is methoxy,
R3 is methoxy,
R7 is methyl,
R8 is methyl,
A is S(O)$_2$,
R12 is 1-methyl-1H-indol-4-yl, 1-methyl-1H-indol-5-yl or quinolin-8-yl,
or a salt of the compound.

In a further preferred embodiment, the invention relates to a compound of formula 1, wherein R1 represents a phenyl derivative of formula (a)

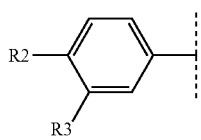
(a)

wherein
R2 is methoxy,
R3 is methoxy,
R7 is methyl,
R8 is methyl,
A is S(O)$_2$,
R12 is quinolin-8-yl,
or a salt of the compound.

In another preferred embodiment, the invention relates to a compound of formula 1, wherein
R1 represents a phenyl derivative of formula (b)

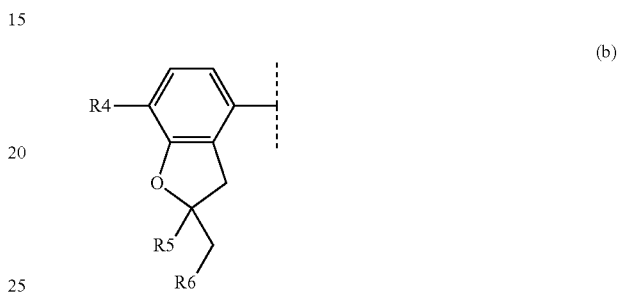
(b)

wherein
R4 is methoxy,
R5 is methyl,
R6 is hydrogen,
or R5 and R6 together and with inclusion of the two carbon atoms, to which they are bonded, form a spiro-linked cyclopentane ring,
R10 is methyl,
R11 is methyl,
A is S(O)$_2$, and
R12 is 2-cyanophenyl, 2-fluorophenyl, 3-methylphenyl or naphthalen-2-yl.

In a further preferred embodiment, the invention relates to a compound of formula 1, wherein R1 represents a phenyl derivative of formula (b)

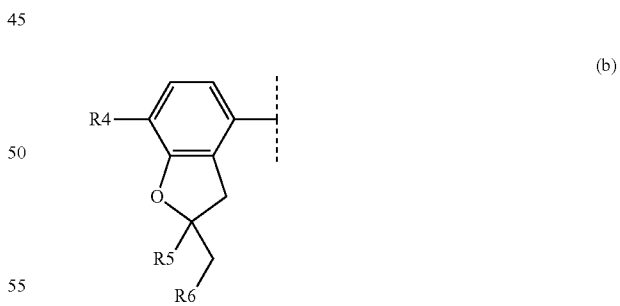
(b)

wherein
R4 is methoxy,
R5 is methyl,
R6 is hydrogen,
R10 is methyl,
R11 is methyl,
A is S(O)$_2$, and
R12 is 2-cyanophenyl, 2-fluorophenyl or naphthalen-2-yl.

In another preferred embodiment, the invention relates to a compound of formula 1, wherein
R1 represents a phenyl derivative of formula (b)

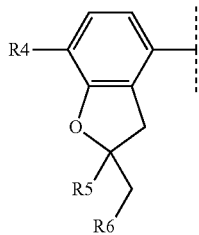

wherein
R4 is methoxy,
R5 is methyl,
R6 is hydrogen,
R10 is methyl,
R11 is methyl,
A is $S(O)_2$, and
R12 is 1-methyl-1H-indol-4-yl or quinolin-8-yl,
or a salt of the compound.

In another preferred embodiment, the invention relates to a compound of formula 1, wherein R1 represents a phenyl derivative of formula (c)

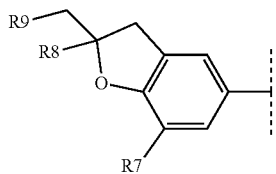

wherein
R7 is methoxy,
R8 is methyl,
R9 is hydrogen,
R10 is methyl,
R11 is methyl,
A is $S(O)_2$, and
R12 is 3-methylphenyl.

In a further preferred embodiment, the invention relates to a compound of formula 1 or a salt, a stereoisomer or a salt of a stereoisomer thereof, wherein R1 represents a phenyl derivative of formula (a) and R2, R3, R10, R11, A and R12 are as defined above.

In a further preferred embodiment, the invention relates to a compound of formula 1 or a salt, a stereoisomer or a salt of a stereoisomer thereof, wherein R1 represents a phenyl derivative of formula (a), R2 is methoxy, R3 is methoxy and R10, R11, A and R12 are as defined above.

In a further preferred embodiment, the invention relates to a compound of formula 1 or a salt thereof, wherein R1 represents a phenyl derivative of formula (a), R10 is methyl, R11 is methyl and R2, R3, A and R12 are as defined above.

In a further preferred embodiment, the invention relates to a compound of formula 1 or a salt thereof, wherein R1 represents a phenyl derivative of formula (a), R2 is methoxy, R3 is methoxy, R10 is methyl, R11 is methyl, and A and R12 are as defined above.

In a further preferred embodiment, the invention relates to a compound of formula 1 or a salt, a stereoisomer or a salt of a stereoisomer thereof, wherein R1 represents a phenyl derivative of formula (a), R12 is 2-(aminocarbonylmethoxy)phenyl, 2-bromophenyl, 3-chlorophenyl, 2-fluoro-5-hydroxyphenyl or naphthalen-1-yl and R2, R3, R10, R11 and A are as defined above.

In a further preferred embodiment, the invention relates to a compound of formula 1 or a salt, a stereoisomer or a salt of a stereoisomer thereof, wherein R1 represents a phenyl derivative of formula (a), R12 is 2-(aminocarbonylmethoxy)phenyl, 2-bromophenyl, 3-chlorophenyl, 2-fluoro-5-hydroxyphenyl or naphthalen-1-yl, A is C(O) and R2, R3, R10 and R11 are as defined above.

In a further preferred embodiment, the invention relates to a compound of formula 1 or a salt, a stereoisomer or a salt of a stereoisomer thereof, wherein R1 represents a phenyl derivative of formula (a), R12 is 2-hydroxyphenyl, 3-methoxyphenyl, 2,4,6-triisopropylphenyl, 2-fluorophenyl, 2-trifluoromethylphenyl or 2-(methoxycarbonyl)phenyl and R2, R3, R10, R11 and A are as defined above.

In a further preferred embodiment, the invention relates to a compound of formula 1 or a salt, a stereoisomer or a salt of a stereoisomer thereof, wherein R1 represents a phenyl derivative of formula (a), R12 is 2-hydroxyphenyl or 3-methoxyphenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is 2,4,6-triisopropylphenyl, 2-fluorophenyl, 2-trifluoromethylphenyl or 2-(methoxycarbonyl)phenyl, A is $S(O)_2$ and R2, R3, R10 and R11 are as defined above.

In a further preferred embodiment, the invention relates to a compound of formula 1 or a salt, a stereoisomer or a salt of a stereoisomer thereof, wherein R1 represents a phenyl derivative of formula (a), R12 is 3-methylphenyl, 3-ethoxyphenyl, 5-benzyloxy-2-methylphenyl, 5-hydroxy-2-methylphenyl or 2-cyclopentyloxyphenyl and R2, R3, R10, R11 and A are as defined above.

In a further preferred embodiment, the invention relates to a compound of formula 1 or a salt, a stereoisomer or a salt of a stereoisomer thereof, wherein R1 represents a phenyl derivative of formula (a), R12 is 3-ethoxyphenyl, 5-benzyloxy-2-methylphenyl, 5-hydroxy-2-methylphenyl or 2-cyclopentyloxyphenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is 3-methylphenyl, A is $S(O)_2$ and R2, R3, R10 and R11 are as defined above.

In a further preferred embodiment, the invention relates to a compound of formula 1 or a stereoisomer thereof, wherein R1 represents a phenyl derivative of formula (a), R12 is 2-bromophenyl, 2,3-dichlorophenyl, 2-chlorophenyl or 2,3-difluorophenyl and R2, R3, R10, R11 and A are as defined above.

In a further preferred embodiment, the invention relates to a compound of formula 1 or a stereoisomer thereof, wherein R1 represents a phenyl derivative of formula (a), R12 is 2-bromophenyl, 2-chlorophenyl or 2,3-difluorophenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is 2,3-dichlorophenyl, A is S(O)$_2$ and R2, R3, R10 and R11 are as defined above.

In a further preferred embodiment, the invention relates to a compound of formula 1 or a salt, a stereoisomer or a salt of a stereoisomer thereof, wherein R1 represents a phenyl derivative of formula (a), R12 is 5-hydroxy-2-methylphenyl, 2-chloro-5-isopropoxyphenyl, 2-chloro-5-ethoxyphenyl, 2-chloro-5-(methylcarbonylamino)phenyl, 2,6-dimethoxyphenyl or 2,5-dimethylphenyl, and R2, R3, R10, R11 and A are as defined above.

In a further preferred embodiment, the invention relates to a compound of formula 1 or a salt, a stereoisomer or a salt of a stereoisomer thereof, wherein R1 represents a phenyl derivative of formula (a), R12 is 5-hydroxy-2-methylphenyl, 2-chloro-5-isopropoxyphenyl, 2-chloro-5-ethoxyphenyl, 2-chloro-5-(methylcarbonylamino)phenyl, 2,6-dimethoxyphenyl or 2,5-dimethylphenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is naphthalen-1-yl, 2-methoxy-naphthalen-1-yl, 4,7-dimethoxy-naphthalen-2-yl or 8-bromo-naphthalen-1-yl, and R2, R3, R10, R11 and A are as defined above.

In a further preferred embodiment, the invention relates to a compound of formula 1 or a stereoisomer thereof, wherein R1 represents a phenyl derivative of formula (a), R12 is naphthalen-1-yl, 2-methoxy-naphthalen-1-yl, 4,7-dimethoxy-naphthalen-2-yl or 8-bromo-naphthalen-1-yl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is 2-fluorophenyl, 2-trifluoromethylphenyl, 2-chlorophenyl, 3-chlorophenyl, 2-methoxyphenyl or 2-ethylphenyl, and R2, R3, R10, R11 and A are as defined above.

In a further preferred embodiment, the invention relates to a compound of formula 1 or a stereoisomer thereof, wherein R1 represents a phenyl derivative of formula (a), R12 is 3-chlorophenyl, 2-methoxyphenyl or 2-ethylphenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is 2-fluorophenyl, 2-trifluoromethylphenyl or 2-chlorophenyl, and A is S(O)$_2$ and R2, R3, R10 and R11 are as defined above.

In a further preferred embodiment, the invention relates to a compound of formula 1 or a stereoisomer thereof, wherein R1 represents a phenyl derivative of formula (a), R12 is 5-cyclopropylmethoxy-2-methylphenyl, 5-[(2,6-dichlorobenzyl)oxy]-2-methylphenyl or 5-difluoromethoxy-2-methylphenyl, and R2, R3, R10, R11 and A are as defined above.

In a further preferred embodiment, the invention relates to a compound of formula 1 or a stereoisomer thereof, wherein R1 represents a phenyl derivative of formula (a), R12 is 5-cyclopropylmethoxy-2-methylphenyl, 5-[(2,6-dichlorobenzyl)oxy]-2-methylphenyl or 5-difluoromethoxy-2-methylphenyl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is naphthalen-1-yl or 2-methyl-naphthalen-1-yl, and R2, R3, R10, R11 and A are as defined above.

In a further preferred embodiment, the invention relates to a compound of formula 1 or a stereoisomer thereof, wherein R1 represents a phenyl derivative of formula (a), R12 is 2-methyl-naphthalen-1-yl, A is C(O) and R2, R3, R10 and R11 are as defined above.

In a further preferred embodiment, the invention relates to a compound of formula 1 or a stereoisomer thereof, wherein R1 represents a phenyl derivative of formula (a), R12 is naphthalen-1-yl, A is S(O)$_2$ and R2, R3, R10 and R11 are as defined above.

In a further preferred embodiment, the invention relates to a compound of formula 1 or a salt, a stereoisomer or a salt of a stereoisomer thereof, wherein R1 represents a phenyl derivative of formula (a), R12 is 1H-indol-6-yl and R2, R3, R10, R11 and A are as defined above.

In a further preferred embodiment, the invention relates to a compound of formula 1 or a salt, a stereoisomer or a salt of a stereoisomer thereof, wherein R1 represents a phenyl derivative of formula (a), R12 is 1H-indol-6-yl, A is C(O) and R2, R3, R10 and R11 are as defined above.

In a further preferred embodiment, the invention relates to a compound of formula 1 or a salt, a stereoisomer or a salt of a stereoisomer thereof, wherein R1 represents a phenyl derivative of formula (b) and R4, R5, R6, R10, R11, A and R12 are as defined above.

In a further preferred embodiment, the invention relates to a compound of formula 1 or a salt, a stereoisomer or a salt of a stereoisomer thereof, wherein R1 represents a phenyl derivative of formula (b), R4 is methoxy, R5 is methyl, R6 is hydrogen and R10, R11, A and R12 are as defined above.

In a further preferred embodiment, the invention relates to a compound of formula 1 or a salt, a stereoisomer or a salt of a stereoisomer thereof, wherein R1 represents a phenyl derivative of formula (b), R10 is methyl, R11 is methyl, and R4, R5, R6, A and R12 are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl and A and R12 are as defined above.

In a further preferred embodiment, the invention relates to a compound of formula 1, or a salt, a stereoisomer or a salt of a stereoisomer thereof, wherein R1 represents a phenyl derivative of formula (b), R12 is 2-(aminocarbonylmethoxy)phenyl, 2-bromophenyl, 3-chlorophenyl, 2-fluoro-5-hydroxyphenyl or naphthalen-1-yl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is C(O) and R12 is 2-(aminocarbonylmethoxy)phenyl, 2-bromophenyl, 3-chlorophenyl, 2-fluoro-5-hydroxyphenyl or naphthalen-1-yl.

In a further preferred embodiment, the invention relates to a compound of formula 1, or a salt, a stereoisomer or a salt of a stereoisomer thereof, wherein R1 represents a phenyl derivative of formula (b), R12 is 2-hydroxyphenyl, 3-methoxyphenyl, 2,4,6-triisopropylphenyl, 2-fluorophenyl, 2-trifluoromethylphenyl or 2-(methoxycarbonyl)phenyl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is C(O) and R12 is 2-hydroxyphenyl or 3-methoxyphenyl.

In a further preferred embodiment, the invention relates to a compound of formula 1, wherein R1 represents a phenyl derivative of formula (b), R4 is methoxy, R5 is methyl, R6 is hydrogen, R10 is methyl, R11 is methyl, A is $S(O)_2$ and R12 is 2,4,6-triisopropylphenyl, 2-fluorophenyl, 2-trifluoromethylphenyl or 2-(methoxycarbonyl)phenyl.

In a further preferred embodiment, the invention relates to a compound of formula 1, or a salt, a stereoisomer or a salt of a stereoisomer thereof, wherein R1 represents a phenyl derivative of formula (b), R12 is 3-methylphenyl, 3-ethoxyphenyl, 5-benzyloxy-2-methylphenyl, 5-hydroxy-2-methylphenyl or 2-cyclopentyloxyphenyl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is C(O) and R12 is 3-ethoxyphenyl, 5-benzyloxy-2-methylphenyl, 5-hydroxy-2-methylphenyl or 2-cyclopentyloxyphenyl.

In a further preferred embodiment, the invention relates to a compound of formula 1, wherein R1 represents a phenyl derivative of formula (b), R4 is methoxy, R5 is methyl, R6 is hydrogen, R10 is methyl, R11 is methyl, A is $S(O)_2$ and R12 is 3-methylphenyl.

In a further preferred embodiment, the invention relates to a compound of formula 1 or a stereoisomer thereof, wherein R1 represents a phenyl derivative of formula (b), R12 is 2-methoxyphenyl, 2-fluorophenyl or 2,5-dimethylphenyl, and R4, R5, R6, R10, R11 and A are as defined above.

In a further preferred embodiment, the invention relates to a compound of formula 1, wherein R1 represents a phenyl derivative of formula (b), R4 is methoxy, R5 is methyl, R6 is hydrogen, R10 is methyl, R11 is methyl, A is C(O) and R12 is 2-methoxyphenyl, 2-fluorophenyl or 2,5-dimethylphenyl.

In a further preferred embodiment, the invention relates to a compound of formula 1, or a salt, a stereoisomer or a salt of a stereoisomer thereof, wherein R1 represents a phenyl derivative of formula (b), R12 is 2-methyl-5-difluoromethoxyphenyl, 5-(benzyloxy)-2-methylphenyl or 5-hydroxy-2-methylphenyl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is C(O) and R12 is 2-methyl-5-difluoromethoxyphenyl, 5-(benzyloxy)-2-methylphenyl or 5-hydroxy-2-methylphenyl.

In a further preferred embodiment, the invention relates to a compound of formula 1, or a salt, a stereoisomer or a salt of a stereoisomer thereof, wherein R1 represents a phenyl derivative of formula (b), R12 is 1-methyl-1H-indol-4-yl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is $S(O)_2$ and R12 is 1-methyl-1H-indol-4-yl.

In a further preferred embodiment, the invention relates to a compound of formula 1, or a salt, a stereoisomer or a salt of a stereoisomer thereof, wherein R1 represents a phenyl derivative of formula (b), R12 is 2-methylcarbonyloxyphenyl, 2-hydroxyphenyl or 3-methylphenyl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is C(O) and R12 is 2-methylcarbonyloxyphenyl or 2-hydroxyphenyl.

In a further preferred embodiment, the invention relates to a compound of formula 1, wherein R1 represents a phenyl derivative of formula (b), R4 is methoxy, R5 is methyl, R6 is hydrogen, R10 is methyl, R11 is methyl, A is $S(O)_2$ and R12 is 3-methylphenyl.

In a further preferred embodiment, the invention relates to a compound of formula 1, or a salt, a stereoisomer or a salt of a stereoisomer thereof, wherein R1 represents a phenyl derivative of formula (b), R12 is quinolin-8-yl and R4, R5, R6, R10, R11 and A are as defined above.

In a further preferred embodiment, the invention relates to a compound of formula 1 or a salt thereof, wherein R1 represents a phenyl derivative of formula (b), R4 is methoxy, R5 is methyl, R6 is hydrogen, R10 is methyl, R11 is methyl, A is $S(O)_2$ and R12 is quinolin-8-yl.

In a further preferred embodiment, the invention relates to a compound of formula 1, or a salt, a stereoisomer or a salt of a stereoisomer thereof, wherein R1 represents a phenyl derivative of formula (c), R12 is 2-(aminocarbonylmethoxy)phenyl, 2-bromophenyl, 3-chlorophenyl, 2-fluoro-5-hydroxyphenyl or naphthalen-1-yl and R7, R8, R9, R10, R11 and A are as defined above.

In a further preferred embodiment, the invention relates to a compound of formula 1 or a salt thereof, wherein R1 represents a phenyl derivative of formula (c), R7 is methoxy, R8 is methyl, R9 is hydrogen, R10 is methyl, R11 is methyl, A is C(O) and R12 is 2-(aminocarbonylmethoxy)phenyl, 2-bromophenyl, 3-chlorophenyl, 2-fluoro-5-hydroxyphenyl or naphthalen-1-yl.

In a further preferred embodiment, the invention relates to a compound of formula 1, or a salt, a stereoisomer or a salt of a stereoisomer thereof, wherein R1 represents a phenyl derivative of formula (c), R12 is 2-hydroxyphenyl, 3-methoxyphenyl, 2,4,6-triisopropylphenyl, 2-fluorophenyl, 2-trifluoromethylphenyl or 2-(methoxycarbonyl)phenyl and R7, R8, R9, R10, R11 and A are as defined above.

In a further preferred embodiment, the invention relates to a compound of formula 1 or a salt thereof, wherein R1 represents a phenyl derivative of formula (c), R7 is methoxy, R8 is methyl, R9 is hydrogen, R10 is methyl, R11 is methyl, A is C(O) and R12 is 2-hydroxyphenyl or 3-methoxyphenyl.

In a further preferred embodiment, the invention relates to a compound of formula 1, wherein R1 represents a phenyl derivative of formula (c), R7 is methoxy, R8 is methyl, R9 is hydrogen, R10 is methyl, R11 is methyl, A is $S(O)_2$ and R12 is 2,4,6-triisopropylphenyl, 2-fluorophenyl, 2-trifluoromethylphenyl or 2-(methoxycarbonyl)phenyl.

In a further preferred embodiment, the invention relates to a compound of formula 1, or a salt, a stereoisomer or a salt of a stereoisomer thereof, wherein R1 represents a phenyl derivative of formula (c), R12 is 3-methylphenyl, 3-ethoxyphenyl, 5-benzyloxy-2-methylphenyl, 5-hydroxy-2-methylphenyl or 2-cyclopentyloxyphenyl and R7, R8, R9, R10, R11 and A are as defined above.

In a further preferred embodiment, the invention relates to a compound of formula 1 or a salt thereof, wherein R1 represents a phenyl derivative of formula (c), R7 is methoxy, R8 is methyl, R9 is hydrogen, R10 is methyl, R11 is methyl, A is C(O) and R12 is 3-ethoxyphenyl, 5-benzyloxy-2-methylphenyl, 5-hydroxy-2-methylphenyl or 2-cyclopentyloxyphenyl.

In a further preferred embodiment, the invention relates to a compound of formula 1, wherein R1 represents a phenyl derivative of formula (c), R7 is methoxy, R8 is methyl, R9 is hydrogen, R10 is methyl, R11 is methyl, A is $S(O)_2$ and R12 is 3-methylphenyl.

It is to be understood that the invention covers all combinations of substituent groups referred to hereinabove. In particular, the invention covers all combinations of preferred groups described herein.

Salts of the compounds of formula 1 or salts of the stereoisomers of the compounds of formula 1 include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxybenzoyl)benzoates, butyrates, sulfosalicylates, maleates, laurates, malates, lactates, fumarates, succinates, oxalates, tartarates, stearates, benzenesulfonates (besilates), toluenesulfonates (tosilates), methanesulfonates (mesilates), laurylsulfonates, 3-hydroxy-2-naphthoates, lactobionates, galactarates, pyroglutamates, embonates and ascorbates.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

The compounds, the salts, the stereoisomers or the salts of the stereoisomers according to the invention may contain, e.g. when isolated in crystalline form, varying amounts of solvents. Included within the scope of the invention are, therefore, all solvates of the compounds, the salts, the stereoisomers or the salts of the stereoisomers according to the invention. Hydrates are a preferred example of said solvates.

The compounds of formula 1 and the salts thereof include stereoisomers. In case R10 and R11 represent different groups and/or R5 and —CH$_2$R6, respectively R8 and —CH$_2$R9 represent different groups, the compounds of formula 1 or the salts thereof have one or two stereogenic centers. Each of said stereogenic centers may have the absolute configuration R or the absolute configuration S (according to Cahn, Ingold and Prelog).

Accordingly, the stereoisomers (4R) and (4S) in case of a compound of formula 1a*, the stereoisomers (2R), (2S), (4R), (4S), (2R, 4R), (2R, 4S), (2S, 4R) and (2S, 4S) in case of a compound of formula 1 b*and the stereoisomers (2R), (2S), (4R), (4S), (2R, 4R), (2R, 4S), (2S, 4R) and (2S, 4S) in case of a compound of formula 1c*

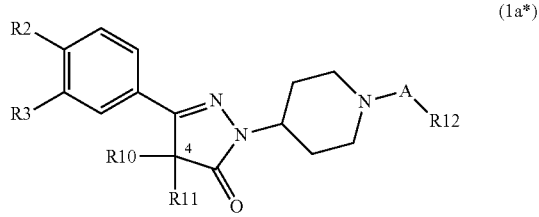

(1a*)

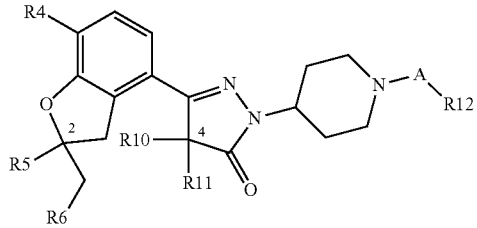

(1b*)

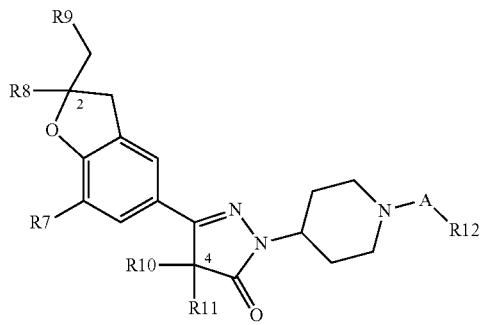

(1c*)

are part of the invention (the numbers refer to the atoms indicated in formulae 1a*, 1b* and 1c*).

The invention further includes all mixtures of the stereoisomers mentioned above independent of the ratio, including the racemates.

Some of the compounds of formula 1, salts thereof, stereoisomers thereof or salts of the latter may exist in different crystalline forms (polymorphs), which are within the scope of the invention.

The compounds according to the invention can be prepared as follows.

As shown in reaction scheme 1 the compounds of formula 1, wherein R1, R10, R11, A and R12 have the above-mentioned meanings can be obtained by reacting a corresponding compound of formula 4 with a compound of formula 2, wherein X is a halide, preferably chlorine and A and R12 have the above-mentioned meanings in an appropriate solvent, such as, for example dichloromethane, chloroform, toluene, tetrahydrofurane, acetonitril, N,N-dimethylformamide or 1-methyl-pyrrolidin-2-one, preferably in the presence of a base, such as, for example potassium carbonate, sodium carbonate, diisopropylethylamine or triethylamine and preferably at ambient temperature.

Alternatively, the compounds of formula 1, wherein R1, R10, R11, A and R12 have the above-mentioned meanings can be obtained by reacting a corresponding compound of formula 4 with a compound of formula 3, wherein R12 has the above-mentioned meanings using standard amide bond coupling methods such as for example the use of systems of coupling reagents, anhydrides or active esters as described in the literature, for example in Chan Weng C. and White Peter D. 2000, Fmoc Solid Phase Synthesis: A Practical Approach, Oxford University Press.

The compounds of formula 4, wherein R1, R10 and R11 have the above-mentioned meanings can be prepared by reacting a corresponding compound of formula 5 with an in 4-position activated and in 1-position protected piperidine-derivative, such as, for example tert-butyl 4-(toluene-4-sulfonyloxy)piperidine-1-carboxylate or tert-butyl 4-(methanesulfonyloxy)-piperidine-1-carboxylate in an inert solvent, such as, for example N,N-dimethylformamide, 1-methyl-pyrrolidin-2-one or dioxane, in the presence of a strong base, such as, for example sodium ethoxide, potassium tert-butoxide, sodium hydride, and preferably at raised temperature, such as, for example 80 to 150° C.

Alternatively, the compounds of formula 4, wherein R1, R10 and R11 have the above-mentioned meanings can be prepared by reacting a corresponding compound of formula 6 with piperidin-4-ylhydrazine dihydrochloride in a methanol/water solvent system, preferably at raised temperatures, especially at the boiling point of the solvent system being used.

The compounds of formula 5, wherein R1, R10 and R11 have the above-mentioned meanings can be obtained by reacting an appropriately substituted α,α-disubstituted-β-oxobenzene propionic acid ester of formula 6 with hydrazine hydrate in an appropriate solvent, such as, for example an alcohol like ethanol or methanol, preferably at raised temperature, especially at the boiling point of the solvent being used. The ester of the α,α-disubstituted-β-oxobenzene propionic acid ester may be a 1-4C-alkyl ester; particularly preferred is—as shown in reaction scheme 1—the methyl ester.

The compounds of formula 6, wherein R1, R10 and R11 have the above-mentioned meanings can be prepared by reacting an activated benzoic acid derivative of formula 8, wherein R1 has the above-mentioned meanings with an ester of formula 7, wherein R10 and R11 have the above-mentioned meanings, in an inert solvent, such as, for example tetrahydrofurane, diethyl ether, toluene, N,N-dimethylformamide or 1-methyl-pyrrolidin-2-one, in the presence of a strong base, such as for example lithium diisopropylamine, butyl lithium or sodium hydride, at low temperatures, preferably below −40° C.

Alternatively, the compounds of formula 6, wherein R1, R10 and R11 have the above-mentioned meanings can be prepared by reacting an aryl halide derivative of formula 10, wherein R1 has the above-mentioned meanings, with an diester of formula 9, wherein R10 and R11 have the above-mentioned meanings, via metal mediated methods. Preferably the aryl bromo derivative of formula 10, wherein R1 has the above-mentioned meanings, is converted into the corresponding Grignard reagent according to standard methods. This Grignard reagent then is reacted with the diester of formula 9, wherein R10 and R11 have the above-mentioned meanings, in an inert solvent, such as, for example tetrahydrofurane, diethyl ether or toluene, at low temperatures, preferably below −40° C.

Suitable esters of formula 7 are for example methyl 2-methylproponate, methyl-2-methylbutanoate, methyl-2-ethylbutanoate, methyl 2-methylpentanoate and methyl cyclopentancarboxylate.

The esters of formula 7 are commercially available or can be prepared according to procedures known in the art.

Suitable diesters of formula 9 are for example dimethyl dimethylmalonate, dimethyl ethyl(methyl)malonate, dimethyl dimethylmalonate, dimethyl methyl(propyl)malonate and dimethyl cyclopentane-1,1-dicarboxylate.

The diesters of formula 9 are commercially available or can be prepared according to procedures known in the art.

The activated benzoic acid derivatives of formula 8 can be obtained, for example, according to the procedures described in the international patent applications WO92/12961, WO94/02465, WO95/01338 and WO96/03399.

The compounds of formula 10 are commercially available or can be prepared according to procedures known in the art.

An alternative synthesis route to compounds of formula 5 is described in the European patent application EP0126651.

Reaction Scheme 1:

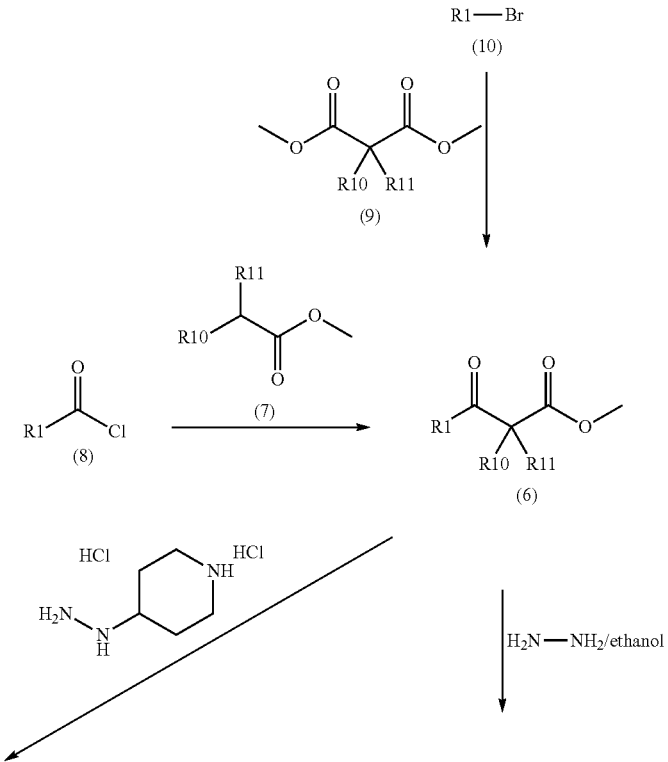

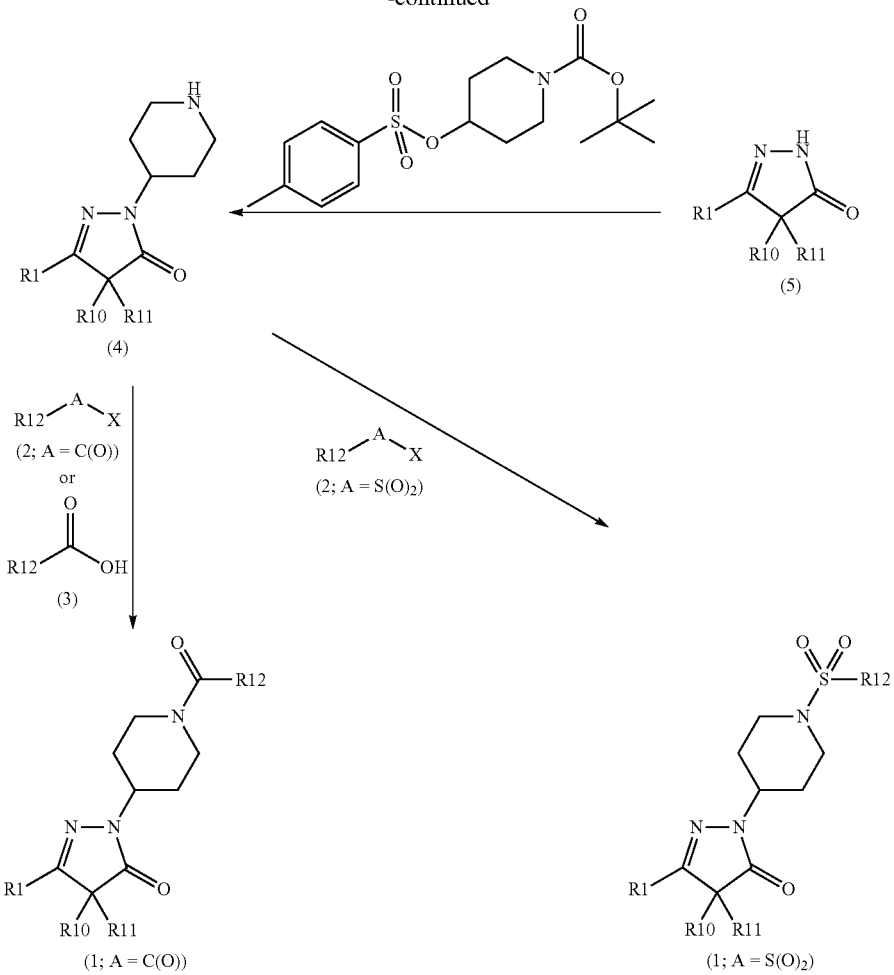

Compounds of formula 1 can be converted into further compounds of formula 1 by methods known in the art. For example
- a compound of formula 1, wherein R12 contains a carboxylic acid ester function (e.g. where R12 is 3-methoxycarbonylphenyl) can be prepared from a compound of formula 1, wherein R12 contains a carboxylic acid function (e.g. where R12 is 3-hydroxycarbonylphenyl) by an esterfication reaction
- a compound of formula 1, wherein R12 contains a hydroxyl function (e.g. where R12 is 2-hydroxyphenyl) can be prepared from a compound of formula 1, wherein R12 contains a protected hydroxyl function (e.g. where R12 is 2-acetyloxy-phenyl, 2-benzyloxy-phenyl or 2-methoxymethoxy-phenyl) by an appropriate deprotection reaction
- a compound of formula 1, wherein R12 contains an alkoxy function (e.g. where R12 is 2-cyclopentyloxy-phenyl) can be prepared from a compound of formula 1, wherein R12 contains a hydroxyl function (e.g. where R12 is 2-hydroxy-phenyl) by an alkylation reaction using for example an alkylhalide and a base
- a compound of formula 1, wherein R12 contains an amino function (e.g. where R12 is 3-amino-phenyl) can be prepared from a compound of formula 1, wherein R12 contains a nitro function (e.g. where R12 is 3-nitro-phenyl) by an reduction reaction using for example a palladium catalyst and an hydrogen atmosphere
- a compound of formula 1, wherein R12 contains a carboxylic acid amide function (e.g. where R12 is 3-acetylamino-phenyl) can be prepared from a compound of formula 1, wherein R12 contains an amino function (e.g. where R12 is 3-amino-phenyl) by an amide coupling reaction using for example an acid chloride and a base A further possibility to prepare compounds of formula 1 is to use a temporarily protective group in order to introduce a specific substituent at the end of a reaction sequence. This method can be advantageously used, for example, to introduce different alkoxy groups in the position of the R3 substituent. Examples 23 and 40 have been prepared using such a method; here, the benzyl group served as a temporarily protective group for a hydroxyl group in R3 position.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula 1 and the stereoisomers thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds according to the invention can be obtained e.g. by asymmetric synthesis, by using chiral starting compounds in synthesis and by splitting up enantiomeric and diasteriomeric mixtures obtained in synthesis. Preferably, the pure diastereomeric and pure enantiomeric compounds of the invention are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts, the stereoisomers or the salts of the stereisomers thereof represent preferred embodiments of the invention.

EXAMPLES

The following abbreviations are used: min: minutes, h: hour(s), DCM: dichloromethane, THF: tetrahydrofurane, EA: ethyl acetate, DMF: N,N-dimethylformamide, TEA: triethyl amine, DIPEA: diisopropyl ethyl amine, PE: petrol ether (60/80), HOBt: 1-hydroxybenzotriazole, HOAt: 1-hydroxy-7-azabenzotriazole, EDCi*HCl: 1-ethyl-3-(3-dimethylaminopropyl)carbodiimide hydrochloride, DCC: N,N'-dicyclohexylcarbodiimide, TOTU: O-[(ethoxycarbonyl)cyanomethyleneamino]-N,N,N',N'-tetramethyluronium tetrafluoroborate, M.p.: melting point, B. p.: boiling point, RT: room temperature (20 to 25° C.), MS: mass spectrometry, HRMS: high resolution mass spectrometry, calc: calculated and TLC: thin layer chromatography.

Final Products

General Procedure 1 (GP1):

One equivalent of the starting amino compound (Reaction scheme 1; compound of formula 4) and two equivalents of TEA are dissolved in a suitable amount of DCM (10 ml DCM for 1 mmol of the starting amino compound), and one equivalent of the respective acid chloride (Reaction scheme 1; compound of formula 2) is added to the reaction. Alternatively, one equivalent the of hydrochloric acid salt of the starting amino compound may be used with three instead of two equivalents of TEA. The reaction is stirred at RT until the reaction is completed according to TLC analysis (typically 12 to 24 h). The reaction is quenched with 1 M aqueous sodium carbonate solution. The phases are separated and the organic phase is washed with another portion of 1 M aqueous sodium carbonate solution and then with 2 M aqueous hydrochloric acid. The organic phase is dried over MgSO$_4$, and the solvent is removed under reduced pressure resulting in a crude product, which is purified either by crystallization (typically from EA and diethyl ether) or by column chromatography (typically with a stationary phase of silica gel and a system of EA and PE as eluent) to yield the respective title compound.

General Procedure 2 (GP2):

A solution of 1.2 equivalents of the starting carboxylic acid compound (Reaction scheme 1; compound of formula 3), 1.25 equivalents HOAt, 1.25 equivalents TOTU and two equivalents DIPEA in anhydrous DMF (2 ml DMF for 1.2 mmol of the starting carboxylic acid compound) is stirred for 30 minutes at RT, one equivalent of the starting amino compound (Reaction scheme 1; compound of formula 4) is added, and the reaction mixture is stirred at RT until the reaction is completed according to TLC analysis (typically 1-3 h). Work-up of the reaction might be done by one of the following alternatives (WU1 or WU2): Alternative 1 (WU1) is used, if the reaction product precipitates during the course of the reaction. Here, the solids are filtered off, and washed with water and diethyl ether. Drying of the solid under reduced pressure yields the title compound. Alternative 2 (WU2) is used, if the reaction product does not precipitate during the course of the reaction. Here, the reaction mixture is portioned between water and DCM, the phases are separated, the organic phase is dried over MgSO$_4$, and the solvent is removed under reduced pressure resulting in a crude product, which is purified by column chromatography (typically with a stationary phase of amino phase silica gel and DCM as eluent) to yield the respective title compound.

General Procedure 3 (GP3):

One equivalent of the starting amino compound (Reaction scheme 1; compound of formula 4), 1.3 equivalents of the staring carboxylic acid compound (Reaction scheme 1; compound of formula 3) are dissolved in DCM (10 ml DCM for 1 mmol of the starting amino compound), 1.2 equivalents EDCi*HCl are added and the mixture is stirred at RT until the reaction is completed according to TLC analysis (typically 1-3 h). The reaction is quenched with 1 M aqueous sodium carbonate solution. The phases are separated and the organic phase is washed with another portion of 1 M aqueous sodium carbonate solution. The organic phase is dried over $MgSO_4$ and the solvent is removed under reduced pressure resulting in a crude product, which is purified by crystallization (typically from methanol to yield the respective title compound.

The chemical names of the Final Products have been generated using the software ACD/NAME Library DLL 9.6.0.7481.

1. 2-({4-[3-(3,4-Dimethoxyphenyl)-4,4-dimethyl-5-oxo-4,5-dihydro-1H-pyrazol-1-yl]piperidin-1-yl}sulfonyl)benzonitrile The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-cyanobenzenesulfonyl chloride as starting compounds. The crude product is purified by crystallization from EA and diethyl ether to yield the title compound.

M.p. 198-199° C.
HRMS $[C_{25}H_{28}N_4O_5S]$: calc: 496.1780 found: 496.1776

2. Methyl 2-({4-[3-(3,4-dimethoxyphenyl)-4,4-dimethyl-5-oxo-4,5-dihydro-1H-pyrazol-1-yl]piperidin-1-yl}sulfonyl)benzoate The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and methyl 2-(chlorosulfonyl)benzoate as starting compounds. The crude product is purified by crystallization from EA and diethyl ether to yield the title compound.

M.p. 179° C.
HRMS $[C_{26}H_{31}N_3O_7S]$: calc: 529.1883 found: 529.1880

3. 5-(3,4-Dimethoxyphenyl)-4,4-dimethyl-2-{1-[(4-methylphenyl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-methylbenzenesulfonyl chloride as starting compounds. The crude product is purified by crystallization from methanol to yield the title compound.

HRMS $[C_{25}H_{31}N_3O_5S]$: calc: 485.1984 found: 485.1993

4. 2-{1-[(4-tert-Butylphenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-tert-butylbenzenesulfonyl chloride as starting compounds. The crude product is purified by crystallization from methanol to yield the title compound.

HRMS $[C_{28}H_{37}N_3O_5S]$: calc: 527.2454 found: 527.2470

5. 5-(3,4-Dimethoxyphenyl)-2-{1-[(4-methoxyphenyl)sulfonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-methoxybenzenesulfonyl chloride as starting compounds. The crude product is purified by crystallization from methanol to yield the title compound.

HRMS $[C_{25}H_{31}N_3O_6S]$: calc: 501.1934 found: 501.1949

6. 5-(3,4-Dimethoxyphenyl)-4,4-dimethyl-2-[1-(quinolin-8-ylsulfonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and quinoline-8-sulfonyl chloride as starting compounds. The crude product is purified by crystallization from methanol to yield the title compound.

HRMS $[C_{27}H_{30}N_4O_5S]$: calc: 522.1937 found: 522.1937

7. 5-(3,4-Dimethoxyphenyl)-4,4-dimethyl-2-[1-(naphthalen-1-ylsulfonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and naphthalene-1-sulfonyl chloride as starting compounds. The crude product is purified by crystallization from methanol to yield the title compound.

HRMS $[C_{28}H_{31}N_3O_5S]$: calc: 521.1984 found: 521.1993

8. 5-(3,4-Dimethoxyphenyl)-4,4-dimethyl-2-{1-[(2-methylphenyl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-methylbenzenesulfonyl chloride as starting compounds. The crude product is purified by crystallization from methanol to yield the title compound.

HRMS $[C_{25}H_{31}N_3O_5S]$: calc: 458.1984 found: 458.1998

9. 5-(3,4-Dimethoxyphenyl)-4,4-dimethyl-2-(1-{[2,4,6-tri(propan-2-yl)phenyl]sulfonyl}piperidin-4-yl)-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,4,6-triisopropylbenzenesulfonyl chloride as starting compounds. The crude product is purified by crystallization from methanol to yield the title compound.

HRMS $[C_{33}H_{47}N_3O_5S]$: calc: 597.3236 found: 597.3255

10. 5-(3,4-Dimethoxyphenyl)-2-{1-[(2,5-dimethoxyphenyl)sulfonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,5-dimethoxybenzenesulfonyl chloride as starting compounds. The crude product is purified by crystallization from methanol to yield the title compound.

HRMS [$C_{26}H_{33}N_3O_7S$]: calc: 531.2039 found: 531.2057

11. 5-(3,4-Dimethoxyphenyl)-4,4-dimethyl-2-{1-[(3-methylphenyl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-methylbenzenesulfonyl chloride as starting compounds. The crude product is purified by crystallization from methanol to yield the title compound.

M.p. 217° C.

HRMS [$C_{25}H_{31}N_3O_5S$]: calc: 485.1984 found: 485.1990

12. 3-({4-[3-(3,4-Dimethoxyphenyl)-4,4-dimethyl-5-oxo-4,5-dihydro-1H-pyrazol-1-yl]piperidin-1-yl}carbonyl)phenyl acetate A mixture of 10 g 5-(3,4-dimethoxyphenyl)-4,4-dimethyl-2-(piperidin-4-yl)-2,4-dihydro-3H-pyrazol-3-one (compound B1), 8 g of 3-(acetyloxy)benzoic acid and 7 g of DCC in 150 ml of DCM is stirred for 2 h until the reaction is complete according to TLC analysis. The reaction mixture is quenched with water, the phases are separated and the organic phase is washed with water again. The organic phase is dried over $MgSO_4$, and the solvent is removed under reduced pressure resulting in a crude product, which is purified by crystallization from methanol to yield the title compound.

HRMS [$C_{27}H_{31}N_3O_6$]: calc: 493.2213 found: 493.2221

13. 5-(3,4-Dimethoxyphenyl)-4,4-dimethyl-2-[1-(phenylsulfonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and benzenesulfonyl chloride as starting compounds. The crude product is purified by crystallization from methanol to yield the title compound.

HRMS [$C_{24}H_{29}N_3O_5S$]: calc: 471.1828 found: 471.1834

14. 5-(3,4-Dimethoxyphenyl)-2-{1-[(2-fluorophenyl)sulfonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-fluorobenzenesulfonyl chloride as starting compounds. The crude product is purified by crystallization from methanol to yield the title compound.

HRMS [$C_{24}H_{28}FN_3O_5S$]: calc: 489.1734 found: 489.1749

15. 5-(3,4-Dimethoxyphenyl)-4,4-dimethyl-2-(1-{[2-(trifluoromethoxy)phenyl]-sulfonyl}piperidin-4-yl)-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-(trifluoromethoxy)benzenesulfonyl chloride as starting compounds. The crude product is purified by crystallization from methanol to yield the title compound.

HRMS [$C_{25}H_{28}F_3N_3O_6S$]: calc: 555.1651 found: 555.1667

16. 2-{1-[(4-Chlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-chlorobenzenesulfonyl chloride as starting compounds. The crude product is purified by crystallization from methanol to yield the title compound.

HRMS [$C_{24}H_{28}ClN_3O_5S$]: calc: 505.1438 found: 505.1444

17. 5-(3,4-Dimethoxyphenyl)-4,4-dimethyl-2-[1-(naphthalen-2-ylsulfonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and naphthalene-2-sulfonyl chloride as starting compounds. The crude product is purified by crystallization from methanol to yield the title compound.

HRMS [$C_{28}H_{31}N_3O_5S$]: calc: 521.1984 found: 521.1984

18. 5-(3,4-Dimethoxyphenyl)-4,4-dimethyl-2-(1-{[2-(trifluoromethyl)phenyl]sulfonyl}piperidin-4-yl)-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-(trifluoromethyl)benzenesulfonyl chloride as starting compounds. The crude product is purified by crystallization from methanol to yield the title compound.

HRMS [$C_{25}H_{28}F_3N_3O_5S$]: calc: 539.1702 found: 539.1707

19. 5-(3,4-Dimethoxyphenyl)-4,4-dimethyl-2-{1-[(2,3,5,6-tetramethylphenyl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,3,5,6-tetramethylbenzenesulfonyl chloride as starting compounds. The crude product is purified by crystallization from methanol to yield the title compound.

HRMS [$C_{28}H_{37}N_3O_5S$]: calc: 527.2454 found: 527.2458

20. 2-{1-[(2-Bromophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-bromobenzenesulfonyl chloride as starting compounds. The crude product is purified by crystallization from methanol to yield the title compound.
HRMS [$C_{24}H_{28}BrN_3O_5S$]: calc: 549.0933 found: 549.0943

21. 2-{1-[(2,5-Dichlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,5-dichlorobenzenesulfonyl chloride as starting compounds. The crude product is purified by crystallization from methanol to yield the title compound.
HRMS [$C_{24}H_{27}Cl_2N_3O_5S$]: calc: 539.1048 found: 539.1044

22. 2-{1-[(2-Chlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-chlorobenzenesulfonyl chloride as starting compounds. The crude product is purified by crystallization from methanol to yield the title compound.
HRMS [$C_{24}H_{28}ClN_3O_5S$]: calc: 505.1438 found: 505.1454

23. 5-[3-(Cyclopropylmethoxy)-4-methoxyphenyl]-2-{1-[(2,6-dimethoxyphenyl)carbonyl]-piperidin-4-yl}-4,4-dimethyl-2,4-dihydro-3H-pyrazol-3-one Step 2: 1.1 g of 2-{1-[(2,6-dimethoxyphenyl)carbonyl]piperidin-4-yl}-5-(3-hydroxy-4-methoxyphenyl)-4,4-dimethyl-2,4-dihydro-3H-pyrazol-3-one (see below) and 0.95 g potassium carbonate are suspended in 20 ml of acetonitrile. 0.44 ml of (bromomethyl)cyclopropane are added and the reaction mixture is heated to reflux for about 16 h until the reaction is completed according to TLC analysis. The solvent is evaporated under reduced pressure, and the remaining residue is taken up in EA. The organic phase is washed with water, dried over $MgSO_4$, and the solvent is removed under reduced pressure. Purification of the resulting crude product by crystallization from EA yields the title compound.
HRMS [$C_{30}H_{37}N_3O_6$]: calc: 535.2682 found: 535.2677

Step 1: 2-{1-[(2,6-dimethoxyphenyl)carbonyl]piperidin-4-yl}-5-(3-hydroxy-4-methoxyphenyl)-4,4-dimethyl-2,4-dihydro-3H-pyrazol-3-one The title compound is prepared analogously as described for GP1 using 5-(3-hydroxy-4-methoxyphenyl)-4,4-dimethyl-2-piperidin-4-yl-2,4-dihydro-3H-pyrazol-3-one hydrochloride (compound B11*HCl) and 2,6-dimethoxybenzoyl chloride as starting compounds. The crude product is purified by crystallization from EA and diethyl ether to yield 2-{1-[(2,6-dimethoxyphenyl)carbonyl]piperidin-4-yl}-5-(3-hydroxy-4-methoxyphenyl)-4,4-dimethyl-2,4-dihydro-3H-pyrazol-3-one as the product.

24. Dimethyl 5-({4-[3-(3,4-dimethoxyphenyl)-4,4-dimethyl-5-oxo-4,5-dihydro-1H-pyrazol-1-yl]piperidin-1-yl}sulfonyl)isophthalate The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and dimethyl 5-(chlorosulfonyl)isophthalate as starting compounds. The crude product is purified by crystallization from EA and diethyl ether to yield the title compound.
M.p. 202° C.
HRMS [$C_{28}H_{33}N_3O_9S$]: calc: 587.1938 found: 587.1944

25. 3-({4-[3-(3,4-Dimethoxyphenyl)-4,4-dimethyl-5-oxo-4,5-dihydro-1H-pyrazol-1-yl]piperidin-1-yl}sulfonyl)benzoic acid The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 3-(chlorosulfonyl)benzoic acid as starting compounds. Instead of using the work-up procedure described for GP1, the following procedure is used. After the reaction has been quenched with 1 M aqueous sodium carbonate solution, the phases are separated and the aqueous phase is slightly acidified with aqueous hydrochloric acid.
The aqueous phase is extracted with DCM, the organic phase dried with $MgSO_4$ and the solvent is removed under reduced pressure to yield the title compound.
M.p. 244° C.
HRMS [$C_{25}H_{29}N_3O_7S$]: calc: 515.1726 found: 515.1732

26. Methyl 3-({4-[3-(3,4-dimethoxyphenyl)-4,4-dimethyl-5-oxo-4,5-dihydro-1H-pyrazol-1-yl]piperidin-1-yl}sulfonyl)benzoate 0.5 g 3-({4-[3-(3,4-Dimethoxyphenyl)-4,4-dimethyl-5-oxo-4,5-dihydro-1H-pyrazol-1-yl]piperidin-1-yl}sulfonyl)benzoic acid (compound described in example 25) are suspended in 20 ml of methanol, 0.2 ml concentrated sulfuric acid are added, and the reaction mixture is heated to reflux for 24 h. The solvent is removed under reduced pressure, the residue is taken up in DCM, the organic phase is washed with aqueous sodium carbonate solution (5%) and dried over $MgSO_4$. The solvents are evaporated under reduced pressure and the crude product is crystallized from DCM and diethyl ether to yield the title compound.
M.p. 214° C.
HRMS [$C_{26}H_{31}N_3O_7S$]: calc: 529.1883 found: 529.1897

27. 2-({4-[4-(3,4-Dimethoxyphenyl)-1-oxo-2,3-diazaspiro[4.4]non-3-en-2-yl]piperidin-1-yl}sulfonyl)benzonitrile The title compound is prepared analogously as described for GP1 using 4-(3,4-dimethoxyphenyl)-2-(piperidin-4-yl)-2,3-diazaspiro[4.4]non-3-en-1-one hydrochloride (compound B10*HCl) and 2-cyanobenzenesulfonyl chloride as starting compounds. The crude product is purified by crystallization from EA and diethyl ether to yield the title compound.
M.p. 174-176° C.
HRMS [$C_{27}H_{30}N_4O_5S$]: calc: 522.1937 found: 522.1949

28. 2-({4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}sulfonyl)benzonitrile The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 2-cyanobenzenesulfonyl chloride as starting compounds.

The crude product is purified by crystallization from methanol to yield the title compound.

HRMS [$C_{28}H_{32}N_4O_5S$]: calc: 536.2093 found: 536.2093

29. 5-(7-Methoxy-2,2-dimethyl-2,3-dihydro-1-benzofuran-4-yl)-4,4-dimethyl-2-[1-(quinolin-8-ylsulfonyl)piperidin-4-yl]-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and quinoline-8-sulfonyl chloride as starting compounds. The crude product is purified by crystallization from methanol to yield the title compound.

HRMS [$C_{30}H_{34}N_4O_5S$]: calc: 562.2250 found: 562.2260

30. 5-(7-Methoxy-2,2-dimethyl-2,3-dihydro-1-benzofuran-4-yl)-4,4-dimethyl-2-[1-(naphthalen-2-ylsulfonyl)piperidin-4-yl]-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and naphthalene-2-sulfonyl chloride as starting compounds. The crude product is purified by crystallization from methanol to yield the title compound.

HRMS [$C_{31}H_{35}N_3O_5S$]: calc: 561.2297 found: 561.2306

31. 2-{1-[(2-Fluorophenyl)sulfonyl]piperidin-4-yl}-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 2-fluorobenzenesulfonyl chloride as starting compounds. The crude product is purified by crystallization from methanol to yield the title compound.

HRMS [$C_{27}H_{32}FN_3O_5S$]: calc: 529.2047 found: 529.2058

32. 5-(7-Methoxy-2,2-dimethyl-2,3-dihydro-1-benzofuran-5-yl)-4,4-dimethyl-2-{1-[(3-methylphenyl)sulfonyl]piperidin-4-yl}-2,4-dihydro-3H-pyrazol-3-one The title compound is prepared analogously as described for GP1 using 5-(7-methoxy-2,2-dimethyl-2,3-dihydro-1-benzofuran-5-yl)-4,4-dimethyl-2-(piperidin-4-yl)-2,4-dihydro-3H-pyrazol-3-one (compound B12) and 3-methylbenzenesulfonyl chloride as starting compounds. The crude product is purified by chromatography (amino phase silica gel and DCM) and crystallization of the product containing fractions from DCM and diethyl ether to yield the title compound.

M.p. 183° C.

HRMS [$C_{28}H_{35}N_3O_5S$]: calc: 525.2297 found: 525.2314

33. 5-(3,4-Dimethoxyphenyl)-4,4-dimethyl-2-[1-(pyridin-2-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and pyridine-2-carboxylic acid as starting compounds. The crude product is purified by chromatography (amino phase silica gel and DCM) to yield the title compound.

M.p. 153° C.

HRMS [$C_{24}H_{28}N_4O_4$]: calc: 436.2111 found: 436.2112

34. 5-(3,4-Dimethoxyphenyl)-2-{1-[(2-methoxypyridin-3-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-methoxynicotinic acid as starting compounds. The crude product is purified by chromatography (amino phase silica gel and DCM) to yield the title compound.

HRMS [$C_{25}H_{30}N_4O_5$]: calc: 466.2216 found: 466.2221

35. 2-{1-[(3,5-Difluoropyridin-2-yl)carbonyl]piperidin-4-yl}-5-(3,4-dimethoxyphenyl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3,5-difluoropyridine-2-carboxylic acid as starting compounds. The crude product is purified by chromatography (amino phase silica gel and DCM) to yield the title compound.

HRMS [$C_{24}H_{26}F_2N_4O_4$]: calc: 472.1922 found: 472.1932

36. 5-(3,4-Dimethoxyphenyl)-4,4-dimethyl-2-{1-[(3-methylpyridin-2-yl)carbonyl]piperidin-4-yl}-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-methylpyridine-2-carboxylic acid as starting compounds. The crude product is purified by chromatography (amino phase silica gel and DCM) to yield the title compound.

HRMS [$C_{25}H_{30}N_4O_4$]: calc: 450.2267 found: 450.2279

37. 5-(3,4-Dimethoxyphenyl)-4,4-dimethyl-2-[1-(quinolin-3-ylcarbonyl)piperidin-4-yl]-2,4-dihydro-3H-pyrazol-3-one The title compound is prepared analogously as described for GP2-WU1 using 5-(3,4-dimethoxyphenyl)-4,4-dimethyl-2-(piperidin-4-yl)-2,4-dihydro-3H-pyrazol-3-one (compound B1) and quinoline-3-carboxylic acid as starting compounds.

M.p. 199° C.

HRMS [$C_{28}H_{30}N_4O_4$]: calc: 486.2267 found: 486.2274

38. 5-(3,4-Dimethoxyphenyl)-2-{1-[(2,6-dimethoxypyridin-3-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2,6-dimethoxynicotinic acid as starting compounds. The crude product is purified by chromatography (silica gel and DCM/diethyl ether/methanol=7:3:2) to yield the title compound.

HRMS [$C_{26}H_{32}N_4O_6$]: calc: 496.2322 found: 496.2323

39. 5-(3,4-Dimethoxyphenyl)-4,4-dimethyl-2-[1-(quinolin-2-ylcarbonyl)piperidin-4-yl]-2,4-dihydro-3H-pyrazol-3-one The title compound is prepared analogously as described for GP2-WU1 using 5-(3,4-dimethoxyphenyl)-4,4-dimethyl-2-(piperidin-4-yl)-2,4-dihydro-3H-pyrazol-3-one (compound B1) and quinoline-2-carboxylic acid as starting compounds. The crude product is purified by chromatography (silica gel and DCM/diethyl ether/methanol=49:49:3) to yield the title compound.

HRMS [$C_{28}H_{30}N_4O_4$]: calc: 486.2267 found: 486.2272

40. 5-[3-(Cyclopropylmethoxy)-4-methoxyphenyl]-2-{1-[(2-methoxyphenyl)carbonyl]-piperidin-4-yl}-4,4-dimethyl-2,4-dihydro-3H-pyrazol-3-one Step 2: 1.0 g of 5-(3-hydroxy-4-methoxyphenyl)-2-{1-[(2-methoxyphenyl)carbonyl]piperidin-4-yl}-4,4-dimethyl-2,4-dihydro-3H-pyrazol-3-one (see below) and 0.92 g potassium carbonate are suspended in 20 ml of acetonitrile. 0.43 ml of (bromomethyl)cyclopropane are added and the reaction mixture is heated to reflux over night until the reaction is completed according to TLC analysis. The solvent is evaporated under reduced pressure, and the remaining residue is taken up in EA. The organic phase is washed with water, dried over MgSO$_4$, and the solvent is removed under reduced pressure. Purification of the resulting crude product by column chromatography (silica gel and EA/DCM=1:3) and by crystallization of the product containing fractions from EA and diethyl ether yields the title compound.

HRMS [$C_{29}H_{35}N_3O_5$]: calc: 505.2577 found: 505.2595

Step 1: 5-(3-hydroxy-4-methoxyphenyl)-2-{1-[(2-methoxyphenyl)carbonyl]piperidin-4-yl}-4,4-dimethyl-2,4-dihydro-3H-pyrazol-3-one The title compound is prepared analogously as described for GP1 using 5-(3-hydroxy-4-methoxyphenyl)-4,4-dimethyl-2-piperidin-4-yl-2,4-dihydro-3H-pyrazol-3-one hydrochloride (compound B11*HCl) and 2-methoxybenzoyl chloride as starting compounds. The crude product is purified by crystallization from EA and diethyl ether to yield 5-(3-hydroxy-4-methoxyphenyl)-2-{1-[(2-methoxyphenyl)carbonyl]piperidin-4-yl}-4,4-dimethyl-2,4-dihydro-3H-pyrazol-3-one as the product.

41. 5-(3,4-Dimethoxyphenyl)-4,4-dimethyl-2-[1-(1,8-naphthyridin-2-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1,8-naphthyridine-2-carboxylic acid as starting compounds. The crude product is purified by chromatography (silica gel and DCM/diethyl ether/methanol=49:49:3) to yield the title compound.

HRMS [$C_{27}H_{29}N_5O_4$]: calc: 487.2220 found: 487.2224

42. 2-[1-(3-Chloroisonicotinoyl)piperidin-4-yl]-5-(3,4-dimethoxyphenyl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-chloroisonicotinic acid as starting compounds. The crude product is purified by chromatography (silica gel and DCM/diethyl ether/methanol=10:10:1) to yield the title compound.

HRMS [$C_{24}H_{27}ClN_4O_4$]: calc: 470.1721 found: 470.1731

43. 5-(3,4-Dimethoxyphenyl)-4,4-dimethyl-2-(1-{[4-(trifluoromethyl)pyridin-3-yl]carbonyl}piperidin-4-yl)-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 4-(trifluoromethyl)nicotinic acid as starting compounds. The crude product is purified by chromatography (silica gel and DCM/diethyl ether/methanol=10:12:1) to yield the title compound.

HRMS [$C_{25}H_{27}F_3N_4O_4$]: calc: 504.1984 found: 504.1991

44. 5-(3,4-Dimethoxyphenyl)-4,4-dimethyl-2-[1-(1,6-naphthyridin-5-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1,6-naphthyridine-5-carboxylic acid as starting compounds. The crude product is purified by chromatography (silica gel and DCM/methanol=95:5) to yield the title compound.

HRMS [$C_{27}H_{29}N_5O_4$]: calc: 487.2220 found: 487.2221

45. 5-(3,4-Dimethoxyphenyl)-4,4-dimethyl-2-[1-(quinoxalin-2-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoxaline-2-carboxylic acid as starting compounds. The crude product is purified by chromatography (amino phase silica gel and DCM) to yield the title compound.

HRMS [$C_{27}H_{29}N_5O_4$]: calc: 487.2220 found: 487.2230

46. 5-(3,4-Dimethoxyphenyl)-2-[1-(isoquinolin-1-ylcarbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and isoquinoline-1-carboxylic acid as starting compounds. The crude product is purified by chromatogra-

47. 2-{1-[3-(Cyclopropylmethoxy)-4-(difluoromethoxy)benzoyl]piperidin-4-yl}-5-(3,4-dimethoxyphenyl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-(cyclopropylmethoxy)-4-(difluoromethoxy)benzoic acid as starting compounds. The crude product is purified by chromatography (amino phase silica gel and DCM) to yield the title compound.

HRMS [$C_{30}H_{35}F_2N_3O_6$]: calc: 571.2494 found: 571.2499

48. 5-(3,4-Dimethoxyphenyl)-4,4-dimethyl-2-[1-(quinolin-8-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoline-8-carboxylic acid as starting compounds. The crude product is purified by chromatography (amino phase silica gel and DCM) to yield the title compound.

HRMS [$C_{28}H_{30}N_4O_4$]: calc: 486.2267 found: 486.2270

49. 5-(3,4-Dimethoxyphenyl)-4,4-dimethyl-2-[1-(2-piperidin-1-ylisonicotinoyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-piperidin-1-ylisonicotinic acid as starting compounds. The crude product is purified by chromatography (silica gel and DCM/diethyl ether=5:6) to yield the title compound.

HRMS [$C_{29}H_{37}N_5O_4$]: calc: 519.2846 found: 519.2851

50. 5-(3,4-Dimethoxyphenyl)-4,4-dimethyl-2-[1-(quinolin-4-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoline-4-carboxylic acid as starting compounds. The crude product is purified by chromatography (silica gel and DCM/diethyl ether/methanol=5:5:1) to yield the title compound.

HRMS [$C_{28}H_{30}N_4O_4$]: calc: 486.2267 found: 486.2278

51. 5-(3,4-Dimethoxyphenyl)-4,4-dimethyl-2-[1-(2-morpholin-4-ylisonicotinoyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-morpholin-4-ylisonicotinic acid as starting compounds. The crude product is purified by chromatography (silica gel and DCM/methanol=95:5) to yield the title compound.

HRMS [$C_{28}H_{35}N_5O_5$]: calc: 521.2638 found: 521.2654

52. 5-(3,4-Dimethoxyphenyl)-2-[1-(isoquinolin-5-ylcarbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and isoquinoline-5-carboxylic acid as starting compounds. The crude product is purified by chromatography (amino phase silica gel and DCM) and by crystallization from DCM and diethyl ether to yield the title compound.

M.p 210° C.

HRMS [$C_{28}H_{30}N_4O_4$]: calc: 486.2267 found: 486.2276

53. 5-(3,4-Dimethoxyphenyl)-4,4-dimethyl-2-[1-(quinolin-5-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoline-5-carboxylic acid as starting compounds. The crude product is purified by chromatography (amino phase silica gel and DCM) to yield the title compound.

HRMS [$C_{28}H_{30}N_4O_4$]: calc: 486.2267 found: 486.2283

54. 5-(3,4-Dimethoxyphenyl)-4,4-dimethyl-2-[1-(quinolin-7-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoline-7-carboxylic acid as starting compounds. The crude product is purified by chromatography (amino phase silica gel and DCM) and by crystallization from DCM and diethyl ether to yield the title compound.

M.p. 234° C.

HRMS [$C_{28}H_{30}N_4O_4$]: calc: 486.2267 found: 486.2267

55. 5-(3,4-Dimethoxyphenyl)-4,4-dimethyl-2-[1-(quinolin-6-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and quinoline-6-carboxylic acid as starting compounds. The crude product is purified by chromatography (amino phase silica gel and DCM) and by crystallization from DCM and diethyl ether to yield the title compound.

M.p. 203° C.

HRMS [$C_{28}H_{30}N_4O_4$]: calc: 486.2267 found: 486.2274

56. 5-(3,4-Dimethoxyphenyl)-2-[1-(isoquinolin-4-ylcarbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and isoquinoline-4-carboxylic acid as starting compounds. The crude product is purified by chromatography (amino phase silica gel and DCM/Methanol=97:3) to yield the title compound.

HRMS [$C_{28}H_{30}N_4O_4$]: calc: 486.2267 found: 486.2280

57. 5-(3,4-Dimethoxyphenyl)-2-[1-(1H-indol-5-yl-carbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1H-indole-5-carboxylic acid as starting compounds. The crude product is purified by chromatography (amino phase silica gel and DCM) and by crystallization from DCM and diethyl ether to yield the title compound.

M.p>270° C.

HRMS [$C_{27}H_{30}N_4O_4$]: calc: 474.2267 found: 474.2279

58. 5-(3,4-Dimethoxyphenyl)-2-[1-(1H-indol-6-yl-carbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1H-indole-6-carboxylic acid as starting compounds. The crude product is purified by chromatography (amino phase silica gel and DCM) and by crystallization from DCM and diethyl ether to yield the title compound.

M.p 247° C.

HRMS [$C_{27}H_{30}N_4O_4$]: calc: 474.2267 found: 474.2262

59. 5-(3,4-Dimethoxyphenyl)-2-[1-(1H-indol-4-yl-carbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1H-indole-4-carboxylic acid as starting compounds. The crude product is purified by chromatography (amino phase silica gel and DCM) and by crystallization from DCM and diethyl ether to yield the title compound.

M.p 235° C.

HRMS [$C_{27}H_{30}N_4O_4$]: calc: 474.2267 found: 474.2262

60. 5-(3,4-Dimethoxyphenyl)-2-[1-(1H-indol-7-yl-carbonyl)piperidin-4-yl]-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1H-indole-7-carboxylic acid as starting compounds. The crude product is purified by chromatography (amino phase silica gel and DCM) and by crystallization from DCM and diethyl ether to yield the title compound.

M.p 234° C.

HRMS [$C_{27}H_{30}N_4O_4$]: calc: 474.2267 found: 474.2276

61. 5-(3,4-Dimethoxyphenyl)-2-[1-(1H-indol-2-yl-carbonyl)piperidin-4-yl]-4,4-dimethyl-2,4-dihydro-3H-pyrazol-3-one The title compound is prepared analogously as described for GP2-WU1 using 5-(3,4-dimethoxyphenyl)-4,4-dimethyl-2-(piperidin-4-yl)-2,4-dihydro-3H-pyrazol-3-one (compound B1) and 1H-indole-2-carboxylic acid as starting compounds. The crude product is treated with DMF, the solids are removed by filtration, and the solvent is removed under reduces pressure. The resulting solid is purified by crystallization from DCM and diethyl ether to yield the title compound.

M.p. 265° C.

HRMS [$C_{27}H_{30}N_4O_4$]: calc: 474.2267 found: 474.2278

62. 5-(3,4-Dimethoxyphenyl)-4,4-dimethyl-2-{(1-[(2,4,6-trichlorophenyl)carbonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,4,6-trichlorobenzoyl chloride as starting compounds. The crude product is purified by crystallization from EA and diethyl ether to yield the title compound.

M.p. 155-159° C.

HRMS [$C_{25}H_{26}Cl_3N_3O_4$]: calc: 537.0989 found: 537.0977

63. 5-(3,4-Dimethoxyphenyl)-4,4-dimethyl-2-[1-(phenylcarbonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and benzoyl chloride as starting compounds. The crude product is purified by crystallization from EA and diethyl ether to yield the title compound.

M.p. 199-201° C.

HRMS [$C_{25}H_{29}N_3O_4$]: calc: 435.2158 found: 435.2156

64. 5-(3,4-Dimethoxyphenyl)-2-{1-[(2,4-dimethoxyphenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,4-dimethoxybenzoyl chloride as starting compounds. The crude product is purified by column chromatography (silica gel and EA/PE=2:1) to yield the title compound.

M.p. 206-208° C.

HRMS [$C_{27}H_{33}N_3O_6$]: calc: 495.2369 found: 495.2389

65. 5-(3,4-Dimethoxyphenyl)-2-{1-[(3-methoxyphenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-methoxybenzoyl chloride as starting compounds. The crude product is purified by crystallization from EA to yield the title compound.

HRMS [$C_{26}H_{31}N_3O_5$]: calc: 465.2264 found: 465.2267

66. 5-(3,4-Dimethoxyphenyl)-2-{1-[(3-fluorophenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-fluorobenzoyl chloride as starting compounds. The crude product is purified by crystallization from EA to yield the title compound.

HRMS [$C_{25}H_{28}FN_3O_4$]: calc: 453.2064 found: 453.2064

67. 5-(3,4-Dimethoxyphenyl)-2-{1-[(4-methoxyphenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-methoxybenzoyl chloride as starting compounds. The crude product is purified by crystallization from EA to yield the title compound.

HRMS [$C_{26}H_{31}N_3O_5$]: calc: 465.2264 found: 465.2274

68. 5-(3,4-Dimethoxyphenyl)-4,4-dimethyl-2-[1-(naphthalen-1-ylcarbonyl)piperidin-4-yl]-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 1-naphthoyl chloride as starting compounds. The crude product is purified by crystallization from EA to yield the title compound.

HRMS [$C_{29}H_{31}N_3O_4$]: calc: 485.2315 found: 485.2323

69. 2-{1-[(3-Chlorophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-chlorobenzoyl chloride as starting compounds. The crude product is purified by crystallization from EA to yield the title compound.

HRMS [$C_{25}H_{28}ClN_3O_4$]: calc: 469.1768 found: 469.1757

70. 5-(3,4-Dimethoxyphenyl)-2-{1-[(3-ethoxyphenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-ethoxybenzoyl chloride as starting compounds. The crude product is purified by column chromatography (silica gel and EA) and crystallization of the product containing fractions from EA and diethyl ether to yield the title compound.

M.p. 154-156° C.
HRMS [$C_{27}H_{33}N_3O_5$]: calc: 479.2420 found: 479.2430

71. 2-{1-[(4-Bromophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 4-bromobenzoyl chloride as starting compounds. The crude product is purified by crystallization from EA and diethyl ether to yield the title compound.

HRMS [$C_{25}H_{28}BrN_3O_4$]: calc: 513.1263 found: 513.1272

72. 2-{1-[(2-Bromophenyl)carbonyl]piperidin-4-yl}-5-(3,4-dimethoxyphenyl)-4,4-dimethyl-2,4-dihydro-3H-pyrazol-3-one The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 2-bromobenzoic acid as starting compounds. The crude product is purified by crystallization from methanol to yield the title compound.

HRMS [$C_{25}H_{28}BrN_3O_4$]: calc: 513.1263 found: 513.1270

73. 2-(1-{[4-Amino-3-(trifluoromethyl)phenyl]carbonyl}piperidin-4-yl)-5-(3,4-dimethoxyphenyl)-4,4-dimethyl-2,4-dihydro-3H-pyrazol-3-one The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 4-amino-3-(trifluoromethyl)benzoic acid as starting compounds. The crude product is purified by column chromatography (silica gel and DCM/methanol=4:1) and crystallization from methanol to yield the title compound.

HRMS [$C_{26}H_{29}F_3N_4O_4$]: calc: 518.2141 found: 518.2145

74. 4-({4-[3-(3,4-Dimethoxyphenyl)-4,4-dimethyl-5-oxo-4,5-dihydro-1H-pyrazol-1-yl]piperidin-1-yl}carbonyl)phenyl acetate The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 4-(acetyloxy)benzoic acid as starting compounds. The crude product is purified by crystallization from methanol to yield the title compound.

HRMS [$C_{27}H_{31}N_3O_6$]: calc: 493.2213 found: 493.2225

75. 5-(7-Methoxy-2,2-dimethyl-2,3-dihydro-1-benzofuran-4-yl)-2-{1-[(2-methoxyphenyl)carbonyl]piperidin-4-yl}-4,4-dimethyl-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 2-methoxybenzoyl chloride as starting compounds. The crude product is purified by crystallization from EA and diethyl ether to yield the title compound.

HRMS [$C_{29}H_{35}N_3O_5$]: calc: 505.2577 found: 505.2596

76. 5-(3,4-Dimethoxyphenyl)-2-{1-[(3-hydroxyphenyl)carbonyl]piperidin-4-yl}-4,4-dimethyl-2,4-dihydro-3H-pyrazol-3-one 10 g 3-({4-[3-(3,4-dimethoxyphenyl)-4,4-dimethyl-5-oxo-4,5-dihydro-1H-pyrazol-1-yl]piperidin-1-yl}carbonyl) phenyl acetate (compound described in example 12) are dissolved in a mixture of 200 ml THF, 100 ml acetone and 200 ml of methanol. To this mixture 200 ml of 2 M methanolic sodium hydroxide solution are added, and the reaction mixture is stirred at RT for 1 h until the reaction is completed according to TLC analysis. The reaction mixture is acidified with concentrated aqueous hydrochloric acid, and the solvents are largely removed under reduced pressure, while the crude product is precipitating. The solids are collected and washed with water to yield the title compound.

HRMS [$C_{25}H_{29}N_3O_5$]: calc: 451.2107 found: 451.2125

77. 2-({4-[3-(7-Methoxy-2,2-dimethyl-2,3-dihydro-1-benzofuran-4-yl)-4,4-dimethyl-5-oxo-4,5-dihydro-1H-pyrazol-1-yl]piperidin-1-yl}carbonyl)phenyl acetate The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 2-(chlorocarbonyl)phenyl acetate as starting compounds. The crude product is purified by crystallization from EA and diethyl ether to yield the title compound.

HRMS [$C_{30}H_{35}N_3O_6$]: calc: 533.2526 found: 533.2530

78. 2-[1-(2-Hydroxybenzoyl)piperidin-4-yl]-5-(7-methoxy-2,2-dimethyl-2,3-dihydro-1-benzofuran-4-yl)-4,4-dimethyl-2,4-dihydro-3H-pyrazol-3-one 0.15 g 2-({4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}carbonyl)phenyl acetate (compound described in example 77) are dissolved in 20 ml of methanol, 0.32 ml 1 M methanolic potassium hydroxide solution are added, and the reaction mixture is stirred at RT for 15 min until the reaction is completed according to TLC analysis. The pH is adjusted to 5.5 with 1 M aqueous hydrochloric acid, the solvents are removed under reduced pressure, and the resulting crude product is purified by column chromatography (silica and DCM/methanol=95:5) to yield the title compound.

HRMS [$C_{28}H_{33}N_3O_5$]: calc: 491.2420 found: 491.2431

79. 2-(1-{[5-(Benzyloxy)-2-chlorophenyl]carbonyl}piperidin-4-yl)-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 5-(benzyloxy)-2-chlorobenzoyl chloride (compound F3) as starting compounds. The crude product is purified by crystallization from EA and diethyl ether to yield the title compound.

HRMS [$C_{32}H_{34}ClN_3O_5$]: calc: 575.2187 found: 575.2197

80/81. 2-(1-{[2-Chloro-5-(propan-2-yloxy)phenyl]carbonyl}piperidin-4-yl)-5-(3,4-dimethoxyphenyl)-4,4-dimethyl-2,4-dihydro-3H-pyrazol-3-one and 5-(3,4-dimethoxyphenyl)-4,4-dimethyl-2-(1-{[3-(propan-2-yloxy)phenyl]carbonyl}piperidin-4-yl)-2,4-dihydro-3H-pyrazol-3-one Step 2: 0.3 g of the mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one (see below) and 0.25 g potassium carbonate are suspended in 5 ml of acetonitrile. 0.18 ml of 2-iodopropane are added and the reaction mixture is heated to reflux under a blanket of nitrogen for about 16 h until the reaction is completed according to TLC analysis. The solvent is evaporated under reduced pressure, and the remaining residue is taken up in EA. The organic phase is washed with water, twice with 1 M aqueous sodium hydroxide solution and brine. The organic phase is dried over $MgSO_4$, and the solvent is removed under reduced pressure. Purification of the resulting crude product by column chromatography (silica gel and EA) yields the two title compounds as isolated fractions (F1 and F2).

F1: HRMS [$C_{28}H_{34}ClN_3O_5$]: calc: 527.2187 found: 527.2195

F2: HRMS [$C_{28}H_{35}N_3O_5$]: calc: 493.2577 found: 493.2569

Step 1: Mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one Under a blanket of nitrogen 5.08 g of 2-(1-{[5-(benzyloxy)-2-chlorophenyl]carbonyl}piperidin-4-yl)-5-(3,4-dimethoxyphenyl)-4,4-dimethyl-2,4-dihydro-3H-pyrazol-3-one (compound described in example 79) are dissolved in 20 ml of methanol and 0.53 g palladium on charcoal (10%) and 2.81 g ammonium formiate are added. The reaction mixture is heated to reflux or 45 min until the starting material is consumed according to TLC analysis. The mixture is filtered over a plug of celite, and the solvent is removed under reduced pressure resulting in the crude product, which is taken up in EA and washed tree times with water. Crystallization from EA results in a mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one as the product.

HRMS [$C_{25}H_{28}ClN_3O_5$ and $C_{25}H_{29}N_3O_5$]: calc: 485.1717 and 451.2107 found: 485.1733 and 451.2118

82. Ethyl [4-chloro-3-({4-[3-(3,4-dimethoxyphenyl)-4,4-dimethyl-5-oxo-4,5-dihydro-1H-pyrazol-1-yl]piperidin-1-yl}carbonyl)phenoxy]acetate Step 2: 2.1 g of the mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one (see below) and 1.2 g potassium carbonate are suspended in 75 ml of DMF. 0.76 ml of ethyl bromoacetate are added and the reaction mixture is heated to 50° C. under a blanket of nitrogen over night until the reaction is completed according to TLC analysis. The solvent is evaporated under reduced pressure, and the remaining residue is taken up in EA. The organic phase is washed with water three times, dried over $MgSO_4$, and the solvent is removed under reduced pressure. Purification of the resulting crude product by column chromatography (silica gel and EA) yields the title compound.

HRMS [$C_{29}H_{34}ClN_3O_7$]: calc: 571.2085 found: 571.2102

Step 1: Mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one Under a blanket of nitrogen 5.08 g of 2-(1-{[5-(benzyloxy)-2-chlorophenyl]carbonyl}piperidin-4-yl)-5-(3,4- dimethoxyphenyl)-4,4-dimethyl-2,4-dihydro-3H-pyrazol-3-one (compound described in example 79) are dissolved in 20 ml of methanol and 0.53 g palladium on charcoal (10%) and 2.81 g ammonium formiate are added. The reaction mixture is heated to reflux or 45 min until the starting material is consumed according to TLC analysis. The mixture is filtered over a plug of celite, and the solvent is removed under reduced pressure resulting in the crude product, which is taken up in EA and washed tree times with water. Crystallization from EA results in a mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one as the product.

HRMS [$C_{25}H_{28}ClN_3O_5$ and $C_{25}H_{29}N_3O_5$]: calc: 485.1717 and 451.2107 found: 485.1733 and 451.2118

84. 2-(1-{[5-(Benzyloxy)-2-methylphenyl]carbonyl}piperidin-4-yl)-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 5-(benzyloxy)-2-methylbenzoyl chloride (compound F2) as starting compounds. The crude product is purified by crystallization from EA and diethyl ether to yield the title compound.

M.p. 142-145° C.
HRMS [$C_{33}H_{37}N_3O_5$]: calc: 555.2733 found: 555.2724

85. 5-(3,4-Dimethoxyphenyl)-2-{1-[(5-hydroxy-2-methylphenyl)carbonyl]piperidin-4-yl}-4,4-dimethyl-2,4-dihydro-3H-pyrazol-3-one Under a blanket of nitrogen 4.0 g of 2-(1-{[5-(benzyloxy)-2-methylphenyl]carbonyl}piperidin-4-yl)-5-(3,4-dimethoxyphenyl)-4,4-dimethyl-2,4-dihydro-3H-pyrazol-3-one (compound described in example 84) are dissolved in 80 ml of methanol and 0.4 g palladium on charcoal (10%) and 2.25 g ammonium formiate are added. The reaction mixture is heated to reflux or 20 min until the starting material is consumed according to TLC analysis. The mixture is filtered over a plug of celite, and the solvent is removed under reduced pressure resulting in the crude product, which is taken up in EA and washed twice with water and with brine. Crystallization from EA and PE results in the title compound.

M.p. 214-215° C.
HRMS [$C_{26}H_{31}N_3O_5$]: calc: 465.2264 found: 465.2276

86. Ethyl [3-({4-[3-(3,4-dimethoxyphenyl)-4,4-dimethyl-5-oxo-4,5-dihydro-1H-pyrazol-1-yl]piperidin-1-yl}carbonyl)-4-methylphenoxy]acetate 0.5 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 0.3 g potassium carbonate are suspended in 20 ml of DMF. 0.2 ml of ethyl bromoacetate is added and the reaction mixture is heated to 50° C. under a blanket of nitrogen for about 16 h until the reaction is completed according to TLC analysis. The solvent is evaporated under reduced pressure, and the remaining residue is taken up in EA. The organic phase is washed twice with water and brine, dried over MgSO$_4$, and the solvent is removed under reduced pressure.

Purification of the resulting crude product by crystallization from diethyl ether yields the title compound.
HRMS [$C_{30}H_{37}N_3O_7$]: calc: 551.2632 found: 551.2639

87. 5-(3,4-Dimethoxyphenyl)-4,4-dimethyl-2-(1-{[2-methyl-5-(propan-2-yloxy)phenyl]carbonyl}piperidin-4-yl)-2,4-dihydro-3H-pyrazol-3-one 0.28 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 0.25 g potassium carbonate are suspended in 5 ml of acetonitrile. 0.31 g of 2-iodopropane is added and the reaction mixture is heated to reflux under a blanket of nitrogen for about 16 h until the reaction is completed according to TLC analysis. The solvent is evaporated under reduced pressure, and the remaining residue is taken up in EA. The organic phase is washed with water, twice with 1 M aqueous sodium hydroxide solution and with brine, dried over MgSO$_4$, and the solvent is removed under reduced pressure. Purification of the resulting crude product by crystallization from diethyl ether yields the title compound.
HRMS [$C_{29}H_{37}N_3O_5$]: calc: 507.2733 found: 507.2737

88. 2-(1-{[5-(Benzyloxy)-2-methylphenyl]carbonyl}piperidin-4-yl)-5-(7-methoxy-2,2-dimethyl-2,3-dihydro-1-benzofuran-5-yl)-4,4-dimethyl-2,4-dihydro-3H-pyrazol-3-one The title compound is prepared analogously as described for GP2-WU2 using 5-(7-methoxy-2,2-dimethyl-2,3-dihydro-1-benzofuran-5-yl)-4,4-dimethyl-2-(piperidin-4-yl)-2,4-dihydro-3H-pyrazol-3-one (compound B12) and 5-(benzyloxy)-2-methylbenzoic acid (compound F1) as starting compounds. The crude product is purified by chromatography (amino phase silica gel and DCM) to yield the title compound.
HRMS [$C_{36}H_{41}N_3O_5$]: calc: 595.3046 found: 595.3043

89. 2-{1-[(5-Hydroxy-2-methylphenyl)carbonyl]piperidin-4-yl}-5-(7-methoxy-2,2-dimethyl-2,3-dihydro-1-benzofuran-5-yl)-4,4-dimethyl-2,4-dihydro-3H-pyrazol-3-one Under a blanket of nitrogen 0.3 g of 2-(1-{[5-(benzyloxy)-2-methylphenyl]carbonyl}piperidin-4-yl)-5-(7-methoxy-2,2-dimethyl-2,3-dihydro-1-benzofuran-5-yl)-4,4-dimethyl-2,4-dihydro-3H-pyrazol-3-one (compound described in example 88) are dissolved in 20 ml of methanol and 0.04 g palladium on charcoal (10%) and 0.32 g ammonium formiate are added. The reaction mixture is heated to reflux or 4 h until the starting material is consumed according to TLC analysis. The mixture is filtered over a plug of celite, and the solvent is removed under reduced pressure resulting in the crude product, which is purified by column chromatography (amino phase silica gel and DCM) to yield the title compound.
HRMS [$C_{29}H_{35}N_3O_5$]: calc: 505.2577 found: 505.2578

90. 5-(3,4-Dimethoxyphenyl)-2-{1-[(2-fluoro-5-hydroxyphenyl)carbonyl]piperidin-4-yl}-4,4-dimethyl-2,4-dihydro-3H-pyrazol-3-one Step 2: 0.51 g of 5-(3,4-dimethoxyphenyl)-2-(1-{[2-fluoro-5-(methoxymethoxy)phenyl]carbonyl}piperidin-4-yl)-4,4-dimethyl-2,4-dihydro-3H-pyrazol-3-one (see below) are solved in 25 ml of anhydrous methanol. Under a blanket of nitrogen 0.25 ml boron trifluoride diethyl etherate are added portion wise while the reaction mixture is stirred for three days until the reaction is complete according to TLC analysis. The volatiles are removed under reduced pressure resulting in the crude product, which is purified by crystallization from methanol yielding the title compound.

HRMS [$C_{25}H_{28}FN_3O_5$]: calc: 469.2013 found: 469.2006

Step 1: 5-(3,4-Dimethoxyphenyl)-2-(1-{[2-fluoro-5-(methoxymethoxy)phenyl]carbonyl}piperidin-4-yl)-4,4-dimethyl-2,4-dihydro-3H-pyrazol-3-one To a solution of 4.5 g 5-(3,4-dimethoxyphenyl)-4,4-dimethyl-2-(piperidin-4-yl)-2,4-dihydro-3H-pyrazol-3-one hydrochloride (compound B1*HCl) in 60 ml of DCM a solution of 2.4 g 2-fluoro-5-(methoxymethoxy)benzoic acid 20 ml of DCM, 1.7 ml TEA, 1.7 g HOBt and 2.4 g EDCi*HCl are added. The reaction mixture is stirred for 90 min until the reaction is complete according to TLC analysis. The reaction mixture is quenched with 1 M aqueous hydrochloric acid, the phases are separated and the organic phase is washed with 1 M aqueous hydrochloric acid again, with water, twice with 1M aqueous sodium carbonate solution and with brine. The organic phase is dried over MgSO$_4$, and the solvent is removed under reduced pressure resulting in a crude product, which is purified by crystallization from diethyl ether to yield 5-(3,4-dimethoxyphenyl)-2-(1-{[2-fluoro-5-(methoxymethoxy)phenyl]carbonyl}piperidin-4-yl)-4,4-dimethyl-2,4-dihydro-3H-pyrazol-3-one as the product.

91. 2-{1-[(5-Amino-2-chlorophenyl)carbonyl]piperidin-4-yl}-5-(3,4-dimethoxyphenyl)-4,4-dimethyl-2,4-dihydro-3H-pyrazol-3-one Step 2: 0.51 g of 2-{1-[(2-chloro-5-nitrophenyl)carbonyl]piperidin-4-yl}-5-(3,4-dimethoxyphenyl)-4,4-dimethyl-2,4-dihydro-3H-pyrazol-3-one (see below) are solved in 15 ml of EA, and 0.05 g palladium of charcoal (5%) are added. The reaction mixture is stirred for about 16 h at RT under an atmosphere of hydrogen until the reaction is completed according to TLC analysis. The mixture is filtered over a plug of celite, and the solvent is removed under reduced pressure resulting in the crude product, which is purified by crystallization from EA and by column chromatography (silica gel and EA/DCM=9:1) yielding the title compound.

HRMS [$C_{25}H_{29}ClN_4O_4$]: calc: 484.1877 found: 484.1887

Step 1: 2-{1-[(2-chloro-5-nitrophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-chloro-5-nitrobenzoyl chloride as starting compounds. The crude product is purified by column chromatography (silica gel and DCM/EA=1:1) and by crystallization from EA and diethyl ether to yield 2-{1-[(2-chloro-5-nitrophenyl)carbonyl]piperidin-4-yl}-5-(3,4-dimethoxyphenyl)-4,4-dimethyl-2,4-dihydro-3H-pyrazol-3-one as the product.

92. N-[4-chloro-3-({4-[3-(3,4-dimethoxyphenyl)-4,4-dimethyl-5-oxo-4,5-dihydro-1H-pyrazol-1-yl]piperidin-1-yl}carbonyl)phenyl]acetamide 0.18 g of 2-{1-[(5-amino-2-chlorophenyl)carbonyl]piperidin-4-yl}-5-(3,4-dimethoxyphenyl)-4,4-dimethyl-2,4-dihydro-3H-pyrazol-3-one (compound described in example 91) are dissolved in 5 ml of DCM, 0.17 ml TEA and 0.032 ml acetyl chloride are added, and the reaction mixture is stirred at RT for about 16 h until the reaction is completed according to TLC analysis. The mixture is washed with 0.5 M aqueous sulfuric acid, twice with 1 M aqueous sodium carbonate solution and with brine. The organic phase is dried over MgSO$_4$, and the solvent is removed under reduced pressure resulting in the crude product, which is purified by column chromatography (silica gel and EA) yielding the title compound.

HRMS [$C_{27}H_{31}ClN_4O_5$]: calc: 526.1983 found: 526.1993

93. 2-({4-[3-(3,4-Dimethoxyphenyl)-4,4-dimethyl-5-oxo-4,5-dihydro-1H-pyrazol-1-yl]piperidin-1-yl}carbonyl)phenyl acetate The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-(chlorocarbonyl)phenyl acetate as starting compounds. The crude product is purified by crystallization from EA and diethyl ether to yield the title compound.

HRMS [$C_{27}H_{31}N_3O_6$]: calc: 493.2213 found: 493.2221

94. 5-(3,4-Dimethoxyphenyl)-2-{1-[(2-hydroxyphenyl)carbonyl]piperidin-4-yl}-4,4-dimethyl-2,4-dihydro-3H-pyrazol-3-one 17 g 2-({4-[3-(3,4-Dimethoxyphenyl)-4,4-dimethyl-5-oxo-4,5-dihydro-1H-pyrazol-1-yl]piperidin-1-yl}carbonyl)phenyl acetate (compound described in example 93) are dissolved in 200 ml THF, 200 ml of 2 M methanolic sodium hydroxide solution are added, and the reaction mixture is stirred at RT for 1 h until the reaction is completed according to TLC analysis. The reaction mixture is acidified with concentrated aqueous hydrochloric acid, and the solvents are largely removed under reduced pressure, while the crude product is precipitating. The solids are collected and washed with water to yield the title compound.

M.p. 212-213° C.

HRMS [$C_{25}H_{29}N_3O_5$]: calc: 451.2107 found: 451.2119

95. 5-(3,4-Dimethoxyphenyl)-4,4-dimethyl-2-(1-{[3-(2,2,2-trifluoroethoxy)phenyl]-carbonyl}piperidin-4-yl)-2,4-dihydro-3H-pyrazol-3-one 0.8 g of 5-(3,4-dimethoxyphenyl)-2-{1-[(3-hydroxyphenyl)carbonyl]piperidin-4-yl}-4,4-dimethyl-2,4-dihydro-3H-pyrazol-3-one (compound described in example 76) and 0.75 g potassium carbonate are suspended in 10 ml of DMF. 0.4 g of 1,1,1-trifluoro-2-iodoethane are added and the reaction mixture is heated to 100° C. for 8 h until the reaction is completed according to TLC analysis. The solvent is evaporated under reduced pressure, and the remaining residue is taken up in DCM. The organic phase is washed with water, dried over MgSO$_4$, and the solvent is removed under reduced pressure. Purification of the resulting crude product by column chromatography (silica gel and EA/PE/TEA=10:10:1) and by crystallization from diethyl ether yields the title compound.

HRMS [$C_{27}H_{30}F_3N_3O_5$]: calc: 533.2138 found: 533.2141

96. 2-(1-{[2-(Cyclopentyloxy)phenyl]carbonyl}piperidin-4-yl)-5-(3,4-dimethoxyphenyl)-4,4-dimethyl-2,4-dihydro-3H-pyrazol-3-one 1.0 g of 5-(3,4-dimethoxyphenyl)-2-{1-[(2-hydroxyphenyl)carbonyl]piperidin-4-yl}-4,4-dimethyl-2,4-dihydro-3H- pyrazol-3-one (compound described in example 94) and 1.0 g potassium carbonate are suspended in 20 ml of acetonitrile. 0.5 g of iodocyclopentane are added and the reaction mixture is heated to reflux for 5 h until the reaction is completed according to TLC analysis. The solvent is evaporated under reduced pressure, and the remaining residue is taken up in EA. The organic phase is washed with water, dried over MgSO$_4$, and the solvent is removed under reduced pressure. Purification of the resulting crude product by crystallization from methanol yields the title compound.

M.p. 176° C.

HRMS [C$_{30}$H$_{37}$N$_3$O$_5$]: calc: 519.2733 found: 519.2736

97. 2-[2-({4-[3-(3,4-Dimethoxyphenyl)-4,4-dimethyl-5-oxo-4,5-dihydro-1H-pyrazol-1-yl]piperidin-1-yl}carbonyl)phenoxy]acetamide 1.0 g of 5-(3,4-dimethoxyphenyl)-2-{1-[(2-hydroxyphenyl)carbonyl]piperidin-4-yl}-4,4-dimethyl-2,4-dihydro-3H-pyrazol-3-one (compound described in example 94) and 1.0 g potassium carbonate are suspended in 20 ml of acetonitrile. 0.3 g of 2-chloroacetamide are added and the reaction mixture is heated to reflux for 5 h until the reaction is completed according to TLC analysis. The solvent is evaporated under reduced pressure, and the remaining residue is taken up in DCM. The organic phase is washed with water, dried over MgSO$_4$, and the solvent is removed under reduced pressure. Purification of the resulting crude product by crystallization from EA yields the title compound.

HRMS [C$_{27}$H$_{32}$N$_4$O$_6$]: calc: 508.2322 found: 508.2316

98. 5-(3,4-Dimethoxyphenyl)-4,4-dimethyl-2-(1-{[3-(trifluoromethyl)phenyl]sulfonyl}piperidin-4-yl)-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 3-(trifluoromethyl)benzenesulfonyl chloride as starting compounds. The crude product is purified by crystallization from EA and diethyl ether to yield the title compound.

HRMS [C$_{25}$H$_{28}$F$_3$N$_3$O$_5$S]: calc: 539.1702 found: 539.1705

99. 2-{1-[(5-Chloro-2-methoxyphenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 5-chloro-2-methoxybenzenesulfonyl chloride as starting compounds. The crude product is purified by crystallization from EA and diethyl ether to yield the title compound.

HRMS [C$_{25}$H$_{30}$ClN$_3$O$_6$S]: calc: 535.1544 found: 535.1547

100. 5-(3,4-Dimethoxyphenyl)-4,4-dimethyl-2-(1-{[4-(propan-2-yl)phenyl]sulfonyl}piperidin-4-yl)-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 4-(propan-2-yl)benzenesulfonyl chloride as starting compounds. The crude product is purified by crystallization from EA and diethyl ether to yield the title compound.

HRMS [C$_{27}$H$_{35}$N$_3$O$_5$S]: calc: 513.2297 found: 513.2297

101. 2-(1-{[2-Chloro-4-(trifluoromethyl)phenyl]sulfonyl}piperidin-4-yl)-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 2-chloro-4-(trifluoromethyl)benzenesulfonyl chloride as starting compounds. The crude product is purified by crystallization from EA and diethyl ether to yield the title compound.

HRMS [C$_{25}$H$_{27}$ClF$_3$N$_3$O$_5$S]: calc: 573.1312 found: 573.1314

103. 2-{1-[(2,3-Dichlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 2,3-dichlorobenzenesulfonyl chloride as starting compounds. The crude product is purified by crystallization from EA and diethyl ether to yield the title compound.

HRMS [C$_{24}$H$_{27}$Cl$_2$N$_3$O$_5$S]: calc: 539.1049 found: 539.1043

104. 2-{1-[(3,5-Dichlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 3,5-dichlorobenzenesulfonyl chloride as starting compounds. The crude product is purified by crystallization from EA and diethyl ether to yield the title compound.

HRMS [C$_{24}$H$_{27}$Cl$_2$N$_3$O$_5$S]: calc: 539.1049 found: 539.1042

105. 2-{1-[(2,6-Dichlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 2,6-dichlorobenzenesulfonyl chloride as starting compounds. The crude product is purified by crystallization from EA and diethyl ether to yield the title compound.

HRMS [C$_{24}$H$_{27}$Cl$_2$N$_3$O$_5$S]: calc: 539.1049 found: 539.1043

106. 2-{1-[(2,4-Dichlorophenyl)sulfonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 2,4-dichlorobenzenesulfonyl chloride as starting com-

107. 5-(3,4-Dimethoxyphenyl)-2-{1-[(4-fluoro-2-methylphenyl)sulfonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 4-fluoro-2-methylbenzenesulfonyl chloride as starting compounds. The crude product is purified by crystallization from EA and diethyl ether to yield the title compound.

HRMS [$C_{25}H_{30}FN_3O_5S$]: calc: 503.1890 found: 503.1891

108. 5-(3,4-Dimethoxyphenyl)-4,4-dimethyl-2-{1-[(1-methyl-1H-indol-4-yl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 1-methyl-1H-indole-4-sulfonyl chloride as starting compounds. The crude product is purified by crystallization from EA and diethyl ether to yield the title compound.

HRMS [$C_{27}H_{32}N_4O_5S$]: calc: 524.2093 found: 524.2091

109. 5-(3,4-Dimethoxyphenyl)-4,4-dimethyl-2-{1-[(1-methyl-1H-indol-5-yl)sulfonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one (compound B1) and 1-methyl-1H-indole-5-sulfonyl chloride as starting compounds. The crude product is purified by crystallization from EA and diethyl ether to yield the title compound.

HRMS [$C_{27}H_{32}N_4O_5S$]: calc: 524.2093 found: 524.2097

110. 5-(7-Methoxy-2,2-dimethyl-2,3-dihydro-1-benzofuran-4-yl)-4,4-dimethyl-2-{1-[(1-methyl-1H-indol-4-yl)sulfonyl]piperidin-4-yl}-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 1-methyl-1H-indole-4-sulfonyl chloride as starting compounds. The crude product is purified by crystallization from methanol to yield the title compound.

HRMS [$C_{30}H_{36}N_4O_5S$]: calc: 564.2406 found: 564.2409

111. 5-(7-Methoxy-2,2-dimethyl-2,3-dihydro-1-benzofuran-4-yl)-4,4-dimethyl-2-{1-[(3-methylphenyl)sulfonyl]piperidin-4-yl}-2,4-dihydro-3H-pyrazol-3-one The title compound is prepared analogously as described for GP1 using 5-(7-methoxy-2,2-dimethyl-2,3-dihydro-1-benzofuran-4-yl)-4,4-dimethyl-2-(piperidin-4-yl)-2,4-dihydro-3H-pyrazol-3-one hydrochloride (compound B5*HCl) and 3-methylbenzenesulfonyl chloride as starting compounds. The crude product is purified by crystallization from methanol to yield the title compound.

HRMS [$C_{28}H_{35}N_3O_5S$]: calc: 525.2297 found: 525.2298

112. 5-(7-Methoxy-3H-spiro[1-benzofuran-2,1'-cyclopentan]-4-yl)-4,4-dimethyl-2-{1-[(3-methylphenyl)sulfonyl]piperidin-4-yl}-2,4-dihydro-3H-pyrazol-3-one The title compound is prepared analogously as described for GP1 using 5-(7-methoxy-3H-spiro[1-benzofuran-2,1'-cyclopentan]-4-yl)-4,4-dimethyl-2-piperidin-4-yl-2,4-dihydro-3H-pyrazol-3-one hydrochloride (compound B6*HCl) and 3-methylbenzenesulfonyl chloride as starting compounds. The crude product is purified by crystallization from methanol to yield the title compound.

HRMS [$C_{30}H_{37}N_3O_5S$]: calc: 551.2454 found: 551.2449

113. 5-[3-(Cyclopropylmethoxy)-4-(difluoromethoxy)phenyl]-4,4-dimethyl-2-{1-[(3-methylphenyl)sulfonyl]piperidin-4-yl}-2,4-dihydro-3H-pyrazol-3-one The title compound is prepared analogously as described for GP1 using 5-[3-(cyclopropylmethoxy)-4-(difluoromethoxy)phenyl]-4,4-dimethyl-2-piperidin-4-yl-2,4-dihydro-3H-pyrazol-3-one hydrochloride (compound B3*HCl) and 3-methylbenzenesulfonyl chloride as starting compounds. The crude product is purified by crystallization from methanol to yield the title compound.

HRMS [$C_{28}H_{33}F_2N_3O_5S$]: calc: 561.2109 found: 561.2114

114. 5-(3,4-Diethoxyphenyl)-4,4-dimethyl-2-{1-[(3-methylphenyl)sulfonyl]piperidin-4-yl}-2,4-dihydro-3H-pyrazol-3-one The title compound is prepared analogously as described for GP1 using 5-(3,4-diethoxyphenyl)-4,4-dimethyl-2-piperidin-4-yl-2,4-dihydro-3H-pyrazol-3-one hydrochloride (compound B2*HCl) and 3-methylbenzenesulfonyl chloride as starting compounds. The crude product is purified by crystallization from methanol to yield the title compound.

HRMS [$C_{27}H_{35}N_3O_5S$]: calc: 513.2297 found: 513.2297

115. 4-(3,4-Dimethoxyphenyl)-2-{1-[(3-methylphenyl)sulfonyl]piperidin-4-yl}-2,3-diazaspiro[4.4]non-3-en-1-one The title compound is prepared analogously as described for GP1 using 4-(3,4-dimethoxyphenyl)-2-(piperidin-4-yl)-2,3-diazaspiro[4.4]non-3-en-1-one hydrochloride (compound B10*HCl) and 3-methylbenzenesulfonyl chloride as starting compounds. The crude product is purified by crystallization from EA and diethyl ether to yield the title compound.

HRMS [$C_{27}H_{33}N_3O_5S$]: calc: 511.2141 found: 511.2141

116. 5-(3,4-Dimethoxyphenyl)-4-ethyl-4-methyl-2-{1-[(3-methylphenyl)sulfonyl]piperidin-4-yl}-2,4-dihydro-3H-pyrazol-3-one The title compound is prepared analogously as described for GP1 using 5-(3,4-dimethoxyphenyl)-4-ethyl-4-methyl-2-piperidin-4-yl-2,4-dihydro-3H-pyrazol-3-one hydrochloride (compound B9*HCl) and 3-methylbenzenesulfonyl chloride as starting compounds. The crude product is purified by crystallization from methanol to yield the title compound.
HRMS [$C_{26}H_{33}N_3O_5S$]: calc: 499.2141 found: 499.2138

117. 5-(3,4-Dimethoxyphenyl)-4-methyl-2-{1-[(3-methylphenyl)sulfonyl]piperidin-4-yl}-4-propyl-2,4-dihydro-3H-pyrazol-3-one The title compound is prepared analogously as described for GP1 using 5-(3,4-dimethoxyphenyl)-4-methyl-2-piperidin-4-yl-4-propyl-2,4-dihydro-3H-pyrazol-3-one hydrochloride (compound B8*HCl) and 3-methylbenzenesulfonyl chloride as starting compounds. The crude product is purified by crystallization from methanol to yield the title compound.
HRMS [$C_{27}H_{35}N_3O_5S$]: calc: 513.2297 found: 513.2298

118. 5-(3,4-Dimethoxyphenyl)-4,4-diethyl-2-{1-[(3-methylphenyl)sulfonyl]piperidin-4-yl}-2,4-dihydro-3H-pyrazol-3-one The title compound is prepared analogously as described for GP1 using 5-(3,4-dimethoxyphenyl)-4,4-diethyl-2-piperidin-4-yl-2,4-dihydro-3H-pyrazol-3-one (compound B7) and 3-methylbenzenesulfonyl chloride as starting compounds. The crude product is purified by crystallization from methanol to yield the title compound.
HRMS [$C_{27}H_{35}N_3O_5S$]: calc: 513.2294 found: 513.2295

119. 2-(1-{[5-(Cyclopropylmethoxy)-2-methylphenyl]carbonyl}piperidin-4-yl)-5-(3,4-dimethoxyphenyl)-4,4-dimethyl-2,4-dihydro-3H-pyrazol-3-one A solution of 0.35 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 0.11 ml (bromomethyl)cyclopropane in 8 ml ethanol is treated with 0.11 ml 10 n aqueous sodium hydroxide solution and stirred under a blanket of nitrogen for about 16 h at 80° C. until the reaction is completed largely according to TLC analysis. The solvent is evaporated under reduced pressure, and the resulting crude product is purified by chromatography (amino phase silica gel and DCM) to yield the title compound.
HRMS [$C_{30}H_{37}N_3O_5$]: calc: 519.2733 found: 519.2735

120. 2-[1-({5-[(2,6-Dichlorobenzyl)oxy]-2-methylphenyl}carbonyl)piperidin-4-yl]-5-(3,4-dimethoxyphenyl)-4,4-dimethyl-2,4-dihydro-3H-pyrazol-3-one A solution of 0.40 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 0.41 g 2-(bromomethyl)-1,3-dichlorobenzene in 5 ml ethanol is treated with 0.17 ml 10 n aqueous sodium hydroxide solution and stirred under a blanket of nitrogen for about 6 h at 80° C. until the reaction is completed largely according to TLC analysis. The solvent is evaporated under reduced pressure, and the resulting crude product is purified by chromatography (amino phase silica gel and DCM) to yield the title compound.
HRMS [$C_{33}H_{35}Cl_2N_3O_5$]: calc: 623.1954 found: 623.1955

121. 2-{1-[(5-tert-Butoxy-2-methylphenyl)carbonyl]piperidin-4-yl}-5-(3,4-dimethoxyphenyl)-4,4-dimethyl-2,4-dihydro-3H-pyrazol-3-one A solution of 0.47 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 0.50 ml 1,1-di-tert-butoxy-N,N-dimethylmethanamine in 10 ml anhydrous toluene is stirred under a blanket of nitrogen for about 90 minutes at 100° C. with three additional portions of 0.50 ml 1,1-di-tert-butoxy-N,N-dimethylmethanamine each, added every 20 minutes. The reaction mixture is stirred for another 30 minutes at 125° C. until the reaction is completed largely according to TLC analysis. The solvent is evaporated under reduced pressure, and the resulting crude product is purified by chromatography (amino phase silica gel and DCM) and by crystallization from methanol to yield the title compound.
HRMS [$C_{30}H_{39}N_3O_5$]: calc: 521.2890 found: 521.2891

122. 2-(1-{[5-(Difluoromethoxy)-2-methylphenyl]carbonyl}piperidin-4-yl)-5-(3,4-dimethoxyphenyl)-4,4-dimethyl-2,4-dihydro-3H-pyrazol-3-one In a pressure vessel 0.47 g of 5-(3,4-dimethoxyphenyl)-2-{1-[(5-hydroxy-2-methylphenyl)carbonyl]piperidin-4-yl}-4,4-dimethyl-2,4-dihydro-3H-pyrazol-3-one (compound described in example 85) and 37 mg tetrabutylammonium iodide are solved in a mixture of 20 ml methanol and 5 ml dioxane. After the reaction mixture has been frozen to a solid block upon cooling with dry ice, a layer of 4 ml THF is placed above the frozen reaction mixture and the pressure vessel is charged with 2.8 g of chloro(difluoro)methane. The pressure vessel is heated for 90 minutes to 70° C. and after the reaction mixture has reached RT, it is portioned between diethyl ether and water. After separation of the phases, the organic phase is washed with brine, dried over $MgSO_4$, and the solvents are removed under reduced pressure. The crude product is purified by chromatography (silica gel and DCM) to yield the title compound.
HRMS [$C_{27}H_{31}F_2N_3O_5$]: calc: 515.2232 found: 515.2231

123. 2-(1-{[5-(Difluoromethoxy)-2-methylphenyl]carbonyl}piperidin-4-yl)-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP2-WU2 using 5-(7-methoxy-2,2-dimethyl-2,3-dihydro-1-benzofuran-4-yl)-4,4-dimethyl-2-piperidin-4-yl-2,4-dihydro-3H-pyrazol-3-one (compound B5) and 5-(difluoromethoxy)-2-methylbenzoic acid (compound F4) as starting compounds. The crude product is purified by chromatography (amino phase silica gel and DCM) and by crystallization from DCM and diethyl ether to yield the title compound.
HRMS [$C_{30}H_{35}F_2N_3O_5$]: calc: 555.2545 found: 555.2547

124. 2-(1-{[5-(Difluoromethoxy)-2-methylphenyl]carbonyl}piperidin-4-yl)-5-(7-methoxy-3H-spiro[1-benzofuran-2,1'-cyclopentan]-4-yl)-4,4-dimethyl-2,4-dihydro-3H-pyrazol-3-one The title compound is prepared analogously as described for GP2-WU2 using 5-(7-methoxy-3H-spiro[1-benzofuran-2,1'-cyclopentan]-4-yl)-4,4-dimethyl-2-piperidin-4-yl-2,4-dihydro-3H-pyrazol-3-one (compound B6) and 5-(difluoromethoxy)-2-methylbenzoic acid (compound F4) as starting compounds. The crude product is purified by chromatography (amino phase silica gel and DCM) and by crystallization from DCM and diethyl ether to yield the title compound.
HRMS [$C_{32}H_{37}F_2N_3O_5$]: calc: 581.2701 found: 581.2707

125. 5-(3,4-Dimethoxyphenyl)-4,4-dimethyl-2-(1-{[2-methyl-5-(trifluoromethoxy)phenyl]carbonyl}piperidin-4-yl)-2,4-dihydro-3H-pyrazol-3-one The title compound is prepared analogously as described for GP2-WU2 using 5-(3,4-dimethoxyphenyl)-4,4-dimethyl-2-piperidin-4-yl-2,4-dihydro-3H-pyrazol-3-one (compound B1) and 2-methyl-5-(trifluoromethoxy)benzoic acid (compound F5) as starting compounds. The crude product is purified by chromatography (amino phase silica gel and DCM) and by crystallization from DCM and diethyl ether to yield the title compound.

HRMS [$C_{27}H_{30}F_3N_3O_5$]: calc: 533.2138 found: 533.2142

126. 5-(7-Methoxy-3H-spiro[1-benzofuran-2,1'-cyclopentan]-4-yl)-4,4-dimethyl-2-(1-{[2-methyl-5-(trifluoromethoxy)phenyl]carbonyl}piperidin-4-yl)-2,4-dihydro-3H-pyrazol-3-one The title compound is prepared analogously as described for GP2-WU2 using 5-(7-methoxy-3H-spiro[1-benzofuran-2,1'-cyclopentan]-4-yl)-4,4-dimethyl-2-piperidin-4-yl-2,4-dihydro-3H-pyrazol-3-one (compound B6) and 2-methyl-5-(trifluoromethoxy)benzoic acid (compound F5) as starting compounds. The crude product is purified by chromatography (amino phase silica gel and DCM) and by crystallization from DCM and diethyl ether to yield the title compound.

HRMS [$C_{32}H_{36}F_3N_3O_5$]: calc: 599.2607 found: 599.2607

127. 5-(3,4-Dimethoxyphenyl)-2-{1-[(2-methoxynaphthalen-1-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-methoxynaphthalene-1-carboxylic acid as starting compounds. The crude product is purified by chromatography (amino phase silica gel and DCM) and by crystallization from diethyl ether to yield the title compound.

HRMS [$C_{30}H_{33}N_3O_5$]: calc: 515.2420 found: 515.2416

128. 5-(3,4-Dimethoxyphenyl)-4,4-dimethyl-2-{1-[(2-methylnaphthalen-1-yl)carbonyl]piperidin-4-yl}-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-methylnaphthalene-1-carboxylic acid as starting compounds. The crude product is purified by chromatography (amino phase silica gel and DCM) and by crystallization from diethyl ether to yield the title compound.

HRMS [$C_{30}H_{33}N_3O_4$]: calc: 499.2471 found: 499.2467

129. 2-{1-[(4,7-Dimethoxynaphthalen-1-yl)carbonyl]piperidin-4-yl}-5-(3,4-dimethoxyphenyl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 4,7-dimethoxynaphthalene-1-carboxylic acid as starting compounds. The crude product is purified by chromatography (amino phase silica gel and DCM) and by crystallization from diethyl ether to yield the title compound.

HRMS [$C_{31}H_{35}N_3O_6$]: calc: 545.2526 found: 545.2524

130. 5-(3,4-Dimethoxyphenyl)-4,4-dimethyl-2-[1-(naphthalen-2-ylcarbonyl)piperidin-4-yl]-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and naphthalene-2-carboxylic acid as starting compounds. The crude product is purified by chromatography (amino phase silica gel and DCM) and by crystallization from diethyl ether to yield the title compound.

HRMS [$C_{29}H_{31}N_3O_4$]: calc: 485.2315 found: 485.2314

131. 5-(3,4-Dimethoxyphenyl)-2-{1-[(3-methoxynaphthalen-2-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-methoxynaphthalene-2-carboxylic acid as starting compounds. The crude product is purified by chromatography (amino phase silica gel and DCM) and by crystallization from diethyl ether to yield the title compound.

HRMS [$C_{30}H_{33}N_3O_5$]: calc: 515.2420 found: 515.2426

132. 2-{1-[(1-Bromonaphthalen-2-yl)carbonyl]piperidin-4-yl}-5-(3,4-dimethoxyphenyl)-4,4-dimethyl-2,4-dihydro-3H-pyrazol-3-one The title compound is prepared analogously as described for GP2-WU1 using 5-(3,4-dimethoxyphenyl)-4,4-dimethyl-2-(piperidin-4-yl)-2,4-dihydro-3H-pyrazol-3-one (compound B1) and 1-bromonaphthalene-2-carboxylic acid as starting compounds. The crude product is purified by crystallization from diethyl ether to yield the title compound.

HRMS [$C_{29}H_{30}BrN_3O_4$]: calc: 563.1420 found: 563.1412

133. 5-(3,4-Dimethoxyphenyl)-2-(1-{[4-(dimethylamino)naphthalen-1-yl]carbonyl}piperidin-4-yl)-4,4-dimethyl-2,4-dihydro-3H-pyrazol-3-one The title compound is prepared analogously as described for GP2-WU1 using 5-(3,4-dimethoxyphenyl)-4,4-dimethyl-2-(piperidin-4-yl)-2,4-dihydro-3H-pyrazol-3-one (compound B1) and 4-(dimethylamino)naphthalene-1-carboxylic acid as starting compounds. The crude product is purified by crystallization from diethyl ether to yield the title compound.

HRMS [$C_{31}H_{36}N_4O_4$]: calc: 528.2737 found: 528.2739

134. 5-(3,4-Dimethoxyphenyl)-4,4-dimethyl-2-{1-[(3-methylphenyl)carbonyl]piperidin-4-yl}-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-methylbenzoic acid as starting compounds. The crude product is purified by chromatography (amino

135. 5-(3,4-Dimethoxyphenyl)-4,4-dimethyl-2-(1-{[2-(trifluoromethoxy)phenyl]carbonyl}piperidin-4-yl)-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 2-(trifluoromethoxy)benzoic acid as starting compounds. The crude product is purified by chromatography (amino phase silica gel and DCM) and by crystallization from DCM and diethyl ether to yield the title compound.

HRMS [$C_{26}H_{28}F_3N_3O_5$]: calc: 519.1981 found: 519.1984

136. 5-(3,4-Dimethoxyphenyl)-2-(1-{[3-(dimethylamino)phenyl]carbonyl}piperidin-4-yl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-(dimethylamino)benzoic acid as starting compounds. The crude product is purified by chromatography (amino phase silica gel and DCM) and by crystallization from DCM and diethyl ether to yield the title compound.

HRMS [$C_{27}H_{34}N_4O_4$]: calc: 478.2580 found: 478.2587

137. 2-{1-[(2,4-Dimethoxyphenyl)carbonyl]piperidin-4-yl}-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP2-WU2 using 5-(7-methoxy-2,2-dimethyl-2,3-dihydro-1-benzofuran-4-yl)-4,4-dimethyl-2-piperidin-4-yl-2,4-dihydro-3H-pyrazol-3-one (compound B5) and 2,4-dimethoxybenzoic acid as starting compounds. The crude product is purified by chromatography (amino phase silica gel and DCM) and by crystallization from DCM and diethyl ether to yield the title compound.

HRMS [$C_{30}H_{37}N_3O_6$]: calc: 535.2682 found: 535.2683

138. 2-{1-[(2,5-Dimethylphenyl)carbonyl]piperidin-4-yl}-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP2-WU2 using 5-(7-methoxy-2,2-dimethyl-2,3-dihydro-1-benzofuran-4-yl)-4,4-dimethyl-2-piperidin-4-yl-2,4-dihydro-3H-pyrazol-3-one (compound B5) and 2,5-dimethylbenzoic acid as starting compounds. The crude product is purified by chromatography (amino phase silica gel and DCM) and by crystallization from DCM and diethyl ether to yield the title compound.

HRMS [$C_{30}H_{37}N_3O_4$]: calc: 503.2784 found: 503.2791

139. 5-(3,4-Dimethoxyphenyl)-2-{1-[(1-methoxynaphthalen-2-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 1-methoxynaphthalene-2-carboxylic acid as starting compounds. The crude product is purified by chromatography (amino phase silica gel and DCM) and by crystallization from diethyl ether to yield the title compound.

HRMS [$C_{30}H_{33}N_3O_5$]: calc: 515.2420 found: 515.2425

140. 5-(3,4-Dimethoxyphenyl)-2-{1-[(6-hydroxynaphthalen-1-yl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 6-hydroxynaphthalene-1-carboxylic acid as starting compounds. The crude product is purified by chromatography (amino phase silica gel and DCM) to yield the title compound.

HRMS [$C_{29}H_{31}N_3O_5$]: calc: 501.2264 found: 501.2265

141. 5-(3,4-Dimethoxyphenyl)-4,4-dimethyl-2-{1-[(4-methylquinolin-2-yl)carbonyl]piperidin-4-yl}-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 4-methylquinoline-2-carboxylic acid as starting compounds. The crude product is purified by chromatography (amino phase silica gel and DCM) and by crystallization from methanol to yield the title compound.

HRMS [$C_{29}H_{32}N_4O_4$]: calc: 500.2424 found: 500.2423

142. 2-(1-{[5-(Benzyloxy)-2-methylphenyl]carbonyl}piperidin-4-yl)-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP2-WU2 using 5-(7-methoxy-2,2-dimethyl-2,3-dihydro-1-benzofuran-4-yl)-4,4-dimethyl-2-piperidin-4-yl-2,4-dihydro-3H-pyrazol-3-one (compound B5) and 5-(benzyloxy)-2-methylbenzoic acid (compound F1) as starting compounds. The crude product is purified by chromatography (amino phase silica gel and DCM) and by crystallization from DCM and diethyl ether to yield the title compound.

HRMS [$C_{36}H_{41}N_3O_5$]: calc: 595.3046 found: 595.3051

143. 2-{1-[(5-Hydroxy-2-methylphenyl)carbonyl]piperidin-4-yl}-5-(7-methoxy-2,2-dimethyl-2,3-dihydro-1-benzofuran-4-yl)-4,4-dimethyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(7-methoxy-2,2-dimethyl-2,3-dihydro-1-benzofuran-4-yl)-4,4-dimethyl-2,4-dihydro-3H-pyrazol-3-one (compound described in example 142) starting compound. The crude product is purified by crystallization from DCM and diethyl ether to yield the title compound.

HRMS [$C_{29}H_{35}N_3O_5$]: calc: 505.2577 found: 505.2579

144. 2-(1-{[5-(Benzyloxy)-2-methylphenyl]carbonyl}piperidin-4-yl)-5-(7-methoxy-3H-spiro[1-benzofuran-2,1'-cyclopentan]-4-yl)-4,4-dimethyl-2,4-dihydro-3H-pyrazol-3-one The title compound is prepared analogously as described for GP2-WU2 using 5-(7-methoxy-3H-spiro[1-benzofuran- 2,1'-cyclopentan]-4-yl)-4,4-dimethyl-2-piperidin-4-yl-2,4-dihydro-3H-pyrazol-3-one (compound B6) and 5-(benzyloxy)-2-methylbenzoic acid (compound F1) as starting compounds. The crude product is purified by chromatography (amino phase silica gel and DCM) to yield the title compound.

HRMS [$C_{38}H_{43}N_3O_5$]: calc: 621.3203 found: 621.3200

145. 2-{1-[(5-Hydroxy-2-methylphenyl)carbonyl]piperidin-4-yl}-5-(7-methoxy-3H-spiro[1-benzofuran-2,1'-cyclopentan]-4-yl)-4,4-dimethyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(7-methoxy-3H-spiro[1-benzofuran-2,1'-cyclopentan]-4-yl)-4,4-dimethyl-2,4-dihydro-3H-pyrazol-3-one (compound described in example 144) as starting compound. The crude product is purified by crystallization from methanol to yield the title compound.

HRMS [$C_{31}H_{37}N_3O_5$]: calc: 531.2733 found: 531.2731

146. 2-(1-{[5-(Benzyloxy)-2-methylphenyl]carbonyl}piperidin-4-yl)-5-[3-(cyclopropylmethoxy)-4-(difluoromethoxy)phenyl]-4,4-dimethyl-2,4-dihydro-3H-pyrazol-3-one The title compound is prepared analogously as described for GP2-WU2 using 5-[3-(cyclopropylmethoxy)-4-(difluoromethoxy)phenyl]-4,4-dimethyl-2-piperidin-4-yl-2,4-dihydro-3H-pyrazol-3-one (compound B3) and 5-(benzyloxy)-2-methylbenzoic acid (compound F1) as starting compounds. The crude product is purified by chromatography (amino phase silica gel and DCM) to yield the title compound.

HRMS [$C_{36}H_{39}F_2N_3O_5$]: calc: 631.2858 found: 631.2856

147. 5-[3-(Cyclopropylmethoxy)-4-(difluoromethoxy)phenyl]-2-{1-[(5-hydroxy-2-methylphenyl)carbonyl]piperidin-4-yl}-4,4-dimethyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-[3-(cyclopropylmethoxy)-4-(difluoromethoxy)phenyl]-4,4-dimethyl-2,4-dihydro-3H-pyrazol-3-one (compound described in example 146) as starting compound. The crude product is purified by chromatography (silica gel and cyclo hexane/EA=1:1) to yield the title compound.

HRMS [$C_{29}H_{33}F_2N_3O_5$]: calc: 541.2388 found: 541.2396

148. 2-(1-{[5-(Benzyloxy)-2-methylphenyl]carbonyl}piperidin-4-yl)-5-(3,4-diethoxyphenyl)-4,4-dimethyl-2,4-dihydro-3H-pyrazol-3-one The title compound is prepared analogously as described for GP2-WU2 using 5-(3,4-diethoxyphenyl)-4,4-dimethyl-2-piperidin-4-yl-2,4-dihydro-3H-pyrazol-3-one (compound B2) and 5-(benzyloxy)-2-methylbenzoic acid (compound F1) as starting compounds. The crude product is purified by chromatography (amino phase silica gel and DCM) and by a second chromatography (silica gel and cyclohexane/EA=6:4) to yield the title compound.

HRMS [$C_{35}H_{41}N_3O_5$]: calc: 583.3046 found: 583.3047

149. 5-(3,4-Diethoxyphenyl)-2-{1-[(5-hydroxy-2-methylphenyl)carbonyl]piperidin-4-yl}-4,4-dimethyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(3,4-diethoxyphenyl)-4,4-dimethyl-2,4-dihydro-3H-pyrazol-3-one (compound described in example 148) as starting compound. Evaporation of the solvents under reduced pressure results in the title compound.

HRMS [$C_{28}H_{35}N_3O_5$]: calc: 493.2577 found: 493.2578

150. 2-(1-{[5-(Benzyloxy)-2-methylphenyl]carbonyl}piperidin-4-yl)-4-(3,4-dimethoxyphenyl)-2,3-diazaspiro[4.4]non-3-en-1-one The title compound is prepared analogously as described for GP2-WU2 using 4-(3,4-dimethoxyphenyl)-2-piperidin-4-yl-2,3-diazaspiro[4.4]non-3-en-1-one (compound B10) and 5-(benzyloxy)-2-methylbenzoic acid (compound F1) as starting compounds. The crude product is purified by chromatography (amino phase silica gel and DCM) and by a second chromatography (silica gel and cyclo hexane/EA=6:4) to yield the title compound.

HRMS [$C_{35}H_{39}N_3O_5$]: calc: 581.2890 found: 581.2894

151. 4-(3,4-Dimethoxyphenyl)-2-{1-[(5-hydroxy-2-methylphenyl)carbonyl]piperidin-4-yl}-2,3-diazaspiro[4.4]non-3-en-1-one The title compound is prepared analogously as described for the example 89 using 2-(1-{[5-(benzyloxy)-2-methylphenyl]carbonyl}piperidin-4-yl)-4-(3,4-dimethoxyphenyl)-2,3-diazaspiro[4.4]non-3-en-1-one (compound described in example 150) as starting compound. Evaporation of the solvents under reduced pressure results in the title compound.

HRMS [$C_{28}H_{33}N_3O_5$]: calc: 491.2420 found: 491.2423

152. 2-(1-{[5-(Benzyloxy)-2-methylphenyl]carbonyl}piperidin-4-yl)-5-(3,4-dimethoxyphenyl)-4-ethyl-4-methyl-2,4-dihydro-3H-pyrazol-3-one The title compound is prepared analogously as described for GP2-WU2 using 5-(3,4-dimethoxyphenyl)-4-ethyl-4-methyl-2-piperidin-4-yl-2,4-dihydro-3H-pyrazol-3-one (compound B9) and 5-(benzyloxy)-2-methylbenzoic acid (compound F1) as starting compounds. The crude product is purified by chromatography (amino phase silica gel and DCM) and by a second chromatography (silica gel and cyclo hexane/EA=6:4) to yield the title compound.

HRMS [$C_{34}H_{39}N_3O_5$]: calc: 569.2890 found: 569.2888

153. 5-(3,4-Dimethoxyphenyl)-4-ethyl-2-{1-[(5-hydroxy-2-methylphenyl)carbonyl]piperidin-4-yl}-4-methyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(3,4-dimethoxyphenyl)-4-ethyl-4-methyl-2,4-dihydro-3H-pyrazol-3-one (compound described in example 152) as starting compound. Evaporation of the solvents under reduced pressure results in the title compound.

HRMS [$C_{27}H_{33}N_3O_5$]: calc: 479.2420 found: 479.2415

154. 2-(1-{[5-(Benzyloxy)-2-methylphenyl]carbonyl}piperidin-4-yl)-5-(3,4-dimethoxyphenyl)-4-methyl-4-propyl-2,4-dihydro-3H-pyrazol-3-one The title compound is prepared analogously as described for GP2-WU2 using 5-(3,4-dimethoxyphenyl)-4-methyl-2-piperidin-4-yl-4-propyl-2,4-dihydro-3H-pyrazol-3-one (compound B8) and 5-(benzyloxy)-2-methylbenzoic acid (compound F1) as starting compounds. The crude product is purified by chromatography (amino phase silica gel and DCM) and by a second chromatography (silica gel and cyclohexane/EA=6:4) to yield the title compound.

HRMS [$C_{35}H_{41}N_3O_5$]: calc: 583.3046 found: 583.3049

155. 5-(3,4-Dimethoxyphenyl)-2-{1-[(5-hydroxy-2-methylphenyl)carbonyl]piperidin-4-yl}-4-methyl-4-propyl-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(3,4-dimethoxyphenyl)-4-methyl-4-propyl-2,4-dihydro-3H-pyrazol-3-one (compound described in example 154) as starting compound. Evaporation of the solvents under reduced pressure results in the title compound.

HRMS [$C_{28}H_{35}N_3O_5$]: calc: 493.2577 found: 493.2585

156. 2-(1-{[5-(Benzyloxy)-2-methylphenyl]carbonyl}piperidin-4-yl)-5-(3,4-dimethoxyphenyl)-4,4-diethyl-2,4-dihydro-3H-pyrazol-3-one The title compound is prepared analogously as described for GP2-WU2 using 5-(3,4-dimethoxyphenyl)-4,4-diethyl-2-piperidin-4-yl-2,4-dihydro-3H-pyrazol-3-one (compound B7) and 5-(benzyloxy)-2-methylbenzoic acid (compound F1) as starting compounds. The crude product is purified by chromatography (amino phase silica gel and DCM) and by a second chromatography (silica gel and cyclohexane/EA=1:1) to yield the title compound.

HRMS [$C_{35}H_{41}N_3O_5$]: calc: 583.3046 found: 583.3046

157. 5-(3,4-Dimethoxyphenyl)-4,4-diethyl-2-{1-[(5-hydroxy-2-methylphenyl)carbonyl]piperidin-4-yl}-2,4-dihydro-3H-pyrazol-3-one The title compound is prepared analogously as described for the example 89 using 2-(1-{[5-(benzyloxy)-2-methylphenyl]carbonyl}piperidin-4-yl)-5-(3,4-dimethoxyphenyl)-4,4-diethyl-2,4-dihydro-3H-pyrazol-3-one (compound described in example 156) as starting compound. Evaporation of the solvents under reduced pressure results in the title compound.

HRMS [$C_{28}H_{35}N_3O_5$]: calc: 493.2577 found: 493.2574

158. 2-{1-[(8-Bromonaphthalen-1-yl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 8-bromonaphthalene-1-carbonyl chloride as starting compounds. The crude product is purified by crystallization from EA and diethyl ether to yield the title compound.

HRMS [$C_{29}H_{30}BrN_3O_4$]: calc: 563.1420 found: 563.1421

159. 5-(3,4-Dimethoxyphenyl)-2-{1-[(4-hydroxy-2-methylphenyl)carbonyl]piperidin-4-yl}-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 4-hydroxy-2-methylbenzoic acid as starting compounds. The crude product is purified by chromatography (amino phase silica gel and DCM) to yield the title compound.

HRMS [$C_{26}H_{31}N_3O_5$]: calc: 465.2264 found: 465.2265

160. 2-(1-{[3-(Cyclopropylmethoxy)-4-(difluoromethoxy)phenyl]carbonyl}piperidin-4-yl)-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP2-WU2 using 5-(3,4-dimethoxyphenyl)-4,4-dimethyl-2-(piperidin-4-yl)-2,4-dihydro-3H-pyrazol-3-one (compound B1) and 3-(cyclopropylmethoxy)-4-(difluoromethoxy)benzoic acid as starting compounds. The crude product is purified by chromatography (amino phase silica gel and DCM) to yield the title compound.

HRMS [$C_{33}H_{39}F_2N_3O_6$]: calc: 611.2807 found: 611.2805

161. Methyl 3-({4-[3-(3,4-dimethoxyphenyl)-4,4-dimethyl-5-oxo-4,5-dihydro-1H-pyrazol-1-yl]piperidin-1-yl}carbonyl)benzoate The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 3-(methoxycarbonyl)benzoic acid as starting compounds. The crude product is purified by crystallization from EA and diethyl ether to yield the title compound.

HRMS [$C_{27}H_{31}N_3O_6$]: calc: 493.2213 found: 493.2218

162. 2-{1-[(3-Aminophenyl)carbonyl]piperidin-4-yl}-5-(3,4-dimethoxyphenyl)-4,4-dimethyl-2,4-dihydro-3H-pyrazol-3-one Step 2: 2.5 g of 5-(3,4-dimethoxyphenyl)-4,4-dimethyl-2-{1-[(3-nitrophenyl)carbonyl]piperidin-4-yl}-2,4-dihydro-3H-pyrazol-3-one (see below) are solved in a mixture of 50 ml EA and 20 ml ethanol, and 0.70 g palladium of charcoal (5%) are added. The reaction mixture is stirred for about 4 h at 60° C. under an atmosphere of hydrogen until the reaction is completed according to TLC analysis. The mixture is filtered over a plug of celite, and washed thoroughly with a mixture of EA and ethanol. After the solvents have been removed under reduced pressure, the resulting crude product is purified by crystallization from EA and diethyl ether yielding the title compound.

HRMS [$C_{25}H_{30}N_4O_4$]: calc: 450.2267 found: 450.2267

Step 1: 5-(3,4-Dimethoxyphenyl)-4,4-dimethyl-2-{1-[(3-nitrophenyl)carbonyl]piperidin-4-yl}-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-nitrobenzoyl chloride as starting compounds. The crude product is purified by column chromatography (silica gel and DCM/EA=1:1) and by crystallization from EA and diethyl ether to yield 5-(3,4-dimethoxyphenyl)-4,4-dimethyl-2-{1-[(3-nitrophenyl)carbonyl]piperidin-4-yl}-2,4-dihydro-3H-pyrazol-3-one as the product.

163. N-[3-({4-[3-(3,4-Dimethoxyphenyl)-4,4-dimethyl-5-oxo-4,5-dihydro-1H-pyrazol-1-yl]piperidin-1-yl}carbonyl)phenyl]acetamide The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 3-(acetylamino)benzoyl chloride as starting compounds. The crude product is purified by crystallization from EA and diethyl ether to yield the title compound.

HRMS [$C_{27}H_{32}N_4O_5$]: calc: 492.2373 found: 492.2362

164. 5-(3,4-Dimethoxyphenyl)-2-{1-[(2-methoxyphenyl)carbonyl]piperidin-4-yl}-4,4-dimethyl-2,4-dihydro-3H-pyrazol-3-one The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 2-methoxybenzoic acid as starting compounds. The crude product is purified by crystallization from methanol to yield the title compound.

HRMS [$C_{26}H_{31}N_3O_5$]: calc: 465.2264 found: 465.2263

165. 2-{1-[(2-Chlorophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-chlorobenzoyl chloride as starting compounds. The crude product is purified by crystallization from EA and diethyl ether to yield the title compound.

HRMS [$C_{25}H_{28}ClN_3O_4$]: calc: 469.1768 found: 469.1769

166. 5-(3,4-Dimethoxyphenyl)-2-{1-[(2,6-dimethoxyphenyl)carbonyl]piperidin-4-yl}-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,6-dimethoxybenzoyl chloride as starting compounds. The crude product is purified by crystallization from EA and diethyl ether to yield the title compound.

HRMS [$C_{27}H_{33}N_3O_6$]: calc: 495.2369 found: 495.2370

167. 5-(3,4-Dimethoxyphenyl)-2-{1-[(2,5-dimethylphenyl)carbonyl]piperidin-4-yl}-4,4-dimethyl-2,4-dihydro-3H-pyrazol-3-one The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 2,5-dimethylbenzoic acid as starting compounds. The crude product is purified by crystallization from methanol to yield the title compound.

HRMS [$C_{27}H_{33}N_3O_4$]: calc: 463.2471 found: 463.2475

168. 2-{1-[(2,3-Difluorophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,3-difluorobenzoyl chloride as starting compounds. The crude product is purified by crystallization from EA and diethyl ether to yield the title compound.

HRMS [$C_{25}H_{27}F_2N_3O_4$]: calc: 471.1970 found: 471.1968

169. 2-{1-[(2,6-Difluorophenyl)carbonyl]piperidin-4-yl}-5-(3,4-dimethoxyphenyl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2,6-difluorobenzoyl chloride as starting compounds. The crude product is purified by crystallization from EA and diethyl ether to yield the title compound.

HRMS [$C_{25}H_{27}F_2N_3O_4$]: calc: 471.1970 found: 471.1970

170. 2-{1-[(2-Fluorophenyl)carbonyl]piperidin-4-yl}-5-(7-methoxy-2,2-dimethyl-2,3-dihydro-1-benzofuran-4-yl)-4,4-dimethyl-2,4-dihydro-3H-pyrazol-3-one The title compound is prepared analogously as described for GP1 using 5-(3,4-dimethoxyphenyl)-4,4-dimethyl-2-(piperidin-4-yl)-2,4-dihydro-3H-pyrazol-3-one hydrochloride (compound B1*HCl) and 2-fluorobenzoyl chloride as starting compounds. The crude product is purified by crystallization from EA and diethyl ether to yield the title compound.

HRMS [$C_{28}H_{32}FN_3O_4$]: calc: 493.2377 found: 493.2377

171. 2-{1-[(2-Chloro-5-ethoxyphenyl)carbonyl]piperidin-4-yl}-5-(3,4-dimethoxyphenyl)-4,4-dimethyl-2,4-dihydro-3H-pyrazol-3-one Step 2: 0.3 g of the mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one (both compounds see below) and 0.17 g potassium carbonate are suspended in 20 ml of DMSO. 0.08 ml of 2-iodoethane are added and the reaction mixture is stirred at 55° C. under a blanket of nitrogen for about 3.5 h until the reaction is completed according to TLC analysis. The solvent is evaporated under reduced pressure, and the remaining residue is taken up in EA. The organic phase is washed with water, twice with 1 M aqueous sodium hydroxide solution and brine. The organic phase is dried over MgSO$_4$, and the solvent is removed under reduced pressure. Purification of the resulting crude product by column chromatography (silica gel and EA) yields the title compound.

HRMS [$C_{27}H_{32}ClN_3O_5$]: calc: 513.2031 found: 513.2022

Step 1: Mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one Under a blanket of nitrogen 5.08 g of 2-(1-{[5-(benzyloxy)-2-chlorophenyl]carbonyl}piperidin-4-yl)-5-(3,4-dimethoxyphenyl)-4,4-dimethyl-2,4-dihydro-3H-pyrazol-3-one (compound described in example 79) are dissolved in 20 ml of methanol and 0.53 g palladium on charcoal (10%) and 2.81 g ammonium formiate are added. The reaction mixture is heated to reflux or 45 min until the starting material is consumed according to TLC analysis. The mixture is filtered over a plug of celite, and the solvent is removed under reduced pressure resulting in the crude product, which is taken up in EA and washed tree times with water. Crystallization from EA results in a mixture of 2-{1-[(2-chloro-5-hydroxyphenyl)carbonyl]piperidin-4-yl}-5-(3,4-dimethoxyphenyl)-4,4-dimethyl-2,4-dihydro-3H-pyrazol-3-one and 5-(3,4-dimethoxyphenyl)-2-{1-[(3-hydroxyphenyl)carbonyl]piperidin-4-yl}-4,4-dimethyl-2,4-dihydro-3H-pyrazol-3-one as the product.

HRMS [$C_{25}H_{28}ClN_3O_5$ and $C_{25}H_{29}N_3O_5$]: calc: 485.1717 and 451.2107 found: 485.1733 and 451.2118

172. 5-(3,4-Dimethoxyphenyl)-2-{1-[(2-ethylphenyl)carbonyl]piperidin-4-yl}-4,4-dimethyl-2,4-dihydro-3H-pyrazol-3-one The title compound is prepared analogously as described for GP3 using 5-(3,4-dimethoxyphenyl)-4,4-dimethyl-2-(piperidin-4-yl)-2,4-dihydro-3H-pyrazol-3-one (compound B1) and 2-ethylbenzoic acid as starting compounds. The crude product is purified by crystallization from methanol to yield the title compound.

HRMS [$C_{27}H_{33}N_3O_4$]: calc: 463.2471 found: 463.2472

173. 5-[3-(Benzyloxy)-4-methoxyphenyl]-4,4-dimethyl-2-{1-[(3-methylphenyl)sulfonyl]piperidin-4-yl}-2,4-dihydro-3H-pyrazol-3-one The title compound is prepared analogously as described for GP1 using 5-[3-(benzyloxy)-4-methoxyphenyl]-4,4-dimethyl-2-(piperidin-4-yl)-2,4-dihydro-3H-pyrazol-3-one hydrochloride (compound B4*HCl) and 3-methylbenzenesulfonyl chloride as starting compounds. The crude product is purified by crystallization from methanol to yield the title compound.

HRMS [$C_{31}H_{35}N_3O_5S$]: calc: 561.2297 found: 561.2300

174. 5-(3-Hydroxy-4-methoxyphenyl)-4,4-dimethyl-2-{1-[(3-methylphenyl)sulfonyl]piperidin-4-yl}-2,4-dihydro-3H-pyrazol-3-one The title compound is prepared analogously as described for the example 89 using 5-[3-(benzyloxy)-4-methoxyphenyl]-4,4-dimethyl-2-{1-[(3-methylphenyl)sulfonyl]piperidin-4-yl}-2,4-dihydro-3H-pyrazol-3-one (compound described in example 173) starting compound. The crude product is purified by crystallization from methanol to yield the title compound.

HRMS [$C_{24}H_{29}N_3O_5S$]: calc: 471.1828 found: 471.1830

175. 5-[3-(Benzyloxy)-4-methoxyphenyl]-2-(1-{[5-(benzyloxy)-2-methylphenyl]carbonyl}piperidin-4-yl)-4,4-dimethyl-2,4-dihydro-3H-pyrazol-3-one The title compound is prepared analogously as described for GP2-WU2 using 5-[3-(benzyloxy)-4-methoxyphenyl]-4,4-dimethyl-2-(piperidin-4-yl)-2,4-dihydro-3H-pyrazol-3-one hydrochloride (compound B4*HCl) and 5-(benzyloxy)-2-methylbenzoic acid (compound F1) as starting compounds. The crude product is purified by chromatography (amino phase silica gel and DCM) to yield the title compound.

HRMS [$C_{39}H_{41}N_3O_5$]: calc: 631.3046 found: 631.3043

176. 5-(3-Hydroxy-4-methoxyphenyl)-2-{1-[(5-hydroxy-2-methylphenyl)carbonyl]piperidin-4-yl}-4,4-dimethyl-2,4-dihydro-3H-pyrazol-3-one The title compound is prepared analogously as described for the example 89 using 5-[3-(benzyloxy)-4-methoxyphenyl]-2-(1-{[5-(benzyloxy)-2-methylphenyl]carbonyl}piperidin-4-yl)-4,4-dimethyl-2,4-dihydro-3H-pyrazol-3-one (compound described in example 175) as starting compound. The crude product is purified by crystallization from methanol to yield the title compound.

HRMS [$C_{25}H_{29}N_3O_5$]: calc: 451.2107 found: 451.2103

Starting Compounds

B1. 5-(3,4-Dimethoxyphenyl)-4,4-dimethyl-2-piperidin-4-yl-2,4-dihydro-3H-pyrazol-3-one Alternative 1: Preparation of the Title Compound Starting from Compound C1:

20 g NaH (60% in mineral oil) is suspended in 500 ml of dry DMF under a blanket of dry nitrogen. 124 g 5-(3,4-dimethoxyphenyl)-4,4-dimethyl-2,4-dihydro-3H-pyrazol-3-one (compound C1) is added in portions and stirred for an additional 30 min at RT. The solution becomes slightly yellow. 168 g tert-butyl 4-{[(4-methylphenyl)sulfonyl]oxy}piperidine-1-carboxylate (compound E1) in 150 ml of DMF is added in one portion and the mixture is placed in a preheated oil bath (140° C.) and heated for 1.0 hr. The mixture is cooled to 50° C. (part of the sodium toluenesulfonate crystallizes) 1000 ml of water is added and the mixture is extracted with 200 ml of ethyl acetate (five times). The combined organic layers are washed with 100 ml of water (five times), 50 ml of brine, dried over $MgSO_4$ and concentrated in vacuo. The oil obtained is dissolved in 300 ml of ethanol and 300 ml of 1M $H_2SO_4$ is added and heated at reflux for 60 min. The ethanol is removed in vacuo, 200 ml of water is added and washed with 100 ml DCM (five times). The aqueous layer is basified with 40 g NaOH in 250 ml water and extracted with 200 ml of dichloromethane (three times), dried over $MgSO_4$ and concentrated in vacuo. The oil is suspended in 300 ml of ethanol with 30 ml of concentrated hydrochloric acid and heated until it dissolves. Cooling in ice causes precipitation. The collected precipitates are dried resulting in the hydrochloride salt of the title compound. (compound B1*HCl)

M.p. 217-220° C.

The hydrochloride of the title compound (compound B1*HCl) is suspended in water, and the aqueous layer is basified with 5 M aqueous sodium hydroxide solution to a pH above 10. The aqueous phase is extracted three times with DCM, dried over MgSO₄ and concentrated in vacuo resulting in the title compound. (compound B1)

M.p. 119-122° C.

Alternative 2: Preparation of the Title Compound Starting from Compound D1:

1000 g of methyl 3-(3,4-dimethoxyphenyl)-2,2-dimethyl-3-oxopropanoate (compound D1) are dissolved in 10.5 l of methanol. 2500 g piperidin-4-yl-hydrazine dihydrochloride, solved in 4 l of water are added rapidly. The mixture is heated to reflux and kept at reflux temperature for 4 days. The reaction mixture is cooled to 20° C., 10 l of water are added and then methanol is removed by distillation in vacuum. The aqueous solution is allowed to stand overnight at RT. The solution is cooled and aqueous sodium hydroxide (c=10 mol/l) (about 2 l) is added during 4 to 5 h by keeping the temperature below 20° C. and the pH should be higher than 13. The product crystallizes during adding of sodium hydroxide. The mixture is stirred 1 h at 10° C., filtered over a filter press and washed with 0.5 l of water. The product is dried at 50° C. in a circulating air dryer resulting in the title compound. (compound B1)

M.p. 119-122° C.

B2. 5-(3,4-diethoxyphenyl)-4,4-dimethyl-2-piperidin-4-yl-2,4-dihydro-3H-pyrazol-3-one Prepared analogously as described for the example B1 (Alternative 1) using 5-(3,4-diethoxyphenyl)-4,4-dimethyl-2,4-dihydro-3H-pyrazol-3-one (compound C2) and tert-butyl 4-(Toluene-4-sulfonyloxy)piperidine-1-carboxylate (compound E1) as starting compounds resulting in the hydrochloride salt of the title compound. (compound B2*HCl)

M.p. 221-224° C.

B3. 5-[3-(cyclopropylmethoxy)-4-(difluoromethoxy)phenyl]-4,4-dimethyl-2-piperidin-4-yl-2,4-dihydro-3H-pyrazol-3-one Prepared analogously as described for the example B1 (Alternative 1) using 5-[3-(cyclopropylmethoxy)-4-(difluoromethoxy)phenyl]-4,4-dimethyl-2,4-dihydro-3H-pyrazol-3-one (compound C3) and tert-butyl 4-(Toluene-4-sulfonyloxy)-piperidine-1-carboxylate (compound E1) as starting compounds resulting in the hydrochloride salt of the title compound. (compound B3*HCl)

M.p. 236-237° C.

B4. 5-[3-(Benzyloxy)-4-methoxyphenyl]-4,4-dimethyl-2-(piperidin-4-yl)-2,4-dihydro-3H-pyrazol-3-one Prepared analogously as described for the example B1 (Alternative 1) using 5-[3-(benzyloxy)-4-methoxyphenyl]-4,4-dimethyl-2,4-dihydro-3H-pyrazol-3-one (compound C4) and tert-butyl 4-{[(4-methylphenyl)sulfonyl]oxy}piperidine-1-carboxylate (compound E1) as starting compounds resulting in the hydrochloride salt of the title compound. (compound B4*HCl)

M.p. 243° C. (with decomposition)

B5. 5-(7-Methoxy-2,2-dimethyl-2,3-dihydro-1-benzofuran-4-yl)-4,4-dimethyl-2-piperidin-4-yl-2,4-dihydro-3H-pyrazol-3-one Prepared analogously as described for the example B1 (Alternative 1) using 5-(7-methoxy-2,2-dimethyl-2,3-dihydro-1-benzofuran-4-yl)-4,4-dimethyl-2,4-dihydro-3H-pyrazol-3-one (compound C5) and tert-butyl 4-{[(4-methylphenyl)sulfonyl]oxy}piperidine-1-carboxylate (compound E1) as starting compounds resulting in the hydrochloride salt of the title compound. (compound B5*HCl)

M.p.>260° C.

B6. 5-(7-methoxy-3H-spiro[1-benzofuran-2,1'-cyclopentan]-4-yl)-4,4-dimethyl-2-piperidin-4-yl-2,4-dihydro-3H-pyrazol-3-one Prepared analogously as described for the example B1 (Alternative 1) using 5-(7-methoxy-3H-spiro[1-benzofuran-2,1'-cyclopentan]-4-yl)-4,4-dimethyl-2,4-dihydro-3H-pyrazol-3-one (compound C6) and tert-butyl 4-(Toluene-4-sulfonyloxy)-piperidine-1-carboxylate (compound E1) as starting compounds resulting in the hydrochloride salt of the title compound. (compound B6*HCl)

M.p. 212° C. (with decomposition)

B7. 5-(3,4-dimethoxyphenyl)-4,4-diethyl-2-piperidin-4-yl-2,4-dihydro-3H-pyrazol-3-one Prepared analogously as described for the example B1 (Alternative 1) using 5-(3,4-dimethoxyphenyl)-4,4-diethyl-2,4-dihydro-3H-pyrazol-3-one (compound C7) and tert-butyl 4-(Toluene-4-sulfonyloxy)piperidine-1-carboxylate (compound E1) as starting compounds resulting in the title compound. (compound B7)

M.p. 178-179° C.

B8. 5-(3,4-dimethoxyphenyl)-4-methyl-2-piperidin-4-yl-4-propyl-2,4-dihydro-3H-pyrazol-3-one Prepared analogously as described for the example B1 (Alternative 1) using 5-(3,4-dimethoxyphenyl)-4-methyl-4-propyl-2,4-dihydro-3H-pyrazol-3-one (compound C8) and tert-butyl 4-(Toluene-4-sulfonyloxy)-piperidine-1-carboxylate (compound E1) as starting compounds resulting in the hydrochloride salt of the title compound. (compound B8*HCl)

M.p. 147-152° C.

B9. 5-(3,4-dimethoxyphenyl)-4-ethyl-4-methyl-2-piperidin-4-yl-2,4-dihydro-3H-pyrazol-3-one Prepared analogous as described for the example B1 (Alternative 1) using 5-(3,4-dimethoxyphenyl)-4-ethyl-4-methyl-2,4-dihydro-3H-pyrazol-3-one (compound C9) and tert-butyl 4-(Toluene-4-sulfonyloxy)piperidine-1-carboxylate (compound E1) as starting compounds resulting in the hydrochloride salt of the title compound. (compound B9*HCl)

M.p. 214-216° C.

B10. 4-(3,4-Dimethoxyphenyl)-2-piperidin-4-yl-2,3-diazaspiro[4.4]non-3-en-1-one Prepared analogous as described for the example B1 (Alternative 1) using 4-(3,4-dimethoxyphenyl)-2,3-diazaspiro[4.4]non-3-en-1-one (compound C10) and tert-butyl 4-{[(4-methylphenyl)sulfonyl]oxy}piperidine-1-carboxylate (compound E1) as starting compounds resulting in the hydrochloride salt of the title compound. (compound B10*HCl)

M.p. 235° C. (with decomposition)

B11. 5-(3-Hydroxy-4-methoxyphenyl)-4,4-dimethyl-2-(piperidin-4-yl)-2,4-dihydro-3H-pyrazol-3-one The title compound may be prepared analogously as described for the example 89 using 5-[3-(benzyloxy)-4-methoxyphenyl]-4,4-dimethyl-2-(piperidin-4-yl)-2,4-dihydro-3H-pyrazol-3-one hydrochloride (compound B4*HCl) as starting compounds. (compound B11)

B12. 5-(7-Methoxy-2,2-dimethyl-2,3-dihydro-1-benzofuran-5-yl)-4,4-dimethyl-2-(piperidin-4-yl)-2,4-dihydro-3H-pyrazol-3-one Prepared analogous as described for the example B1 (Alternative 2) using methyl 3-(7-methoxy-2,2-dimethyl-2,3-dihydro-1-benzofuran-5-yl)-2,2-dimethyl-3-oxopropanoate (compound D12) and piperidin-4-yl-hydrazine dihydrochloride as starting compounds resulting in the title compound. (compound B12)
M.p. 125° C. (with decomposition)

C1. 5-(3,4-Dimethoxyphenyl)-4,4-dimethyl-2,4-dihydro-3H-pyrazol-3-one 192 g of methyl 3-(3,4-dimethoxyphenyl)-2,2-dimethyl-3-oxopropanoate (compound D1) is dissolved in 600 ml of ethanol, 145 ml hydrazine hydrate is added and the mixture is heated under reflux for 17 h. The mixture is concentrated in vacuo, resuspended in 400 ml of ethanol and concentrated again. The solids are refluxed for 60 min in 400 ml of ethanol, cooled to RT and filtered. The product is washed with 50 ml of ethanol followed by 100 ml of diethyl ether and dried in vacuo at 50° C.
M.p. 193-194° C.

C2. 5-(3,4-diethoxyphenyl)-4,4-dimethyl-2,4-dihydro-3H-pyrazol-3-one

Prepared analogously as described for the example C1 using methyl 3-(3,4-diethoxyphenyl)-2,2-dimethyl-3-oxopropanoate (compound D2) and hydrazine hydrate as starting compounds.
M.p. 121-122° C.

C3. 5-[3-(cyclopropylmethoxy)-4-(difluoromethoxy)phenyl]-4,4-dimethyl-2,4-dihydro-3H-pyrazol-3-one Prepared analogously as described for the example C1 using methyl 3-[3-(cyclopropylmethoxy)-4-(difluoromethoxy)phenyl]-2,2-dimethyl-3-oxopropanoate (compound D3) and hydrazine hydrate as starting compounds.
M.p. 83-85° C.

C4. 5-[3-(Benzyloxy)-4-methoxyphenyl]-4,4-dimethyl-2,4-dihydro-3H-pyrazol-3-one Prepared analogously as described for the example C1 using methyl 3-[3-(benzyloxy)-4-methoxyphenyl]-2,2-dimethyl-3-oxopropanoate (compound D4) and hydrazine hydrate as starting compounds.
M.p. 201-206° C.

C5. 5-(7-Methoxy-2,2-dimethyl-2,3-dihydro-1-benzofuran-4-yl)-4,4-dimethyl-2,4-dihydro-3H-pyrazol-3-one 1.1 g of diisopropylamine is dissolved in 50 ml of THF under a blanket of dry nitrogen and cooled to 0° C. and 7.5 ml n-BuLi (1.6M in hexane) is added drop wise. Next, the mixture is cooled to minus 40° C., using an acetone/N2 bath, and 1.2 g of methyl 2-methylproponate is added. The resulting mixture is stirred for an additional 15 min at minus 40° C., after which 2.6 g of 7-methoxy-2,2-dimethyl-2,3-dihydro-1-benzofuran-4-carbonyl chloride dissolved in 50 ml of THF is added drop wise in 60 min during which the temperature is kept below −40° C. The cooling bath is removed and stirring is continued for 60 min at RT. 10 ml of 4M hydrochloric acid is added, the THF is removed in vacuo and the aqueous layer is extracted with ethyl acetate. The ethyl acetate solution is washed subsequently with 50 ml of water, 50 ml 1M sodium carbonate and 50 ml of brine, dried over $MgSO_4$ and concentrated in vacuo. The residue is dissolved in ethanol, 2.4 g of hydrazine hydrate is added and the resulting mixture refluxed for 18 h. After cooling to room temperature, the precipitate is filtered off and dried.
M.p. 202-205° C.

C6. 5-(7-methoxy-3H-spiro[1-benzofuran-2,1'-cyclopentan]-4-yl)-4,4-dimethyl-2,4-dihydro-3H-pyrazol-3-one Prepared analogous as described for the example C5 using 7-methoxy-2,2-spirocyclopentyl-2,3-dihydrobenzofuran-4-carbonyl chloride, methyl 2-methylproponate and hydrazine hydrate as starting compounds.
M.p. 214-215° C.

C7. 5-(3,4-dimethoxyphenyl)-4,4-diethyl-2,4-dihydro-3H-pyrazol-3-one

Prepared analogously as described for the example C5 using 3,4-dimethoxybenzoyl chloride, methyl 2-ethylbutanoate and hydrazine hydrate as starting compounds.
M.p. 41-42° C.

C8. 5-(3,4-dimethoxyphenyl)-4-methyl-4-propyl-2,4-dihydro-3H-pyrazol-3-one

Prepared analogously as described for the example C5 using 3,4-dimethoxybenzoyl chloride, methyl 2-methylpentanoate and hydrazine hydrate as starting compounds.
M.p. 119-120° C.

C9. 5-(3,4-dimethoxyphenyl)-4-ethyl-4-methyl-2,4-dihydro-3H-pyrazol-3-one

Prepared analogously as described for the example C5 using 3,4-dimethoxybenzoyl chloride, methyl 2-methylbutanoate and hydrazine hydrate as starting compounds.
M.p. 145-146° C.

C10. 4-(3,4-Dimethoxyphenyl)-2,3-diazaspiro[4.4]non-3-en-1-one

Prepared analogously as described for the example C5 using 3,4-dimethoxybenzoyl chloride, methyl cyclopentancarboxylate and hydrazine hydrate as starting compounds.
M.p. 200-202° C.

D1. Methyl 3-(3,4-dimethoxyphenyl)-2,2-dimethyl-3-oxopropanoate 124 ml of diisopropylamine is dissolved in 500 ml of THF under a blanket of dry nitrogen and cooled to 0° C. and 550 ml n-BuLi (1.6M in hexane) is added drop wise. Next, the mixture is cooled to minus 40° C., using an acetone/N2 bath, and 100 ml methyl 2-methylproponate is added. The resulting mixture is stirred for an additional 15 min at minus 40° C., after which 160.5 g of 3,4-dimethoxybenzoyl chloride dissolved in 750 ml of THF is added drop wise in 60 min during which the temperature is kept below minus 40° C. The cooling bath is removed and stirring is continued for 60 min at RT. 150 ml of 4M hydrochloric acid is added and the THF layer is separated and washed with 100 ml of water, 200 ml 1M of sodium carbonate and 100 ml of brine, dried over MgSO$_4$ and concentrated in vacuo.

NMR (CDCl$_3$): δ=1.56 (s,6H), 3.65 (s,3H), 3.89 (s,3H), 3.91 (s,3H), 6.82 (d, J=8.4 Hz, 1H), 7.41 (dd,1H,J=1.4, 8.4 Hz) 7.99 (d, 1H,J=1.4 Hz).

D2. Methyl 3-(3,4-diethoxyphenyl)-2,2-dimethyl-3-oxopropanoate

Prepared analogously as described for the example D1 using methyl 2-methylproponate and 3,4-diethoxybenzoyl chloride as starting compounds.

NMR (CDCl$_3$): δ=1.31-154 (dt,6H,J=5.6 Hz), 1.56 (s,6H), 3.65 (s,3H), 4.07(m,6H), 6.82 (d, J=8.4 Hz, 1H), 7.41 (dd, 1H,J=1.4, 8.4 Hz) 7.99 (d, 1H,J=1.4 Hz).

D3. Methyl 3-[3-(cyclopropylmethoxy)-4-(difluoromethoxy)phenyl]-2,2-dimethyl-3-oxopropanoate Prepared analogously as described for the example D1 using methyl 2-methylproponate and 3-cyclopropylmethoxy-4-difluoromethoxybenzoyl chloride as starting compounds.

NMR (CDCl$_3$): δ=1.20-1.33 (m,2H), 1.50-1.63 (m,6H), 1.46 (s,6H), 3.65 (s,3H), 3.57 (s,3H), 3.82 (d,J=5.7 Hz,2H), 6.30 (s,0.4H), 6.68 (s,0.6H), 7.07 (d, J=8.4 Hz, 1H), 7.27 (dd, 1H,J=1.4, 8.4 Hz), 7.49 (d, 1H,J=1.4 Hz).

D4. Methyl 3-[3-(benzyloxy)-4-methoxyphenyl]-2,2-dimethyl-3-oxopropanoate

Prepared analogously as described for the example D1 using methyl 2-methylproponate and 3-benzyloxy-4-methoxybenzoyl chloride as starting compounds.

NMR (CDCl$_3$): 1.46 (s,6H), 3.60 (s,3H), 3.92 (s,3H), 5.12 (2,2H), 6.83 (d, J=8.4 Hz, 1H), 7.20-7.55 (m,7H)

D12. Methyl 3-(7-methoxy-2,2-dimethyl-2,3-dihydro-1-benzofuran-5-yl)-2,2-dimethyl-3-oxopropanoate Step 2: 2.63 g Mg in 75 ml anhydrous THF are preheated to 55° C., treated with 20 mg iodine and 20 mg methyl iodide, 25.7 g of 5-bromo-7-methoxy-2,2-dimethyl-2,3-dihydro-1-benzofuran (see below) are added maintaining reflux of the reaction, and the reaction is heated to reflux for 3 h until most of the Mg disappeared. 20 g dimethyl dimethylmalonate are solved in 40 ml anhydrous THF, cooled to −60° C., and the freshly prepared Grignard reagent is added drop wise over 1 h at this temperature. The reaction is allowed to warm to 5° C. and quenched with 250 ml saturated aqueous ammonium chloride solution. The reaction is extracted with ether twice, the combined organic layers are dried over MgSO$_4$, and the solvent is removed under reduced pressure. The crude product may contain some unreacted dimethyl dimethylmalonate, which could largely be distilled off under vacuum. The crude product is used for the cyclisation reaction without further purification.

Step 1: 5-bromo-7-methoxy-2,2-dimethyl-2,3-dihydro-1-benzofuran 56 g 7-methoxy-2,2-dimethyl-2,3-dihydro-1-benzofuran are dissolved in 200 ml 2-methyltetrahydrofuran, 58 g N-bromosuccinimide are added portion wise, while keeping the temperature of the reaction mixture below 50° C., and the reaction is stirred for one hour at RT. Water and diethyl ether are added to the reaction mixture, the phases are separated, the organic phase is washed with 1 M aqueous sodium carbonate solution, dried over MgSO$_4$, and the solvent is removed under reduced pressure. The resulting crude product is purified by distillation under vacuum yielding 5-bromo-7-methoxy-2,2-dimethyl-2,3-dihydro-1-benzofuran.

B. p. 122-124° C. (0.007 mbar)

E1. tert-Butyl 4-{[(4-methylphenyl)sulfonyl]oxy}piperidine-1-carboxylate 201 g tert-Butyl 4-hydroxypiperidine-1-carboxylate, 160 ml triethylamine and 6.0 g 4-dimethylaminopyridine are dissolved in 750 ml DCM. 191 g 4-toluenesulfonylchloride is added and the mixture is refluxed for 7 h. The mixture is cooled in ice and acidified with 100 ml of 1M H$_2$SO$_4$; the organic layer is washed with 300 ml of water (twice), 250 ml of 1 M Na$_2$CO$_3$ solution (twice), dried over MgSO$_4$, filtered and concentrated in vacuo.

M.p. 98-101° C.

F1. 5-(Benzyloxy)-2-methylbenzoic acid

Step 4: 5.5 g benzyl 5-(benzyloxy)-2-methylbenzoate (see below) are solved in 100 ml 2 M aqueous sodium hydroxide solution, and stirred for two days at RT and heated to reflux for one hour, until the reaction is completed according to TLC analysis. After the reaction mixture is cooled to RT, it is washed with diethyl ether twice, and acidified with concentrated hydrochloric acid. The reaction mixture is extracted with DCM, the organic phase is dried over MgSO$_4$, and the solvent is removed under reduced pressure yielding the title compound.

Step 3: Benzyl 5-(benzyloxy)-2-methylbenzoate

A mixture of 2.6 g of 5-hydroxy-2-methylbenzoic acid (see below), 7.0 g potassium carbonate and 3.8 ml benzyl chloride in 50 ml DMF are stirred at 50° C. for two hours, until the reaction is completed according to TLC analysis. The reaction mixture is portioned between water and EA, and the phases are separated. The organic phase is washed three times with 1 M sodium carbonate solution and once with brine, dried over MgSO$_4$, and the solvent is removed under reduced pressure yielding benzyl 5-(benzyloxy)-2-methylbenzoate, which is used for the next step without further purification.

Step 2: 5-Hydroxy-2-methylbenzoic acid

To a mixture of 4.27 g 5-amino-2-methylbenzoic acid (see below), 6 ml concentrated sulfuric acid and 10 ml water, 50 ml ice are added, and a solution of 2.1 g sodium nitrite in 15 ml water is added drop wise, maintaining a temperature of the reaction mixture below 7° C. After stirring this mixture for further 30 min, it is added drop wise to a refluxing mixture of 20 ml concentrated sulfuric acid and 20 ml water. The resulting mixture is held under reflux for further 10 min and stirred over night allowing the temperature to cool down to RT. The mixture is portioned between water and EA, the phases are separated, the organic phase is dried over MgSO$_4$, and the solvent is removed under reduced pressure. For further purification the remaining crude product is solved in diethyl ether, and the organic phase is washed with water, dried over MgSO$_4$, and the solvent is removed under reduced pressure, resulting in 5-hydroxy-2-methylbenzoic acid as the product, which is used for the next step without further purification.

Step 1: 5-Amino-2-methylbenzoic acid 5.24 g of 2-methyl-5-nitrobenzoic acid are dissolved in 250 ml of ethanol, 0.5 g palladium on charcoal (5%) are added, and the reaction mixture is stirred under an atmosphere of hydrogen at RT over night, until the reaction is completed according to TLC analysis. The mixture is filtered over a plug of celite, and the solvent is removed under reduced pressure resulting in the crude 5-amino-2-methylbenzoic acid, which is used for the next step without further purification.

F2. 5-(Benzyloxy)-2-methylbenzoyl chloride

To a mixture of 3.3 g 5-(benzyloxy)-2-methylbenzoic acid (compound F1) in 80 ml DCM are added 1.4 ml of oxaloylchloride, and the reaction is stirred at RT over night under a blanket of nitrogen. The solvent is removed under reduced pressure yielding the title compound, which was used without further purification.

F3. 5-(Benzyloxy)-2-chlorobenzoyl chloride

Step 4: The title compound 5-(benzyloxy)-2-chlorobenzoyl chloride is prepared analogously as described for the example F2 using 5-(benzyloxy)-2-chlorobenzoic acid as starting compound.

Step 3: 5-(Benzyloxy)-2-chlorobenzoic acid

Prepared analogously as described for the example F1 (step 4) using benzyl 5-(benzyloxy)-2-chlorobenzoate as starting compound.

Step 2: Benzyl 5-(benzyloxy)-2-chlorobenzoate

Prepared analogously as described for the example F1 (step 3) using 2-chloro-5-hydroxybenzoic acid as starting compound.

Step 1: 2-Chloro-5-hydroxybenzoic acid

Prepared analogously as described for the example F1 (step 2) using 5-amino-2-chlorobenzoic acid as starting compound.

F4. 5-(Difluoromethoxy)-2-methylbenzoic acid

Step 3: 47.5 g Methyl 5-(difluoromethoxy)-2-methylbenzoate are solved in a mixture of 120 ml methanol, 10.4 g sodium hydroxide and 80 ml water. The reaction mixture is heated to reflux and stirred for one hour at RT, until the reaction is completed according to TLC analysis. The mixture is largely evaporated under reduced pressure, and the remaining liquid is acidified with 1n aqueous hydrochloric acid. The precipitates are collected and washed with PE yielding the title compound.

Step 2: Methyl 5-(difluoromethoxy)-2-methylbenzoate

Chloro(difluoro)methane is introduced with vigorous stirring for 90 minutes into a mixture of 50 g methyl 5-hydroxy-2-methylbenzoate (see below), 1.21 g tetrabutylammonium bromide, 52 g aqueous sodium hydroxide solution (50% by weight) and 500 ml dioxane. The reaction mixture is filtered and the filtrate is adjusted to pH 1-2 with 1n aqueous hydrochloric acid. The mixture is extracted with EA three times, the combined organics are dried over $MgSO_4$, and the solvent is removed under reduced pressure. The resulting crude product is purified by filtration over a column (silica gel and PE) yielding methyl 5-(difluoromethoxy)-2-methylbenzoate, which is used for the next step without further purification.

Step 1: Methyl 5-hydroxy-2-methylbenzoate

To a mixture of 107 g 5-hydroxy-2-methylbenzoic acid (compound described in example F1 step 2) in 1000 ml methanol 251.1 g thionylchloride is added dropwise. The mixture is heated to reflux and stirred two hours at RT. After the solvent has been largely evaporated from the mixture under reduced pressure, 100 ml water are added and the reaction mixture is adjusted to pH 7 with saturated aqueous sodium hydrogen carbonate solution. The aqueous phase is extracted with 200 ml EA three times, the combined organics are dried over $MgSO_4$, and the solvent is removed under reduced pressure yielding methyl 5-hydroxy-2-methylbenzoate, which is used for the next step without further purification.

F5. 2-Methyl-5-(trifluoromethoxy)benzoic acid

Step 3: The title compound 2-Methyl-5-(trifluoromethoxy) benzoic acid is prepared analogously as described for the example F4 (step 3) using methyl 2-methyl-5-(trifluoromethoxy)benzoate as starting compound.

Step 2: Methyl 2-methyl-5-(trifluoromethoxy)benzoate

Methyl 2-methyl-5-(trifluoromethoxy)benzoate is prepared analogously to a methodology described in literature: M. Kuroboshi, K. Suzuki, T. Hiyama; Oxidative Desulfurization-Fluorination of Xanthates: A Convenient Synthesis of Trifluoromethyl Ethers and Difluoro(methylthio)methyl Ethers; Tetrahedron Lett. 1992, 33, 4173-4176; K. Kanie, Y. Tanaka, K. Suzuki, M. Kuroboshi, T. Hiyama; A Convenient Synthesis of Trifluoromethyl Ethers by Oxidative Desulfurization-Fluorination of Dithiocarbonates; Bull. Chem. Soc. Jpn. 2000, 73, 471-484. According to this methodology methyl 5-hydroxy-2-methylbenzoate (compound described in example F4 step 1) is reacted to the corresponding xanthate methyl 2-methyl-5-{[(methylsulfanyl)carbonothioyl] oxy}benzoate by reacting with $CS_2$, which is than converted into the title compound methyl 2-methyl-5-(trifluoromethoxy)benzoate by treating of the xanthate with hydrogen fluoride/pyridine complex and 1,3-dibromo-5,5-dimethylhydantoin.

Commercial Utility
Medical Uses

The compounds of formula 1, the salts of the compounds of formula 1, the stereoisomers of the compounds of formula 1 and the salts of the stereoisomers of the compounds of formula 1 according to the invention are hereinafter referred to as the compounds of the invention. In particular, the compounds of the invention are pharmaceutically acceptable.

The compounds of the invention have—as type 4 phosphodiesterase (PDE4) inhibitors—valuable pharmaceutical properties, which make them commercially utilizable.

PDE4 inhibitors are thought to be useful in the treatment or prophylaxis of a variety of diseases and disorders. They are thought to be suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways, of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases.

In particular, PDE4 inhibitors are thought to be useful in the treatment or prophylaxis of a variety of diseases and disorders, such as for example:

acute and chronic airway diseases, such as, but not limited to, bronchitis, allergic bronchitis, bronchial asthma, emphysema, COPD (chronic obstructive pulmonary disease), pulmonary hypertension and lung fibrosis;

diseases which are based on allergic and/or chronic, immunological false reactions in the region of the upper airways (pharynx, nose) and the adjacent regions (paranasal sinuses, eyes), such as, but not limited to, allergic rhinitis/sinusitis, chronic rhinitis/sinusitis, allergic conjunctivitis and also nasal polyps;

dermatological diseases especially of proliferative, inflammatory and allergic type, such as, but not limited to psoriasis (vulgaris), toxic and allergic contact eczema, atopic dermatitis (eczema), seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders;

diseases which are based on an excessive release of TNF and leukotrienes, such as, for example, diseases of the arthritis type like rheumatoid arthritis, rheumatoid spondylitis, osteoarthritis and other arthritic conditions;

fibrotic diseases, such as, but not limited to, cystic fibrosis, pulmonary fibrosis, hepatic fibrosis and renal fibrosis;

viral, alcoholic or drug-induced acute and fulminant hepatitis, hepatic steatosis (alcoholic and non-alcoholic steatiohepatitis);

diseases of the immune system, such as, but not limited to, AIDS, multiple sclerosis, graft versus host reaction, allograft rejections;

cachexia, cancer cachexia, AIDS cachexia;

types of shock, such as, but not limited to, septic shock, endotoxin shock, gram-negative sepsis, toxic shock syndrome and ARDS (adult respiratory distress syndrome);

diseases in the gastrointestinal region, such as Crohn's disease and ulcerative colitis;

diseases of the heart which can be treated by PDE inhibitors, such as cardiac insufficiency;

diseases which can be treated on account of the tissue-relaxant action of the PDE inhibitors, such as, for example, erectile dysfunction, colics of the kidneys and of the ureters in connection with kidney stones or oncolytic action (to treat preterm delivery); glomerulonephritis and other urinary tract infections;

diabetes insipidus, diabetes mellitus (type I and in particular type II); cancer (in particular lymphoid and myeloid leukaemia); osteoporosis;

conditions associated with cerebral metabolic inhibition, such as, but not limited to, cerebral senility, senile dementia (Alzheimer's disease), memory impairment associated with Parkinson's disease or multiinfarct dementia;

and also diseases of the central nervous system, such as, but not limited to, depressions, anxiety states, spinal cord injury, schizophrenia or arteriosclerotic dementia.

Accordingly, the invention further relates to the compounds of the invention for use in the treatment or prophylaxis of diseases, especially diseases alleviated by inhibition of type 4 phosphodiesterase, in particular the diseases exemplified above.

Preferably, the invention relates to the compounds of the invention for use in the treatment or prophylaxis of the following diseases:

acute and chronic airway diseases, such as bronchitis, allergic bronchitis, bronchial asthma, emphysema, COPD, pulmonary hypertension and lung fibrosis;

allergic rhinitis;

and dermatological diseases, such as psoriasis and atopic dermatitis (eczema);

rheumatoid arthritis;

and inflammations in the gastrointestinal region, such as Crohn's disease and ulcerative colitis.

The invention also relates to the use of a compound of the invention in the manufacture of a pharmaceutical composition inhibiting the type 4 phosphodiesterase, in particular a pharmaceutical composition for the treatment or prophylaxis of diseases alleviated by inhibition of type 4 phosphodiesterase, preferably, a pharmaceutical composition for the treatment or prophylaxis of the diseases exemplified above.

In particular, the invention relates to the use of a compound of the invention in the manufacture of a pharmaceutical composition for the treatment or prophylaxis of an acute or chronic airway disease, such as, but not limited to, bronchitis, allergic bronchitis, bronchial asthma, emphysema, COPD, pulmonary hypertension or lung fibrosis.

The invention relates also to the use of a compound of the invention in the manufacture of a pharmaceutical composition for the treatment or prophylaxis of allergic rhinitis.

Furthermore, the invention relates to the use of a compound of the invention in the manufacture of a pharmaceutical composition for the treatment or prophylaxis of dermatological diseases, such as, but not limited to, psoriasis or atopic dermatitis (eczema).

The invention relates as well to the use of a compound of the invention in the manufacture of a pharmaceutical composition for the treatment or prophylaxis of rheumatoid arthritis.

Additionally, the invention relates to the use of a compound of the invention in the manufacture of a pharmaceutical composition for the treatment or prophylaxis of inflammations in the gastrointestinal region, such as, but not limited to, Crohn's disease or ulcerative colitis.

In a particularly preferred embodiment of the invention, in the above-mentioned uses the compound of the invention is a compound of the examples or a pharmaceutically acceptable salt thereof according to the invention.

The invention further relates to a method of treating or preventing a disease comprising administering to a patient in need thereof a therapeutically effective amount of at least one of the compounds of the invention.

In particular, the invention relates to a method of treating or preventing one of the above mentioned diseases comprising administering to a patient in need thereof a therapeutically effective amount of at least one of the compounds of the invention.

Especially, the invention relates to a method of treating or preventing a disease, which is alleviated by inhibition of the type 4 phosphodiesterase comprising administering to a patient in need thereof a therapeutically effective amount of at least one of the compounds of the invention.

Preferably, the invention relates to a method of treating or preventing an acute or chronic airway disease, for example, but not limited to, bronchitis, allergic bronchitis, bronchial asthma, emphysema, COPD, pulmonary hypertension or lung fibrosis comprising administering to a patient in need thereof a therapeutically effective amount of at least one of the compounds of the invention.

The invention relates also to a method of treating or preventing allergic rhinitis comprising administering to a patient in need thereof a therapeutically effective amount of at least one of the compounds of the invention.

Furthermore, the invention preferably relates to a method of treating or preventing dermatological diseases, such as, but not limited to, psoriasis or atopic dermatitis (eczema) comprising administering to a patient in need thereof a therapeutically effective amount of at least one of the compounds of the invention.

The invention relates as well to a method of treating or preventing rheumatoid arthritis comprising administering to a patient in need thereof a therapeutically effective amount of at least one of the compounds of the invention.

Additionally, the invention preferably relates to a method of treating or preventing diseases in the gastrointestinal region, such as, but not limited to, Crohn's disease or ulcerative colitis comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used, more preferably, one of the compounds of the invention is used.

In a particularly preferred embodiment of the invention, the above methods of treating or preventing one of the above mentioned diseases comprise administering to a patient in need thereof a therapeutically effective amount of a compound of the examples or a pharmaceutically acceptable salt thereof according to the present invention.

Pharmaceutical Compositions

The invention furthermore relates to a pharmaceutical composition, which comprises at least one of the compounds of the invention together with at least one pharmaceutically acceptable auxiliary.

Preferably, the pharmaceutical composition comprises one or two of the compounds of the invention. More preferably, the pharmaceutical composition comprises one of the compounds of the invention.

In a particularly preferred embodiment of the invention, the pharmaceutical composition comprises a compound of the examples or a pharmaceutically acceptable salt thereof according to the present invention together with at least one pharmaceutically acceptable auxiliary.

The invention furthermore relates to a pharmaceutical composition according to the invention inhibiting the type 4 phosphodiesterase, especially for the treatment or prophylaxis of diseases alleviated by inhibition of type 4 phosphodiesterase, in particular for the treatment or prophylaxis of the diseases exemplified above.

The invention encompasses pharmaceutical compositions according to the invention, as defined above, in particular for the treatment or prophylaxis of one or more of the following diseases: acute and chronic airway diseases, such as, bronchitis, allergic bronchitis, bronchial asthma, emphysema, COPD, pulmonary hypertension and lung fibrosis; allergic rhinitis; and dermatological diseases, such as psoriasis and atopic dermatitis (eczema); rheumatoid arthritis; and inflammations in the gastrointestinal region, such as Crohn's disease and ulcerative colitis.

The compounds of the invention respectively the pharmaceutical compositions comprising the compounds of the invention may be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Depending on the characteristics of the specific compound either administration by inhalation or oral administration of the compounds of the invention is preferred.

Inhalable and Intranasal Pharmaceutical Compositions

Inhaled administration involves topical administration to the lung e.g. by aerosol or dry powder composition.

Formulations for inhalation include powder compositions, which will preferably contain lactose, and spray compositions which may be formulated, for example, as aqueous solutions or suspensions or as aerosols delivered from pressurised packs, with the use of a suitable propellant, e.g. 1, 1, 1, 2-tetrafluorethane, 1, 1, 1, 2, 3, 3, 3-heptafluoropropane, carbon dioxide or other suitable gas.

A class of propellants, which is believed to have minimal ozone-depleting effects in comparison to conventional chlorofluorocarbons comprise hydrofluorocarbons and a number of medicinal aerosol formulations using such propellant systems are disclosed in, for example, EP 0372777, WO91/04011, WO91/11173, WO91/11495, WO91/14422, WO93/11743, and EP 0553298. These applications are all concerned with the preparation of pressurised aerosols for the administration of medicaments and seek to overcome problems associated with the use of this new class of propellants, in particular the problems of stability associated with the pharmaceutical formulations prepared. The applications propose, for example, the addition of one or more of excipients such as polar cosolvents or wetting agents (e.g. alcohols such as ethanol), alkanes, dimethyl ether, surfactants (including fluorinated and non-fluorinated surfactants, carboxylic acids such as oleic acid, polyethoxylates etc.) or bulking agents such as a sugar (see for example WO02/30394) and vehicles such as cromoglicic acid and/or nedocromil which are contained at concentrations, which are not therapeutically and prophylactically active (see WO00/07567). The aerosol dosage form can also take the form of a pump-atomizer.

For suspension aerosols, the compound of the invention should be micronised so as to permit inhalation of substantially all of the compound of the invention into the lungs upon administration of the aerosol formulation, thus the compound of the invention will have a mean particle size of less than 100 µm, desirably less than 20 µm, and preferably in the range of 1 to 10 µm (D50 value, e.g. as measured using laser diffraction).

Dry powder inhalable compositions: For pharmaceutical compositions suitable (e.g. adapted for) inhaled administration, the pharmaceutical composition may for example be a dry powder inhalable composition. The dry powder comprises finely divided compound of the invention optionally together with a finely divided pharmaceutically acceptable carrier, which is preferably present and may be one or more materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran or mannitol. An especially preferred carrier is lactose, particularly in the form of the monohydrate.

The dry powder may be in capsules of gelatine or plastic, or in blisters, for use in a dry powder inhalation device, preferably in dosage units of the compound of the invention together with the carrier in amounts to bring the total weight of powder in each capsule to from 5 mg to 50 mg. Alternatively the dry powder may be contained in a reservoir of a multi-dose dry powder inhalation device. Capsules and cartridges of for example gelatin, or blisters of for example laminated aluminium foil, for use in an inhaler or insulator may be formulated containing a powder mix of the compounds of the invention and a suitable powder base such as lactose or starch, preferably lactose. In this aspect, the compound of the invention is suitably micronised so as to permit inhalation of substantially all of the compound of the invention into the lungs upon administration of the dry powder formulation, thus the compound of the invention will have a particle size of less than 100 µm, desirably less than 20 µm, and preferably in the range 1 to 10 µm (D50 value, e.g. as measured using laser diffraction). The solid carrier, where present, generally has a maximum particle diameter of 300 µm, preferably 200 µm, and conveniently has a mean particle diameter of 40 to 100 µm, preferably 50 to 75 µm. The particle size of the compound of the invention and that of a solid carrier where present in dry powder compositions, can be reduced to the desired level by conventional methods, for example by grinding in an air-jet mill, ball mill or vibrator mill, microprecipitation, spray drying, lyophilisation or recrystallisation from supercritical media.

Where the inhalable form of the composition of the invention is the finely divided particulate form, the inhalation device may be, for example a dry powder inhalation device adapted to deliver dry powder from a capsule or blister containing a dosage unit of the dry powder or a multi-dose dry powder inhalation device. Such dry powder inhalation devices are known in the art. Examples which may be mentioned are Cyclohaler®, Diskhaler®, Rotadisk®, Turbohaler®, Novolizer®, Easyhaler®, Jethaler®, Clickhaler® or the dry powder inhalation devices disclosed in EP 0 505 321, EP 407028, EP 650410, EP 691865 or EP 725725 (Ultrahaler®).

Formulations for inhalation by nebulization may be formulated with an aqueous vehicle with the addition of agents such as acid or alkali, buffer salts, isotonicity adjusting agents or antimicrobials. They may be sterilised by filtration or heating in an autoclave. Suitable technologies for this type of administration are known in the art. As an example the Mystic® technology is to be mentioned (see for example U.S. Pat. Nos. 6,397,838, 6,454,193 and 6,302,331).

Preferred unit dosage formulations are those containing a pharmaceutical effective dose, as hereinbelow recited, or an appropriate fraction thereof, of the active ingredient. Thus, in the case of formulations designed for delivery by metered dose pressurised aerosols, one actuation of the aerosol may deliver half of the therapeutical effective amount such that two actuations are necessary to deliver the therapeutically effective dose.

In the dry powder inhalable composition, the compound of the invention can for example be present in about 0.1% to about 70% (e.g. about 1% to about 50%, e.g. about 5% to about 40%, e.g. about 20 to about 30%) by weight of the composition.

In case of intranasal administration, for example, sprays and solutions to be applied in drop form are preferred formulations. Intranasal sprays or nasal drops may be formulated with aqueous or non-aqueous vehicles with or without the addition of agents such as thickening agents, buffer salts or acid or alkali to adjust the pH, isotonicity adjusting agents, preservatives or anti-oxidants.

Pharmaceutical Compositions Suitable for External Topical Administration

"External topical" administration means topical administration to an external body part (i.e. excluding, for example, the lung or mouth, but including the lips or the eye). External topical administration (e.g. through the skin/transdermal) can for example be to those parts of the skin affected by or susceptible to a dermatological disease, such as for example, atopic dermatitis or psoriasis.

In case of external topical administration (i.e. through the skin/transdermal), suitable pharmaceutical formulations are, for example, ointments, creams (usually an oil-in-water or water-in-oil pharmaceutical composition, usually an emulsion), lotions, pastes, gels, powders, solutions, emulsions, suspensions, oils, sprays and patches (e.g., but not limited to, transdermal therapeutic systems).

In an external-topical pharmaceutical composition, e.g. an ointment or an oil-in-water or water-in-oil composition, the compound of the invention is suitably present in 0.05 to 10%, preferably 0.1 to 5%, more preferably 0.1 to 3%, still more preferably 0.5 to about 2.5%, by weight of the composition (w/w).

Pharmaceutical Compositions for Oral or Parenteral Administration

For parenteral modes of administration such as, for example, intravenous, subcutaneous or intramuscular administration, preferably solutions (e.g., but not limited to, sterile solutions, isotonic solutions) are used. They are preferably administered by injection or infusion techniques.

A pharmaceutical composition suitable for parenteral (e.g. intravenous, subcutaneous or intramuscular) administration can comprise a solution or suspension of the compound of the invention in a sterile parenterally acceptable carrier (e.g. sterile water) or parenterally acceptable oil. Alternatively, the solution can be lyophilised. A lyophilised pharmaceutical composition suitable for parenteral administration may, in use, optionally be reconstituted with a suitable solvent, e.g. sterile water or a sterile parenterally acceptable aqueous solution, just prior to administration.

A pharmaceutical composition for oral administration may be liquid or solid; for example, it may be a syrup, suspension or emulsion; as well it may be, for example, a tablet, coated tablet (dragee), pill, cachet, capsule (caplet), or in form of granules.

A liquid formulation may optionally consist of a suspension or solution of the compound of the invention in a pharmaceutically acceptable liquid carrier, for example an aqueous solvent such as water, ethanol or glycerine, or a non-aqueous solvent, such as polyethylene glycol or an oil. The formulation may contain in addition, a suspending agent, a preservative, a flavouring and/or a colouring agent.

A pharmaceutical composition for oral administration being a tablet may comprise one or more pharmaceutically acceptable auxiliaries (for example, carriers and/or excipients) suitable for preparing tablet formulations. The carrier may, for example, be or include lactose, cellulose or mannitol. The tablet may also or instead contain one or more pharmaceutically acceptable excipients, for example, a binding agent, a lubricant and/or a tablet disintegrant.

The pharmaceutical compositions according to the invention for oral or parenteral administration preferably contain the compound or compounds of the invention in a total amount of from 0.1 to 99.9%, more preferably 5 to 95%, in particular 20 to 80% by weight of the composition (w/w).

In general, as pharmaceutically acceptable auxiliaries, any auxiliaries known to be suitable for preparing a particular pharmaceutical composition can be used. Examples thereof include, but are not limited to, solvents, excipients, dispersants, emulsifiers, solubilizers, gel formers, ointment bases, anti-oxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions/formulations can be manufactured in a manner known to a person skilled in the art, e.g. by dissolving, mixing, granulating, dragee-making, levigating, emulsifying, encapsulating, entrapping or lyophilizing processes.

Dosages

Generally, the pharmaceutical compositions according to the invention can be administered such that the dose of the compound of the invention is in the range customary for type 4 phosphodiesterase inhibitors.

The pharmaceutically acceptable compounds of the invention are preferably administered in a daily dose (for an adult patient) of, for example an oral or parenteral dose of 0.01 mg to 250 mg per day, preferably 0.05 mg to 100 mg per day, more preferably 0.05 mg to 10 mg per day, or a nasal or inhaled dose of 0.001 mg to 10 mg per day, preferably 0.01 mg to 7.5 mg per day, more preferably 0.01 mg to 5 mg per day, of the compound of the invention, calculated as the free compound (=the unsolvated, unhydrated, non-salt form of the compound).

In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical compositions of the invention can be administered in a single dose per day or in multiple subdoses, for example, 2 to 4 doses per day. A single dose unit of the pharmaceutical composition can contain, in case of inhalative administration e.g. from 0.001 mg to 10 mg, preferably 0.01 mg to 7.5 mg, more preferably 0.01 mg to 5 mg of the compound of the invention. Administration of the pharmaceutical composition in a single dose per day is preferred.

Combinations

Depending on the particular disease to be treated or prevented, additionally therapeutic agents, which are normally administered to treat or prevent that disease, may optionally be co-administered with the compounds of the invention.

In a preferred embodiment, at least one of the compounds of the invention is co-administered with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics.

In this respect, the "therapeutic agent" includes the corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics in form of the free compounds, the pharmaceutically acceptable salts thereof, the pharmaceutically acceptable derivatives thereof (e.g., but not limited to, ester derivatives, N-oxides etc.), the solvates (hydrates) thereof and the stereoisomers of the compounds, salts, derivatives and solvates.

Co-administration of at least one of the compounds of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics can take place in form of a fixed combination, a non-fixed combination or a kit of parts.

A "fixed combination" is defined as a combination wherein the compound of the invention and the therapeutic agent intended for co-administration are present in one dosing unit or in a single entity. One example of a fixed combination is a pharmaceutical composition wherein the compound of the invention and the therapeutic agent are present in admixture for simultaneous administration. Another example of a fixed combination is a pharmaceutical composition wherein the compound of the invention and the therapeutic compound are present in one dosing unit without being in admixture.

A "non-fixed combination" or "kit of parts" is defined as a combination wherein the compound of the invention and the therapeutic agent are present in more than one dosing unit. In a non-fixed combination or a kit of parts the compound of the invention and the therapeutic agent are provided as separate formulations. They might be packaged and presented together as separate components of a combination pack for simultaneous, sequential or separate use in combination therapy. Simultaneous or sequential administration of the compound of the invention and the therapeutic agent are preferred. In case of sequential or separate administration of the compound of the invention and the therapeutic agent, the compound of the invention can be administered before or after administration of the therapeutic agent.

Sequential administration encompasses a short time period between the administration of the compound of the invention and the therapeutic agent or vice versa (for example, the time that is needed to swallow one tablet after the other).

Separate administration encompasses longer time periods between the administration of the compound of the invention and the therapeutic agent. In a preferred embodiment of the invention, the compound of the invention is administered while the therapeutic agent (or vice versa) still has an therapeutic effect on the patient being treated.

In a particularly preferred embodiment of the invention the co-administration of at least one of the compounds of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics leads to a therapeutic effect that is greater than the sum of the therapeutic effects that will be achieved in case the compound of the invention respectively the additional therapeutic agent are given alone.

The type of formulation of the compound of the invention and the therapeutic agent of a non-fixed combination or a kit of parts can be identical, i.e. both, the compound of the invention and the therapeutic agent are formulated, for example, as powder, solution or suspension suitable for inhalative administration, or can be different, i.e. suited for different administration forms, such as e.g. the compound of the invention is formulated as powder, solution or suspension suitable for inhalative administration and the therapeutic agent is formulated as tablet or capsule for oral administration.

Accordingly, the invention additionally relates to a pharmaceutical composition presented either as a fixed combination, a non-fixed combination or kit of parts comprising at least one of the compounds of the invention, at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, and at least one pharmaceutically acceptable auxiliary.

In a preferred embodiment, the above-mentioned fixed combination, non-fixed combination or kit of parts comprise a compound of the invention (in particular the compound of the invention is one of the examples of the invention or a pharmaceutically acceptable salt thereof), a $\beta_2$-adrenoreceptor agonist and at least one pharmaceutically acceptable auxiliary. In a particularly preferred embodiment, the above-mentioned fixed combination, non-fixed combination or kit of parts comprise:
a compound of the invention and salbutamol,
a compound of the invention and milveterol,
a compound of the invention and indacaterol,
a compound of the invention and carmoterol,
a compound of the invention and salmeterol,
a compound of the invention and formoterol,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride. In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate.

Preferably the β2-adrenoreceptor agonist is a long-acting β2-adrenoreceptor agonist; particularly preferred in this respect are those β2-adrenoreceptor agonists having a therapeutic effect over a 12-24 hours period. Furthermore, the β2-adrenoreceptor agonist is preferably for inhaled administration, for once daily administration and for simultaneous inhaled administration.

Preferably, the combination comprising a compound of the invention and a β2-adrenoreceptor agonist is for the treatment or prophylaxis of bronchial asthma and COPD.

In a preferred embodiment, the above-mentioned fixed combination, non-fixed combination or kit of parts comprise a compound of the invention (in particular the compound of the invention is one of the examples of the invention or a pharmaceutically acceptable salt thereof), a corticosteroid and at least one pharmaceutically acceptable auxiliary. In a particularly preferred embodiment, the above-mentioned fixed combination, non-fixed combination or kit of parts comprise:
a compound of the invention and budesonide,
a compound of the invention and fluticasone,
a compound of the invention and beclometasone,
a compound of the invention and mometasone,
a compound of the invention and triamcinolone acetonide, or
a compound of the invention and ciclesonide,
and at least one pharmaceutically acceptable auxiliary.

In a preferred embodiment, the pharmaceutically acceptable derivative of fluticasone is fluticasone-17-propionate. In another preferred embodiment, the pharmaceutically acceptable derivative of fluticasone is fluticasone-17-furoate. In another preferred embodiment, the pharmaceutically acceptable derivative of beclometasone is beclometasone 17,21-dipropionate ester. In a preferred embodiment, the pharmaceutically acceptable derivative of mometasone is mometasone furoate.

The combination comprising a compound of the invention and a corticosteroid preferably is for the treatment and prophylaxis of bronchial asthma, COPD, allergic rhinitis or a dermatological disease, such as for example atopic dermatitis. Preferably the corticosteroid is used for external topical, intranasal or inhaled administration; in severe cases, the corticosteroid may also be used orally.

In a preferred embodiment, the above-mentioned fixed combination, non-fixed combination or kit of parts comprise a compound of the invention (in particular the compound of the invention is one of the examples of the invention or a pharmaceutically acceptable salt thereof), an anticholinergic and at least one pharmaceutically acceptable auxiliary. In a particularly preferred embodiment, the above-mentioned fixed combination, non-fixed combination or kit of parts comprise:
a compound of the invention and glycopyrronium bromide,
a compound of the invention and aclidinium bromide,
a compound of the invention and tiotropium bromide, or
a compound of the invention and ipratropium bromide,
a compound of the invention and darotropium bromide,
and at least one pharmaceutically acceptable auxiliary.

In a preferred embodiment, the stereoisomer of glycopyrronium bromide is (R,R)-glycopyrronium bromide. In a preferred embodiment, tiotropium bromide is used in form of its monohydrate.

Preferably, the anticholinergic is for inhaled administration. The combination comprising a compound of the invention and an anticholinergic is preferably for the treatment or prophylaxis of COPD.

In a preferred embodiment, the above-mentioned fixed combination, non-fixed combination or kit of parts comprise a compound of the invention (in particular the compound of the invention is one of the examples of the invention), a H1 receptor antagonist and at least one pharmaceutically acceptable auxiliary. In a particularly preferred embodiment, the above-mentioned fixed combination, non-fixed combination or kit of parts comprise:
a compound of the invention and azelastine,
a compound of the invention and olopatadine,
a compound of the invention and loratadine,
a compound of the invention and desloratadine, or
a compound of the invention and cetirizine,
and at least one pharmaceutically acceptable auxiliary.

In a preferred embodiment, the pharmaceutically acceptable salt of azelastine is azelastine hydrochloride. In a preferred embodiment, the pharmaceutically acceptable salt of olapatadine is olapatadine hydrochloride. In a preferred embodiment, the pharmaceutically acceptable salt of cetirizine is cetirizine dihydrochloride. In a preferred embodiment, the stereoisomer of cetirizine is levocetirizine. In another preferred embodiment, the pharmaceutically acceptable salt of levocetirizine is levocetirizine dihydrochloride.

The combination comprising a compound of the invention and a H1 receptor agonist is preferably for the treatment or prophylaxis of allergic rhinitis.

In a preferred embodiment, the above-mentioned fixed combination, non-fixed combination or kit of parts comprise a compound of the invention (in particular the compound of the invention is one of the examples of the invention), a leukotriene receptor antagonist and at least one pharmaceutically acceptable auxiliary. In a particularly preferred embodiment, the above-mentioned fixed combination, non-fixed combination or kit of parts comprise:
a compound of the invention and montelukast,
a compound of the invention and pranlukast, or
a compound of the invention and zafirlukast,
and at least one pharmaceutically acceptable auxiliary.

In a preferred embodiment, the pharmaceutically acceptable salt of montelukast is montelukast sodium. In another preferred embodiment, pranlukast is used in form of its monohydrate.

The combination comprising a compound of the invention and a leukotriene receptor antagonist is preferably for the treatment or prophylaxis of bronchial asthma.

In a preferred embodiment, the above-mentioned fixed combination, non-fixed combination or kit of parts comprise a compound of the invention (in particular the compound of the invention is one of the examples of the invention or a pharmaceutically acceptable salt thereof), a 5-lipoxygenase inhibitor and at least one pharmaceutically acceptable auxiliary. In a particularly preferred embodiment, the above-mentioned fixed combination, non-fixed combination or kit of parts comprise:
a compound of the invention and zileuton,
and at least one pharmaceutically acceptable auxiliary.

The combination comprising a compound of the invention and a 5-lipoxygenase inhibitor is preferably for the treatment or prophylaxis of bronchial asthma.

In a preferred embodiment, the above-mentioned fixed combination, non-fixed combination or kit of parts comprise a compound of the invention (in particular the compound of the invention is one of the examples of the invention), a type 5 phosphodiesterase inhibitor and at least one pharmaceutically acceptable auxiliary. In a particularly preferred embodiment, the above-mentioned fixed combination, non-fixed combination or kit of parts comprise:
a compound of the invention and sildenafil,
a compound of the invention and vardenafil,
a compound of the invention and tadalafil,
a compound of the invention and udenafil, or
a compound of the invention and avanafil,
and at least one pharmaceutically acceptable auxiliary.

In another preferred embodiment, the pharmaceutically acceptable salts of sildenafil are sildenafil hemi-citrate, sildenafil citrate and sildenafil mesilate; particularly preferred is the citrate salt of sildenafil. In another preferred embodiment, the pharmaceutically acceptable salts of vardenafil are vardenafil hydrochloride or vardenafil dihyrochloride. In another preferred embodiment, the pharmaceutically acceptable salt of avanafil is avanafil besilate.

The combination comprising a compound of the invention and a PDE5 inhibitor is preferably for the treatment or prophylaxis of pulmonary hypertension and COPD.

In a preferred embodiment, the above-mentioned fixed combination, non-fixed combination or kit of parts comprise a compound of the invention (in particular the compound of the invention is one of the examples of the invention or a pharmaceutically acceptable salt thereof), an endothelin antagonist and at least one pharmaceutically acceptable auxiliary. In a particularly preferred embodiment, the above-mentioned fixed combination, non-fixed combination or kit of parts comprise:
a compound of the invention and bosentan,
a compound of the invention and ambrisentan,
a compound of the invention and atrasentan,
a compound of the invention and darusentan,
a compound of the invention and clazosentan, or
a compound of the invention and avosentan,
and at least one pharmaceutically acceptable auxiliary.

In another preferred embodiment, bosentan is used in form of its monohydrate. In another preferred embodiment the pharmaceutically acceptable salt of clazosentan is the disodium salt of clazosentan. In another preferred embodiment the pharmaceutically acceptable salts of atrasentan are atrasentan hydrochloride or the sodium salt of atrasentan. In another preferred embodiment the R-enantiomer of atrasentan is used. In another preferred embodiment the S-enantiomer of darusentan is used.

The combination comprising a compound of the invention and an endothelin antagonist is preferably for the treatment or prophylaxis of pulmonary hypertension and COPD.

In a preferred embodiment, the above-mentioned fixed combination, non-fixed combination or kit of parts comprise a compound of the invention (in particular the compound of the invention is one of the examples of the invention or a pharmaceutically acceptable salt thereof), a HMG-CoA reductase inhibitor and at least one pharmaceutically acceptable auxiliary. In a particularly preferred embodiment, the above-mentioned fixed combination, non-fixed combination or kit of parts comprise:
a compound of the invention and lovastatin,
a compound of the invention and pravastatin,
a compound of the invention and simvastatin,
a compound of the invention and atorvastatin,
a compound of the invention and fluvastatin,
a compound of the invention and rosuvastatin,
a compound of the invention and pitavastatin,
a compound of the invention and bervastatin,
a compound of the invention and dalvastatin, or
a compound of the invention and glenvastatin,
and at least one pharmaceutically acceptable auxiliary.

In a preferred embodiment the pharmaceutically acceptable salts of pravastatin are the potassium, lithium, sodium and hemi-calcium salt of pravastatin. A particularly preferred pharmaceutically acceptable salt of pravastatin is the sodium salt of pravastatin. In a preferred embodiment the pharmaceutically acceptable salt of simvastatin is the sodium salt of simvastatin. In a preferred embodiment the pharmaceutically acceptable salts of atorvastatin are the potassium, sodium and the hemi-calcium salt of atorvastatin. A particularly preferred pharmaceutically acceptable salt of atorvastatin is the hemi-calcium salt of atorvastatin. As an example for a hydrate of atorvastatin may be mentioned the trihydrate and the sesquihydrate of the hemi-calcium salt of atorvastatin. In a preferred embodiment of the pharmaceutically acceptable salt of fluvastatin is the sodium salt of fluvastatin. In a preferred embodiment the pharmaceutically acceptable salts of rosuvastatin are the potassium, lithium, sodium, hemi-magnesium and the hemi-calcium salt of rosuvastatin. A particularly preferred pharmaceutically acceptable salt of rosuvastatin is the hemi-calcium salt of rosuvastatin. Another particularly preferred pharmaceutically acceptable salt of rosuvastatin is the sodium salt of rosuvastatin. In a preferred embodiment the pharmaceutically acceptable salts of pitavastatin are the potassium, sodium and the hemi-calcium salt of pitavastatin. A particularly preferred pharmaceutically acceptable salt of pitavastatin is the hemi-calcium salt of pitavastatin.

The combination comprising a compound of the invention and a HMG-CoA reductase inhibitor is preferably for the treatment or prophylaxis of COPD.

In a preferred embodiment, the above-mentioned fixed combination, non-fixed combination or kit of parts comprise a compound of the invention (in particular the compound of the invention is one of the examples of the invention), a lung surfactant and at least one pharmaceutically acceptable auxiliary. In a particularly preferred embodiment, the above-mentioned fixed combination, non-fixed combination or kit of parts comprise:
a compound of the invention and lusupultide,
a compound of the invention and poracant alfa,
a compound of the invention and sinapultide,
a compound of the invention and beracant,
a compound of the invention and bovacant,
a compound of the invention and colfosceril palmitate,
a compound of the invention and surfactant-TA, or
a compound of the invention and calfacant,
and at least one pharmaceutically acceptable auxiliary.

The combination comprising a compound of the invention and a lung surfactant is preferably for the treatment or prophylaxis of bronchial asthma or COPD.

In a preferred embodiment, the above-mentioned fixed combination, non-fixed combination or kit of parts comprise a compound of the invention (in particular the compound of the invention is one of the examples of the invention or a pharmaceutically acceptable salt thereof), an antibiotic and at least one pharmaceutically acceptable auxiliary. In a particularly preferred embodiment, the above-mentioned fixed combination, non-fixed combination or kit of parts comprise:
a compound of the invention and amoxicillin,
a compound of the invention and ampicillin,
a compound of the invention and levofloxacin,
a compound of the invention and clarithromycin,
a compound of the invention and ciprofloxacin,
a compound of the invention and telithromycin, or
a compound of the invention and azithromycin,
and at least one pharmaceutically acceptable auxiliary.

In a preferred embodiment, amoxicillin is used in form of its trihydrate. In another preferred embodiment, ampicillin is used in form of its trihydrate. In another preferred embodiment, the pharmaceutically acceptable salt of ampicillin is ampicillin natrium. In another preferred embodiment levofloxacin is used in form of its hemi hydrate. In another preferred embodiment, the pharmaceutically acceptable salt of ciprofloxacin is ciprofloxacin hydrochloride monohydrate. In another preferred embodiment, azithromycin is used in form of its monohydrate.

The combination comprising a compound of the invention and an antibiotic is preferably for the treatment or prophylaxis of exacerbations associated with bronchial asthma and COPD.

In a preferred embodiment, the above-mentioned fixed combination, non-fixed combination or kit of parts comprise a compound of the invention (in particular the compound of the invention is one of the examples of the invention or a pharmaceutically acceptable salt thereof), a corticosteroid, a $\beta_2$-adrenoreceptor agonist and at least one pharmaceutically acceptable auxiliary. In a particularly preferred embodiment, the above-mentioned fixed combination, non-fixed combination or kit of parts comprise:
a compound of the invention, budesonide and salbutamol,
a compound of the invention, budesonide and milveterol,
a compound of the invention, budesonide and indacaterol,
a compound of the invention, budesonide and carmoterol,
a compound of the invention, budesonide and salmeterol,
a compound of the invention, budesonide and formoterol,
a compound of the invention, fluticasone and salbutamol,
a compound of the invention, fluticasone and milveterol,
a compound of the invention, fluticasone and indacaterol,
a compound of the invention, fluticasone and carmoterol,
a compound of the invention, fluticasone and salmeterol,
a compound of the invention, fluticasone and formoterol,
a compound of the invention, beclometasone and salbutamol,
a compound of the invention, beclometasone and milveterol,
a compound of the invention, beclometasone and indacaterol,
a compound of the invention, beclometasone and carmoterol,
a compound of the invention, beclometasone and salmeterol,
a compound of the invention, beclometasone and formoterol,
a compound of the invention, mometasone and salbutamol,
a compound of the invention, mometasone and milveterol,
a compound of the invention, mometasone and indacaterol,
a compound of the invention, mometasone and carmoterol,
a compound of the invention, mometasone and salmeterol,
a compound of the invention, mometasone and formoterol,
a compound of the invention, triamcinolone acetonide and salbutamol,
a compound of the invention, triamcinolone acetonide and milveterol,
a compound of the invention, triamcinolone acetonide and indacaterol,
a compound of the invention, triamcinolone acetonide and carmoterol,
a compound of the invention, triamcinolone acetonide and salmeterol,
a compound of the invention, triamcinolone acetonide and formoterol,
a compound of the invention, ciclesonide and salbutamol,
a compound of the invention, ciclesonide and milveterol,
a compound of the invention, ciclesonide and indacaterol,
a compound of the invention, ciclesonide and carmoterol,
a compound of the invention, ciclesonide and salmeterol, or
a compound of the invention, ciclesonide and formoterol,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention or a pharmaceutically acceptable salt thereof), a $\beta_2$-adrenoreceptor agonist, an anticholinergic and at least one pharmaceutically acceptable auxiliary. In a particularly preferred embodiment, the above-mentioned fixed combination, non-fixed combination or kit of parts comprise:
a compound of the invention, salbutamol and glycopyrronium bromide,
a compound of the invention, salbutamol and aclidinium bromide,
a compound of the invention, salbutamol and tiotropium bromide,
a compound of the invention, salbutamol and ipratropium bromide,
a compound of the invention, salbutamol and darotropium bromide,
a compound of the invention, milveterol and glycopyrronium bromide, a compound of the invention, milveterol and aclidinium bromide,
a compound of the invention, milveterol and tiotropium bromide,
a compound of the invention, milveterol and ipratropium bromide,
a compound of the invention, milveterol and darotropium bromide,
a compound of the invention, salmeterol and glycopyrronium bromide,
a compound of the invention, salmeterol and aclidinium bromide,
a compound of the invention, salmeterol and tiotropium bromide,
a compound of the invention, salmeterol and ipratropium bromide,
a compound of the invention, salmeterol and darotropium bromide,
a compound of the invention, formoterol and glycopyrronium bromide,
a compound of the invention, formoterol and aclidinium bromide,
a compound of the invention, formoterol and tiotropium bromide,
a compound of the invention, formoterol and ipratropium bromide,
a compound of the invention, formoterol and darotropium bromide,
a compound of the invention, indacaterol and glycopyrronium bromide,
a compound of the invention, indacaterol and aclidinium bromide,
a compound of the invention, indacaterol and tiotropium bromide,
a compound of the invention, indacaterol and ipratropium bromide,
a compound of the invention, indacaterol and darotropium bromide,
a compound of the invention, carmoterol and glycopyrronium bromide,
a compound of the invention, carmoterol and aclidinium bromide,
a compound of the invention, carmoterol and tiotropium bromide, or
a compound of the invention, carmoterol and ipratropium bromide,
a compound of the invention, carmoterol and darotropium bromide,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention or a pharmaceutically acceptable salt thereof), a corticosteroid, an anticholinergic and at least one pharmaceutically acceptable auxiliary. In a particularly preferred embodiment, the above-mentioned fixed combination, non-fixed combination or kit of parts comprise:
a compound of the invention, budesonide and glycopyrronium bromide,
a compound of the invention, budesonide and aclidinium bromide,
a compound of the invention, budesonide and tiotropium bromide,
a compound of the invention, budesonide and ipratropium bromide,
a compound of the invention, budesonide and darotropium bromide,
a compound of the invention, fluticasone and glycopyrronium bromide,
a compound of the invention, fluticasone and aclidinium bromide,
a compound of the invention, fluticasone and tiotropium bromide,
a compound of the invention, fluticasone and ipratropium bromide,
a compound of the invention, fluticasone and darotropium bromide,
a compound of the invention, beclometasone and glycopyrronium bromide,
a compound of the invention, beclometasone and aclidinium bromide,
a compound of the invention, beclometasone and tiotropium bromide,
a compound of the invention, beclometasone and ipratropium bromide,
a compound of the invention, beclometasone and darotropium bromide,
a compound of the invention, mometasone and glycopyrronium bromide,
a compound of the invention, mometasone and aclidinium bromide,
a compound of the invention, mometasone and tiotropium bromide,
a compound of the invention, mometasone and ipratropium bromide,
a compound of the invention, mometasone and darotropium bromide,
a compound of the invention, triamcinolone acetonide and glycopyrronium bromide,
a compound of the invention, triamcinolone acetonide and aclidinium bromide,
a compound of the invention, triamcinolone acetonide and tiotropium bromide,
a compound of the invention, triamcinolone acetonide and ipratropium bromide,
a compound of the invention, triamcinolone acetonide and darotropium bromide,
a compound of the invention, ciclesonide and glycopyrronium bromide,
a compound of the invention, ciclesonide and aclidinium bromide,
a compound of the invention, ciclesonide and tiotropium bromide, or
a compound of the invention, ciclesonide and ipratropium bromide,
a compound of the invention, ciclesonide and darotropium bromide,
and at least one pharmaceutically acceptable auxiliary.

The above-mentioned triple combinations may preferably be used in the treatment or prophylaxis of bronchial asthma or COPD.

Exemplary combinations, in particular for external topical administration (for example versus atopic dermatitis or psoriasis), may include a compound of the invention and an immunosuppressant, for example a calcineurin inhibitor, such as pimecrolimus or tacrolimus.

Therefore, in another preferred embodiment, the above-mentioned fixed combination, non-fixed combination or kit of parts comprise a compound of the invention (in particular the compound of the invention is one of the examples of the invention or a pharmaceutically acceptable salt thereof), an immunosuppressant and at least one pharmaceutically acceptable auxiliary. In a particularly preferred embodiment, the above mentioned fixed combination, non-fixed combination or kit of parts comprise:

a compound of the invention and pimecrolimus,
a compound of the invention and tacrolimus,
a compound of the invention and methotrexate,
a compound of the invention and ascomycin, or
a compound of the invention and cyclosporin A,
and at least one pharmaceutically acceptable auxiliary.

The externally topically administrable immunosuppressant can be administered or administrable in a external-topical composition separately from the compound of the invention (non-fixed combination or kit of parts) or it can be contained with the compound of the invention in a combined externally-topically administrable composition (fixed combination). In a preferred embodiment the externally topically administrable composition is a cream containing pimecrolimus at ca. 1% w/w concentration. In another preferred embodiment the externally topically administrable composition is an ointment containing tacrolimus at from about 0.03% to about 0.1% w/w concentration).

Other combinations for external topical administration, in particular for the treatment or prophylaxis of atopic dermatitis and psoriasis, may include a compound of the invention and a corticosteroid. Beside the corticosteroid combinations mentioned above also the following corticosteroid combinations may be useful.

In another preferred embodiment, the above-mentioned fixed combination, non-fixed combination or kit of parts comprise a compound of the invention (in particular the compound of the invention is one of the examples of the invention or a pharmaceutically acceptable salt thereof), a corticosteroid and at least one pharmaceutically acceptable auxiliary. In a particularly preferred embodiment, the above mentioned fixed combination, non-fixed combination or kit of parts comprise:

a compound of the invention and prednisolone,
a compound of the invention and dexamethasone,
a compound of the invention and betamethasone, or
a compound of the invention and hydrocortisone,
and at least one pharmaceutically acceptable auxiliary.

In another preferred embodiment, the above-mentioned corticosteroids are used in form of an ester, such as, for example, prednisolone valerate acetate, hydrocortisone butyrate, hydrocortisone acetate, dexamethasone valerate, dexamethasone propionate, dexamethasone dipropionate, betamethasone butyrate propionate or prednisolone valerate acetate.

Further combinations for external topical combination, in particular for the treatment of psoriasis, may include a compound of the invention and a vitamin D analogue.

Therefore, in another preferred embodiment the above-mentioned fixed combination, non-fixed combination or kit of parts comprise a compound of the invention (in particular the compound of the invention is one of the examples of the invention or a pharmaceutically acceptable salt thereof), a vitamin D analogue and at least one pharmaceutically acceptable auxiliary. In a particularly preferred embodiment, the above mentioned fixed combination, non-fixed combination or kit of parts comprise:

a compound of the invention and calcitriol,
a compound of the invention and calcipotriol, or
a compound of the invention and tacalcitol,
and at least one pharmaceutically acceptable auxiliary.

In case, both (or all) combination partners—the compound of the invention as well as the therapeutic agent(s)—of the above-defined combinations are both (or all) suitable for inhalative administration, a preferred embodiment of the invention is the simultaneous inhaled administration of both (or all) combination partners by use of a combination inhalation device. Such a combination inhalation device can comprise a combined pharmaceutical composition for simultaneous inhaled administration, the composition comprising both (or all) individual compounds of the particular combination.

In an alternative, the combination inhalation device can be such that the individual compounds of the particular combination are administrable simultaneously but are stored separately (or wholly or partly separated for triple combinations), for example in separate pharmaceutical compositions.

In case of non-fixed combinations or kit of parts comprising at least one of the compounds of the invention and at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, the compound of the invention and the therapeutic agent may be administered by the same route, e.g., without limitation, by inhalation (or external topical), or by different routes, e.g., without limitation, the compound of the invention may be, for example, administered by inhalation and the therapeutic agent may be administered orally.

In case of co-administration of at least one compound of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, in form of a fixed combination, non-fixed combination or kit of parts the dose of the compound of the invention as well as the dose of the therapeutic agent will be in a range customary for the monotherapy, it more likely being possible, on account of the individual action, which are mutually positively influencing and reinforcing, to reduce the respective doses in case of co-administration of the compound(s) of the invention and the therapeutic agent.

In case of co-administration of at least one compound of the invention and at least one therapeutic compound selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, in form of a fixed combination, a non-fixed combination or a kit of parts a single dose unit of the respective pharmaceutical composition/formulation can contain, in case of oral or parenteral administration 0.01 mg to 250 mg, preferably 0.05 mg to 100 mg, more preferably 0.05 mg to 10 mg, or in case of nasal or inhalative administration 0.001 mg to 10 mg, preferably 0.01 mg to 7.5 mg, more preferably 0.01 mg to 5 mg of the compound of the invention and from 0.01 mg to 4000 mg, preferably 0.1 mg to 2000 mg, more preferably 0.5 mg to 1000 mg, most preferably 1 mg to 500 mg, of the therapeutic agent, depending on the therapeutic agent being used the disease to be treated and the administration route selected. Preferably, the at least one compound of the invention and the at least one therapeutic agent are present in the pharmaceutical compositions/formulations in a weight ratio of from 1000:1 to 1:1000, more preferably in a weight ratio of from 100:1 to 1:100, even more preferably in a weight ratio of from 25:1 to 1:25.

Biological Investigations

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (J E Souness et al., Immunopharmacology 47: 127-162, 2000).

The antiinflammatory potential of PDE4 inhibitors in vivo in various animal models has been described (M M Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therap 12: 377-386, 1999). In addition, the immunomodulatory potential of PDE4 inhibitors is evident from the inhibition of T-cell responses like cytokine synthesis or proliferation (D M Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Method for Measuring Inhibition of PDE4 Activity

The PDE4B1 (GB no. L20966) was a gift of Prof. M. Conti (Stanford University, USA). It was amplified from the original plasmid (pCMV5) via PCR with primers Rb18 (5'-CAGACATCCTAAGAGGGGAT-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B1 was expressed in SF21 cells by infecting $2 \times 10^6$ cells/ml with an MOI (multiplicity of infection) between 1 and 10 in the serum-free medium Insect Express Sf9-S2 (PAA, Pasching, Austria). The cells were cultured at 28° C. for 48-72 hours, after which they were pelleted for 5-10 min at 1000×g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B1 activity was inhibited by the compounds according to the invention in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg/ml of BSA, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDE investigated. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE4B1 activity are determined from the concentration-effect curves by means of non-linear regression.

For the following compounds inhibitory values [measured as $-\log IC_{50}$ (mol/l)] higher than 8.0 have been determined. The numbers of the compounds correspond to the numbers of the examples.

Compounds 1-3, 6, 7, 8, 9, 10, 11, 13-15, 18-22, 25, 28-32, 34-39, 42, 43, 45, 46, 48-65, 66, 67, 68-82, 84-97, 98-101, 103-111, 114, 116-117, 119-145, 147-149, 150-160, 163-166, 168-172

In Vivo Assay: LPS-Induced Pulmonary Inflammation Model in Rats (Method A)

Introduction

Exposure of rats to aerosolized lipopolysaccharide (LPS) causes a pulmonary mainly neutrophilic inflammation, which can be assessed by bronchoalveolar lavage (BAL). LPS-induced pulmonary inflammation models are robust and are commonly used for the evaluation of test compounds modulating the immediate immune response. Phosphodiesterase-4 inhibitors are administered by intratracheal dry powder insufflation 2 h prior nose-only LPS challenge in rats. The antiinflammatory activity of the phosphodiesterase inhibitors is assessed based on pulmonary total leukocyte and neutrophil counts in the bronchoalveolar lavage fluid 16 h after LPS exposure.

Materials and Methods

Animals

Male Sprague Dawley rats weighing 250-300 g are used. Rats are delivered 1 weak prior to the experiments and have free access to water and food.

Intratracheal Dry Powder Insufflation

Compound Blending

The test compound in crystalline and micronized state is blended with lactose for inhalation ad 10 mg/kg (Respitose® SV003, DMV International, Netherlands). Respitose® and test compound are transferred to 12 ml tubes and are blended for 10 min. Dilution series are prepared from the this stock blend.

Compound Insufflation Technique

A device consisting of an Abbocath®-T catheter (18 G×51 mm), a one-way stop-cock and a 5 ml syringe is used for test compound insufflation. Weighed test compound blends are directly filled in the stop-cocks. Intubation of the rats is guided by sight and is done under a short time halothane anesthesia.

Compound Dosing

The administered dose of the blended material is 10 mg/kg. The expected material loss in the device is 25%, therefore the weighted dose used is 12.5 mg/kg. One day before the experiment the rat body weights are documented and the mean body weight is used to calculate the administered blend dose per rat. LPS challenged and unchallenged control animals received drug-free Respitose® as placebo. Test compound blends and Respitose are administered 2 h prior LPS challenge.

LPS Challenge

Conscious and restrained animals are connected to a nose-only exposure system (CR equipment SA, Tannay, Switzerland) and are exposed to the LPS aerosol for 30 min. The LPS-containing aerosol is generated using a compressed air driven medication nebulizer device (OCTURNO Medizintechnik GmbH, Germany). The LPS solution (E. coli, Serotype 055B5, Art.# L2880, Lot# 114K4103, Sigma-Aldrich; 0.15 mg/ml, diluted in 0.1% hydroxylamine/PBS) is continuously delivered by a syringe pump (20 ml/h) to the nebulizer device. The aerosol is dispersed and transported to the exposure tower by admixture of compressed air. All rats except negative controls are exposed to LPS.

Bronchoalveolar Lavage

Sixteen hours after LPS challenge, animals are sacrificed with Trapanal (thiopental, 350 mg/rat, 2 ml/rat, i.p.), the final body weights are determined and BALs are performed. For the BAL the trachea is exposed and cannulated, followed by gently lavaging the lungs three times in situ with 4 ml PBS buffer.

Total and Differential Cell Counts

Determination of total leukocyte and neutrophil counts in BALF is performed with an automated leukocyte differentiation system (XT-2000iV, Sysmex, Norderstedt, Germany).

Data Analysis

Suppression of LPS-induced total cell and neutrophil influx into the lungs is calculated in % using the means of the cell counts of each treatment group in relation to the control groups:

$$\text{effect on cell influx [\%]} = \frac{(\text{mean}_{treatment\ group} - \text{mean}_{negative\ control})}{(\text{mean}_{positive\ control} - \text{mean}_{negative\ control})} \times 100 - 100$$

Statistical analysis is performed on the primary cell count data using one-way ANOVA and Dunnett's multiple comparison post test vs. positive control. The Grubbs test is used to detect outliers.

Exemplary Results for Compounds Tested Using Method A (the Numbers of the Compounds Correspond to the Numbers of the Examples):

The compounds 2, 9, 11, 14, 18, 65, 68, 69, 70, 72, 84, 85, 90, 94, 96 and 97 showed at a dosage of 1 mg/kg a reduction in the range of 22 to 60% of the total cell count, respectively a reduction in the range of 15 to 53% of neutrophils in comparison to the placebo group.

In Vivo Assay: LPS-Induced Pulmonary Inflammation Model in Rats (Method B)

Introduction

Exposure of rats to aerosolized lipopolysaccharide (LPS) causes a pulmonary mainly neutrophilic inflammation, which can be assessed by bronchoalveolar lavage (BAL). LPS-induced pulmonary inflammation models are robust and are commonly used for the evaluation of test compounds modulating the immediate immune response. Selective phosphodiesterase-4 inhibitors are administered by intratracheal insufflation 1 h prior nose-only LPS challenge in rats. The anti-inflammatory activity of the selective phosphodiesterase inhibitors is assessed based on pulmonary total leukocyte and neutrophil counts in the bronchoalveolar lavage fluid 4 h after LPS exposure.

Materials and Methods

Animals

Male Sprague Dawley rats weighing 250-300 g are used. Rats are delivered 1 weak prior to the experiments and have free access to water and food.

Intratracheal Compound Instillation

Compound Preparation

The test compound in crystalline and micronized state is suspended in Aqua ad injectabilia (Braun, Melsungen, Germany) supplemented with 0.02% Tween20 (Sigma-Aldrich, Schnelldorf, Germany) for intratracheal instillation. Suspensions of test compound are treated in an ultrasonic bath to shear agglomerates and to obtain homogenous suspensions. The aimed doses are prepared by dilution series from the stock suspension, which is prepared for the administration of the highest dose in each experiment.

Compound Instillation Technique

The compound suspension is administered intratracheally using the Microsprayer® device (Penn Century Inc., USA)). The rats are intubated by inserting the Microsprayer needle into the trachea. The length of the microsprayer needle is adjusted to avoid disruption of the tracheal bifurcation. The intubation is guided by sight and is done under a short time isoflurane anesthesia. The suspension is then instilled into the lungs.

Compound Dosing

The administered volume of the compound suspension is 0.5-1 ml/kg. A day before the experiment the rat body weights are documented to calculate the volume to be administered. LPS challenged and unchallenged control animals received drug-free Aqua/Tween20 solution as placebo. Test compounds and placebo are administered 1 h prior to LPS challenge.

LPS Challenge

Conscious and restrained animals are connected to a nose-only exposure system (CR equipment SA, Tannay, Switzerland) and are exposed to the LPS aerosol for 30 min. The LPS-containing aerosol is generated using a compressed air driven medication nebulizer device (Pari LC Sprint Star, Pari GmbH, Starnberg, Germany). The LPS solution (E. coli, Serotype 055B5, Art.# L2880, Lot# L048K4126, Sigma-Aldrich, 1 mg/ml diluted in PBS) is prepared 30 minutes in advance. The aerosol is dispersed and transported to the exposure tower by a sheath air flow of 600 l/h. All rats except negative controls are exposed to LPS.

Bronchoalveolar Lavage 4 hours after LPS challenge, animals are anesthetized by isoflurane and sacrificed by cervical dislocation. BALs are performed. For the BAL the trachea is exposed and cannulated, followed by gently lavaging the lungs two times in situ with 4 ml PBS buffer supplemented with 0.5% Bovine Serum Albumin (Serve, Darmstadt, Germany).

Total and Differential Cell Counts

Determination of total leukocyte and neutrophil counts in BALF is performed with an automated leukocyte differentiation system (XT-2000iV, Sysmex, Norderstedt, Germany).

Data Analysis

The baseline correction is done for each sample according to the formula:

Baseline-corrected cell count value=cell count−Median(negative control group) (5)

All further calculations are performed with the baseline-corrected values.

Effect of compound on LPS-induced total cell and neutrophil influx into the lungs is calculated in % using the medians of the cell counts of each treatment group in relation to the control groups according to the formula:

% effect=$(Y-K)/K*100$

With defining:
Y=Median of the baseline-corrected cell count value of compound-treated group
K=Median of the baseline-corrected cell count value of placebo-treated group Statistical analysis is performed on the primary cell count data using one-way ANOVA and Dunnett's multiple comparison post test vs. positive control. The Grubbs test is used to detect statistical outliers.

Exemplary Results for Compounds Tested Using Method B (the Numbers of the Compounds Correspond to the Numbers of the Examples):

The compounds 12, 16, 24, 38, 45 and 78 showed at a dosage of 1 mg/kg a reduction in the range of 25 to 50% of the total cell count, respectively a reduction in the range of 18 to 47% of neutrophils in comparison to the placebo group.

The invention claimed is:
1. A compound of formula 1

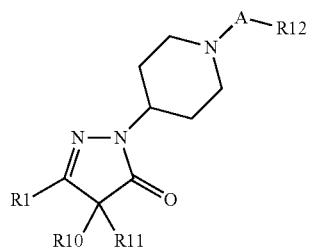

(1)

wherein
R1 represents a phenyl derivative of formulae (a), (b) or (c)

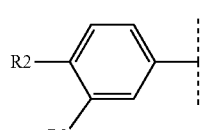

(a)

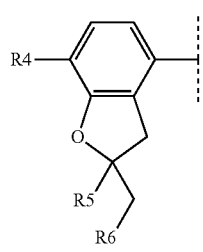

(b)

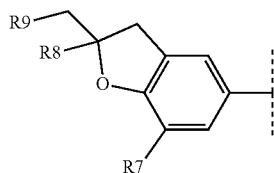

(c)

wherein
R2 is 1-2C-alkoxy or 1-2C-alkoxy which is completely or predominantly substituted by fluorine,
R3 is 1-2C-alkoxy, 3-5C-cycloalkoxy, 3-5C-cycloalkyl-methoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O) or S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20, quinolinyl substituted by R21 or indolyl substituted by R22,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, 2,6-dichlorobenzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl or 1-4C-alkoxycarbonyl-1-4C-alkoxy,
R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, amino, mono- or di-1-4C-alkylamino, piperidinyl or morpholinyl,
R18 is hydrogen, halogen, 1-4C-alkyl or 1-4C-alkoxy,
R19 is halogen, hydroxy, 1-4C-alkyl, 1-4C-alkoxy, amino or mono- or di-1-4C-alkylamino,
R20 is hydrogen, 1-4C-alkyl or 1-4C-alkoxy,
R21 is 1-4C-alkyl,
R22 is 1-4C-Alkyl, or a salt, a stereoisomer or a salt of a stereoisomer of the compound.

2. The compound of formula 1 according to claim 1 wherein

R1 represents a phenyl derivative of formulae (a), (b) or (c)

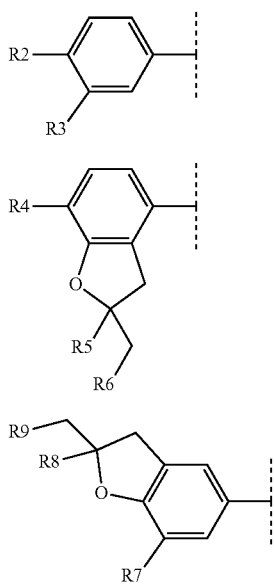

wherein
R2 is 1-2C-alkoxy or 1-2C-alkoxy which is completely or predominantly substituted by fluorine,
R3 is 1-2C-alkoxy, 3-5C-cycloalkoxy, 3-5C-cycloalkylmethoxy or 1-2C-alkoxy which is completely or predominantly substituted by fluorine,
R4 is 1-2C-alkoxy or 1-2C-alkoxy which is completely or predominantly substituted by fluorine;
R5 is 1-2C-alkyl and
R6 is hydrogen or 1-2C-alkyl,
or R5 and R6 together and with inclusion of the two carbon atoms, to which they are bonded, form a spiro-linked 5- or 6-membered hydrocarbon ring,
R7 is 1-2C-alkoxy or 1-2C-alkoxy which is completely or predominantly substituted by fluorine,
R8 is 1-2C-alkyl and
R9 is hydrogen or 1-2C-alkyl,
or R8 and R9 together and with inclusion of the two carbon atoms, to which they are bonded, form a spiro-linked 5- or 6-membered hydrocarbon ring,
R10 is 1-3C-alkyl and
R11 is 1-3C-alkyl,
or R10 and R11 together with the carbon atom, to which they are bonded, form a spiro-linked 3-, 4-, 5- or 6-membered hydrocarbon ring,
A is C(O) or S(O)$_2$,
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16 or pyridinyl substituted by R17 and R18,
wherein
R13 is halogen, cyano, hydroxy, hydroxycarbonyl, 1-4C-alkyl, trifluoromethyl, 1-4C-alkoxy, 1-4C-alkoxy which is completely or predominantly substituted by fluorine, 3-7C-cycloalkyloxy, 3-7C-cycloalkylmethoxy, benzyloxy, amino, mono- or di-1-4C-alkylamino, aminocarbonyl, mono- or di-1-4C-alkylaminocarbonyl, aminocarbonyl-1-4C-alkoxy, 1-4C-alkylcarbonylamino, 1-4C-alkylcarbonyloxy, 1-4C-alkoxycarbonyl, or 1-4C-alkoxycarbonyl-1-4C-alkoxy,
R14 is hydrogen, halogen, 1-4C-alkyl, 1-4C-alkoxy, 1-4C-alkoxy which is completely or predominantly substituted by fluorine, 1-4C-alkoxycarbonyl, amino or mono- or di-1-4C-alkylamino,
R15 is hydrogen, halogen or 1-4C-alkyl,
R16 is hydrogen or 1-4C-alkyl,
R17 is halogen, 1-4C-alkyl, trifluoromethyl, 1-4C-alkoxy, amino, mono- or di-1-4C-alkylamino, piperidinyl or morpholinyl,
R18 is hydrogen, halogen, 1-4C-alkyl or 1-4C-alkoxy,
or a salt, a stereoisomer or a salt of a stereoisomer of the compound.

3. The compound of formula 1 according to claim 1 wherein

R1 represents a phenyl derivative of formulae (a), (b) or (c)

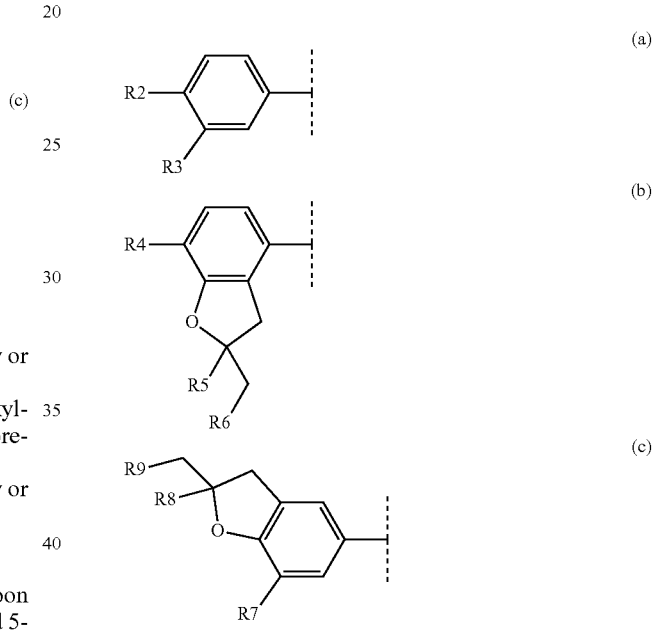

wherein
R2 is methoxy, ethoxy or difluoromethoxy,
R3 is methoxy, ethoxy or cyclopropylmethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy
R8 is methyl,
R9 is hydrogen,
R10 is methyl or ethyl,
R11 is methyl, ethyl or propyl,
or R10 and R11 together with the carbon atom, to which they are bonded, form a spiro-linked cyclopentane ring,
A is C(O),
R12 is phenyl, naphthalenyl, pyridinyl, quinolinyl, isoquinolinyl, quinoxalinyl, 1,6-naphthyridinyl, 1,8-naphthyridinyl, indolyl, phenyl substituted by R13, R14, R15 and R16, pyridinyl substituted by R17 and R18, naphthalenyl substituted by R19 and R20 or quinolinyl substituted by R21, wherein
R13 is fluorine, chlorine, bromine, hydroxy, 1-2C-alkyl, trifluoromethyl, 1-4C-alkoxy, 1-4C-alkoxy which is completely or predominantly substituted by fluorine, cyclopentyloxy, cyclopropylmethoxy, benzyloxy, 2,6-dichlorobenzyloxy, amino, di-1-2C-alkylamino, aminocarbonylmethoxy, 1-2C-alkylcarbonylamino, 1-2C-alkylcarbonyloxy, 1-2C-alkoxycarbonyl or 1-2C-alkoxycarbonylmethoxy,
R14 is hydrogen, fluorine, chlorine, amino, 1-2C-alkyl, 1-2C-alkoxy or 1-2C-alkoxy which is completely or predominantly substituted by fluorine,
R15 is hydrogen, chlorine or 1-2C-alkyl,
R16 is hydrogen or 1-2C-alkyl,
R17 is fluorine, chlorine, 1-2C-alkyl, trifluoromethyl, 1-2C-alkoxy, di-1-2C-alkylamino, piperidinyl or morpholinyl,
R18 is hydrogen, fluorine, 1-2C-alkyl or 1-2C-alkoxy,
R19 is bromine, 1-2C-alkyl, 1-2C-alkoxy, di-1-2C-alkylamino,
R20 is hydrogen, 1-2C-alkyl or 1-2C-alkoxy,
R21 is 1-2C-alkyl,
or a salt, a stereoisomer or a salt of a stereoisomer of the compound.

4. The compound of formula 1 according to claim 1 wherein
R1 represents a phenyl derivative of formulae (a), (b) or (c)

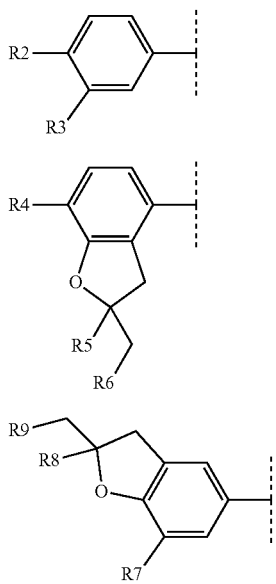

wherein
R2 is methoxy,
R3 is methoxy or cyclopropylmethoxy,
R4 is methoxy,
R5 is methyl,
R6 is hydrogen,
R7 is methoxy
R8 is methyl,
R9 is hydrogen,
R10 is methyl,
R11 is methyl,
A is C(O),
R12 phenyl, naphthalenyl, pyridinyl, quinolinyl, isoquinolinyl, quinoxalinyl, 1,8-naphthyridinyl, 1,6-naphthyridinyl, indolyl, phenyl which is substituted by R13, R14, R15 and R16 or pyridinyl which is substituted by R17 and R18,
wherein
R13 is fluorine, chlorine, bromine, hydroxy, 1-2C-alkyl, trifluoromethyl, 1-4C-alkoxy, 1-4C-alkoxy which is completely or predominantly substituted by fluorine, cyclopentyloxy, cyclopropylmethoxy, benzyloxy, amino, aminocarbonylmethoxy, 1-2C-alkylcarbonylamino, 1-2C-alkylcarbonyloxy, 1-2C-alkoxycarbonyl or 1-2C-alkoxycarbonylmethoxy,
R14 is hydrogen, fluorine, chlorine, amino, 1-2C-alkyl, 1-2C-alkoxy or 1-2C-alkoxy which is completely or predominantly substituted by fluorine,
R15 is hydrogen, chlorine or 1-2C-alkyl,
R16 is hydrogen or 1-2C-alkyl,
R17 is fluorine, chlorine, 1-2C-alkyl, trifluoromethyl, 1-2C-alkoxy, di-1-2C-alkylamino, piperidinyl or morpholinyl,
R18 is hydrogen, fluorine, 1-2C-alkyl or 1-2C-alkoxy,
or a salt of the compound.

5. The compound of formula 1 according to claim 1 wherein
R1 represents a phenyl derivative of formulae (a), (b) or (c)

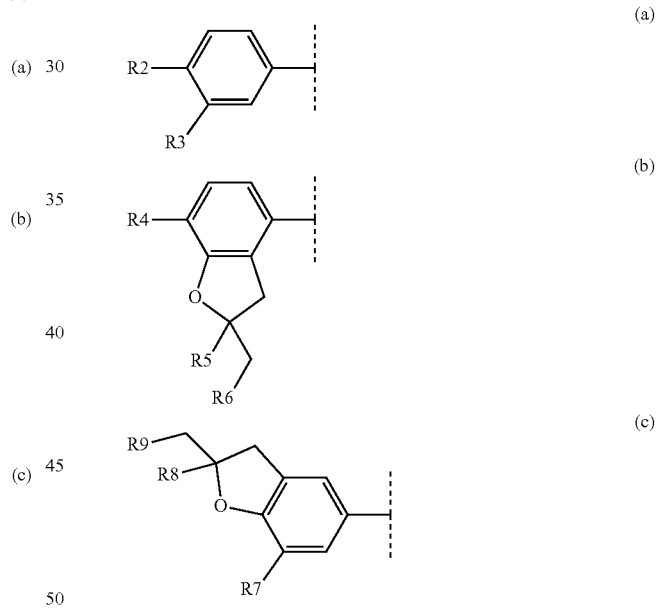

wherein
R2 is methoxy, ethoxy or difluoromethoxy,
R3 is methoxy, ethoxy or cyclopropylmethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy,
R8 is methyl,
R9 is hydrogen,
R10 is methyl or ethyl,
R11 is methyl, ethyl or propyl,
or R10 and R11 together with the carbon atom, to which they are bonded, form a spiro-linked cyclopentane ring, A is C(O), R12 is phenyl, 3-dimethylaminophenyl, 2-ethylphenyl, 3-methylphenyl, 2,5-dimethylphenyl, 2-chloro-5-ethoxyphenyl, 2-chloro-5-isopropoxyphenyl, 3-(acetyloxy)phenyl, 3-methylcarbonylaminophenyl, 2-methyl-4-hydroxyphenyl, 2,4,6-trichlorophenyl, 2-methoxyphenyl, 3-methoxyphenyl, 4-methoxyphenyl, 3-ethoxyphenyl, 3-isopropoxyphenyl, 2,4-dimethoxyphenyl, 3-(2,2,2-trifluoroethoxy)phenyl, 2-trifluoromethoxyphenyl, 3-(cyclopropylmethoxy)-4-(difluoromethoxy)phenyl, 5-cyclopropylmethoxy-2-methyl phenyl, 5-isopropoxy-2-methylphenyl, 5-isopropoxy-2-chlorophenyl, 2,4-dimethoxyphenyl, 2,6-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 5-tert-butoxy-2-methylphenyl, 5-difluoromethoxy-2-methylphenyl, 5-trifluoromethoxy-2-methylphenyl, 2-fluorophenyl, 3-fluorophenyl, 2-chlorophenyl, 3-chlorophenyl, 2-bromophenyl, 2,3-difluorophenyl, 2,6-difluorophenyl, 4-amino-3-trifluoromethylphenyl, 5-amino-2-chlorophenyl, 2-(aminocarbonylmethoxy)phenyl, 5-benzyloxy-2-chlorophenyl, 5-benzyloxy-2-methylphenyl, 5-(2,6-dichlorobenzyl)oxy-2-methylphenyl, 2-methoxycarbonylphenyl, 2-(methylcarbonyloxy)phenyl, 3-(methylcarbonyloxy)phenyl, naphthalen-1-yl, naphthalen-2-yl, 1-bromo-naphthalen-1-yl, 8-bromo-naphthalen-1-yl, 2-methyl-naphthalen-1-yl, 6-hydroxy-naphthalen-1-yl, 1-methoxy-naphthalen-2-yl, 2-methoxy-naphthalen-1-yl, 3-methoxy-naphthalen-2-yl, 4,7-dimethoxy-naphthalen-2-yl, 4-(dimethylamino)-naphthalen-1-yl, 4-(trifluoromethyl)pyridin-3-yl, 2-methoxypyridin-3-yl, 3-chloropyridin-4-yl, 3,5-difluoropyridin-2-yl, 3-methylpyridin-2-yl, 2,6-dimethoxypyridin-3-yl, 2-(piperidin-1-yl)pyridin-4-yl, 2-(morpholin-4-yl)pyridin-4-yl, quinolin-2-yl, quinolin-4-yl, quinolin-5-yl, quinolin-6-yl, quinolin-7-yl, quinolin-8-yl, 4-methyl-quinolin-2-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl, or a salt, a stereoisomer or a salt of a stereoisomer of the compound.

6. The compound of formula 1 according to claim 1 wherein

R1 represents a phenyl derivative of formulae (a), (b) or (c)

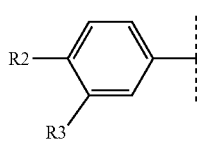

(a)

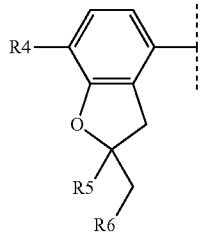

(b)

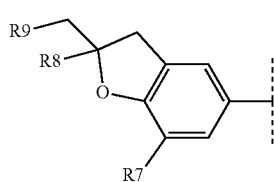

(c)

wherein
R2 is methoxy,
R3 is methoxy,
R4 is methoxy,
R5 is methyl,
R6 is hydrogen,
R7 is methoxy,
R8 is methyl,
R9 is hydrogen,
R10 is methyl,
R11 is methyl,
A is C(O),
R12 is 2,4,6-trichlorophenyl, 2-methoxyphenyl, 3-methoxyphenyl, 3-ethoxyphenyl, 3-isopropoxyphenyl, 3-(2,2,2-trifluoroethoxy)phenyl, 3-(cyclopropylmethoxy)-4-(difluoromethoxy)phenyl, 5-isopropoxy-2-methylphenyl, 2,4-dimethoxyphenyl, 2-cyclopentyloxyphenyl, 2-hydroxyphenyl, 3-hydroxyphenyl, 2-fluoro-5-hydroxyphenyl, 2-chloro-5-hydroxyphenyl, 2-chloro-5-(methylcarbonylamino)phenyl, 5-hydroxy-2-methylphenyl, 3-fluorophenyl, 3-chlorophenyl, 4-amino-3-trifluoromethylphenyl, 5-amino-2-chlorophenyl, 2-(aminocarbonylmethoxy)phenyl, 5-benzyloxy-2-methylphenyl, 2-methoxycarbonylphenyl, 2-(methylcarbonyloxy)phenyl, 3-(methylcarbonyloxy)phenyl, naphthalen-1-yl, 4-(trifluoromethyl)pyridin-3-yl, 2-methoxypyridin-3-yl, 3-chloropyridin-4-yl, 3,5-difluoropyridin-2-yl, 3-methylpyridin-2-yl, 2,6-dimethoxypyridin-3-yl, 2-(piperidin-1-yl)pyridin-4-yl, 2-(morpholin-4-yl)pyridin-4-yl, quinolin-2-yl, quinolin-4-yl, quinolin-5-yl, quinolin-6-yl, quinolin-7-yl, quinolin-8-yl, isoquinolin-1-yl, isoquinolin-4-yl, isoquinolin-5-yl, 1,8-naphthyridin-2-yl, 1,6-naphthyridin-5-yl, 1H-indol-2-yl, 1H-indol-4-yl, 1H-indol-5-yl, 1H-indol-6-yl, 1H-indol-7-yl or quinoxalin-2-yl;

or a salt of the compound.

7. The compound of formula 1 according to claim 1 wherein
R1 represents a phenyl derivative of formulae (a), (b) or (c)

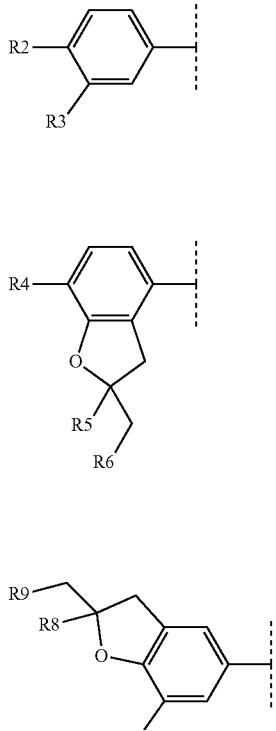

wherein
R2 is methoxy or difluoromethoxy,
R3 is methoxy or cyclopropylmethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy,
R8 is methyl,
R9 is hydrogen,
R10 is methyl or ethyl,
R11 is methyl, ethyl or propyl,
or R10 and R11 together with the carbon atom, to which they are bonded, form a spiro-linked cyclopentane ring,
A is S(O)$_2$,
R12 is phenyl, naphthalenyl, quinolinyl, indolyl, phenyl which is substituted by R13, R14, R15 and R16 or indolyl substituted by R22,
wherein
R13 is fluorine, chlorine, bromine, cyano, hydroxycarbonyl, 1-4C-alkyl, trifluoromethyl, 1-2C-alkoxycarbonyl, 1-2C-alkoxy or 1-2C-alkoxy which is completely or predominantly substituted by fluorine,
R14 is hydrogen, chlorine, 1-4C-alkyl, 1-2C-alkoxy or 1-2C-alkoxycarbonyl;
R15 is hydrogen or 1-4C-alkyl,
R16 is hydrogen or 1-2C-alkyl,
R22 is 1-2C-alkyl,
or a salt, a stereoisomer or a salt of a stereoisomer of the compound.

8. The compound of formula 1 according to claim 1 wherein
R1 represents a phenyl derivative of formulae (a), (b) or (c)

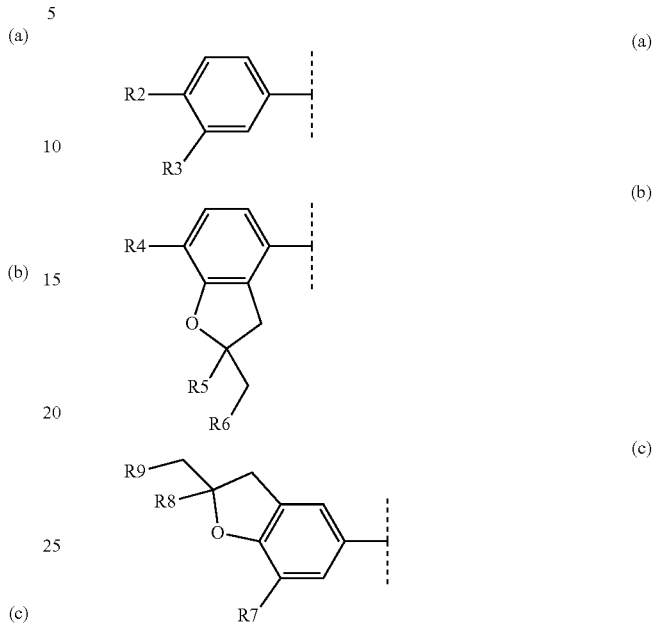

wherein
R2 is methoxy,
R3 is methoxy,
R4 is methoxy,
R5 is methyl,
R6 is hydrogen,
R7 is methoxy,
R8 is methyl,
R9 is hydrogen,
R10 is methyl,
R11 is methyl,
or R10 and R11 together with the carbon atom, to which they are bonded, form a spiro-linked cyclopentane ring,
A is S(O)$_2$,
R12 is phenyl, naphthalenyl, quinolinyl, or phenyl which is substituted by R13, R14, R15 and R16,
wherein
R13 is fluorine, chlorine, bromine, cyano, hydroxycarbonyl, 1-4C-alkyl, trifluoromethyl, 1-2C-alkoxycarbonyl, 1-2C-alkoxy or 1-2C-alkoxy which is completely or predominantly substituted by fluorine,
R14 is hydrogen, chlorine, 1-4C-alkyl, 1-2C-alkoxy or 1-2C-alkoxycarbonyl;
R15 is hydrogen or 1-4C-alkyl,
R16 is hydrogen or 1-2C-alkyl,
or a salt of the compound.

9. The compound of formula 1 according to claim 1 wherein
R1 represents a phenyl derivative of formulae (a), (b) or (c)

-continued

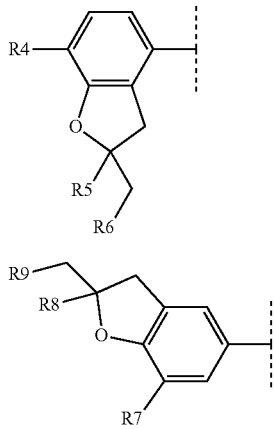

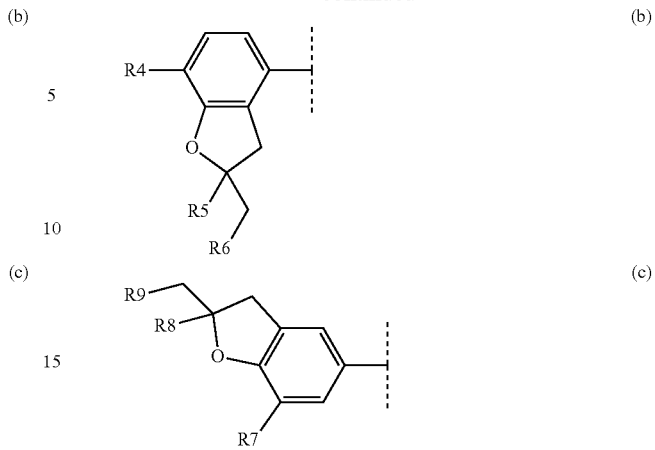

wherein
R2 is methoxy or ethoxy,
R3 is methoxy or ethoxy,
R4 is methoxy,
R5 is methyl,
R6 is hydrogen,
or R5 and R6 together and with inclusion of the two carbon atoms, to which they are bonded, form a spiro-linked cyclopentane ring,
R7 is methoxy,
R8 is methyl,
R9 is hydrogen,
R10 is methyl and
R11 is methyl, ethyl or propyl,
or R10 and R11 together with the carbon atom, to which they are bonded, form a spiro-linked cyclopentane ring,
A is S(O)$_2$,
R12 is phenyl, 2-cyanophenyl, 2-fluorophenyl, 2-bromophenyl, 2-chlorophenyl, 4-chlorophenyl, 2,5-dichlorophenyl, 2,3-dichlorophenyl, 2,4-dichlorophenyl, 3,5-dichlorophenyl, 2,6-dichlorophenyl, 3-chloro-4-fluorophenyl, 4-fluoro-2-methylphenyl, 2-chloro-4-trifluoromethylphenyl, 2-methylphenyl, 3-methylphenyl, 4-methylphenyl, 4-isopropylphenyl, 2-trifluoromethylphenyl, 3-trifluoromethylphenyl, 2,3,5,6-tetramethylphenyl, 2,4,6-triisopropylphenyl, 2-trifluoromethoxyphenyl, 2,5-dimethoxyphenyl, 5-chloro-2-methoxyphenyl, 3-(methoxycarbonyl)phenyl, 3,5-bis-(methoxycarbonyl)phenyl, naphthalen-1-yl, naphthalen-2-yl, 1-methyl-1H-indol-4-yl, 1-methyl-1H-indol-5-yl or quinolin-8-yl,
or a salt, a stereoisomer or a salt of a stereoisomer of the compound.

10. The compound of formula 1 according to claim 1 wherein
R1 represents a phenyl derivative of formulae (a), (b) or (c)

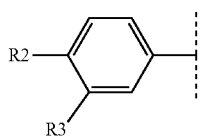

wherein
R2 is methoxy,
R3 is methoxy,
R4 is methoxy,
R5 is methyl,
R6 is hydrogen,
R7 is methoxy,
R8 is methyl,
R9 is hydrogen,
R10 is methyl,
R11 is methyl,
A is S(O)$_2$,
R12 is phenyl, 2-cyanophenyl, 2-fluorophenyl, 2-bromophenyl, 2-chlorophenyl, 4-chlorophenyl, 2,5-dichlorophenyl, 2-methylphenyl, 3-methylphenyl, 4-methylphenyl, 2-trifluoromethylphenyl, 2,3,5,6-tetramethylphenyl, 2,4,6-triisopropylphenyl, 4-methoxyphenyl, 2-trifluoromethoxyphenyl, 2,5-dimethoxyphenyl, 3-(methoxycarbonyl)phenyl, 3,5-bis-(methoxycarbonyl)phenyl, naphthalen-1-yl, naphthalen-2-yl or quinolin-8-yl,
or a salt of the compound.

11. The compound according to claim 1 selected from the group consisting of
2-({4-[3-(3,4-Dimethoxyphenyl)-4,4-dimethyl-5-oxo-4,5-dihydro-1H-pyrazol-1-yl]piperidin-1-yl}sulfonyl) benzonitrile;
Methyl 2-({4-[3-(3,4-dimethoxyphenyl)-4,4-dimethyl-5-oxo-4,5-dihydro-1H-pyrazol-1-yl]piperidin-1-yl}sulfonyl)benzoate;
5-(3,4-Dimethoxyphenyl)-4,4-dimethyl-2-{1-[(4-methylphenyl)sulfonyl]piperidin-4-yl}-2,4-dihydro-3H-pyrazol-3-one;
2-{1-[(4-tert-Butylphenyl)sulfonyl]piperidin-4-yl}-5-(3,4-dimethoxyphenyl)-4,4-dimethyl-2,4-dihydro-3H-pyrazol-3-one;
5-(3,4-Dimethoxyphenyl)-2-{1-[(4-methoxyphenyl)sulfonyl]piperidin-4-yl}-4,4-dimethyl-2,4-dihydro-3H-pyrazol-3-one;
5-(3,4-Dimethoxyphenyl)-4,4-dimethyl-2-[1-(quinolin-8-ylsulfonyl)piperidin-4-yl]-2,4-dihydro-3H-pyrazol-3-one;
5-(3,4-Dimethoxyphenyl)-4,4-dimethyl-2-[1-(naphthalen-1-ylsulfonyl)piperidin-4-yl]-2,4-dihydro-3H-pyrazol-3-one;
5-(3,4-Dimethoxyphenyl)-4,4-dimethyl-2-{1-[(2-methylphenyl)sulfonyl]piperidin-4-yl}-2,4-dihydro-3H-pyrazol-3-one;

5-(3,4-Dimethoxyphenyl)-4,4-dimethyl-2-(1-{[2,4,6-tri(propan-2-yl)phenyl]sulfonyl}piperidin-4-yl)-2,4-dihydro-3H-pyrazol-3-one, 5-(3,4-Dimethoxyphenyl)-2-{1-[(2,5-dimethoxyphenyl)sulfonyl]piperidin-4-yl}-4,4-dimethyl-2,4-dihydro-3H-pyrazol-3-one;

5-(3,4-Dimethoxyphenyl)-4,4-dimethyl-2-{1-[(3-methylphenyl)sulfonyl]piperidin-4-yl}-2,4-dihydro-3H-pyrazol-3-one;

3-({4-[3-(3,4-Dimethoxyphenyl)-4,4-dimethyl-5-oxo-4,5-dihydro-1H-pyrazol-1-yl]piperidin-1-yl}carbonyl)phenyl acetate;

5-(3,4-Dimethoxyphenyl)-4,4-dimethyl-2-[1-(phenylsulfonyl)piperidin-4-yl]-2,4-dihydro-3H-pyrazol-3-one;

5-(3,4-Dimethoxyphenyl)-2-{1-[(2-fluorophenyl)sulfonyl]piperidin-4-yl}-4,4-dimethyl-2,4-dihydro-3H-pyrazol-3-one;

5-(3,4-Dimethoxyphenyl)-4,4-dimethyl-2-(1-{[2-(trifluoromethoxy)phenyl]sulfonyl}piperidin-4-yl)-2,4-dihydro-3H-pyrazol-3-one;

2-{1-[(4-Chlorophenyl)sulfonyl]piperidin-4-yl}-5-(3,4-dimethoxyphenyl)-4,4-dimethyl-2,4-dihydro-3H-pyrazol-3-one;

5-(3,4-Dimethoxyphenyl)-4,4-dimethyl-2-[1-(naphthalen-2-ylsulfonyl)piperidin-4-yl]-2,4-dihydro-3H-pyrazol-3-one;

5-(3,4-Dimethoxyphenyl)-4,4-dimethyl-2-(1-{[2-(trifluoromethyl)phenyl]sulfonyl}piperidin-4-yl)-2,4-dihydro-3H-pyrazol-3-one;

5-(3,4-Dimethoxyphenyl)-4,4-dimethyl-2-{1-[(2,3,5,6-tetramethylphenyl)sulfonyl]piperidin-4-yl}-2,4-dihydro-3H-pyrazol-3-one;

2-{1-[(2-Bromophenyl)sulfonyl]piperidin-4-yl}-5-(3,4-dimethoxyphenyl)-4,4-dimethyl-2,4-dihydro-3H-pyrazol-3-one;

2-{1-[(2,5-Dichlorophenyl)sulfonyl]piperidin-4-yl}-5-(3,4-dimethoxyphenyl)-4,4-dimethyl-2,4-dihydro-3H-pyrazol-3-one;

2-{1-[(2-Chlorophenyl)sulfonyl]piperidin-4-yl}-5-(3,4-dimethoxyphenyl)-4,4-dimethyl-2,4-dihydro-3H-pyrazol-3-one;

5-[3-(Cyclopropylmethoxy)-4-methoxyphenyl]-2-{1-[(2,6-dimethoxyphenyl)carbonyl]-piperidin-4-yl}-4,4-dimethyl-2,4-dihydro-3H-pyrazol-3-one;

Dimethyl 5-({4-[3-(3,4-dimethoxyphenyl)-4,4-dimethyl-5-oxo-4,5-dihydro-1H-pyrazol-1-yl]piperidin-1-yl}sulfonyl)isophthalate;

3-({4-[3-(3,4-Dimethoxyphenyl)-4,4-dimethyl-5-oxo-4,5-dihydro-1H-pyrazol-1-yl]piperidin-1-yl}sulfonyl)benzoic acid;

Methyl 3-({4-[3-(3,4-dimethoxyphenyl)-4,4-dimethyl-5-oxo-4,5-dihydro-1H-pyrazol-1-yl]piperidin-1-yl}sulfonyl)benzoate;

2-({4-[4-(3,4-Dimethoxyphenyl)-1-oxo-2,3-diazaspiro[4.4]non-3-en-2-yl]piperidin-1-yl}sulfonyl)benzonitrile;

2-({4-[3-(7-methoxy-2,2-dimethyl-2,3-dihydro-1-benzofuran-4-yl)-4,4-dimethyl-5-oxo-4,5-dihydro-1H-pyrazol-1-yl]piperidin-1-yl}sulfonyl)benzonitrile;

5-(7-Methoxy-2,2-dimethyl-2,3-dihydro-1-benzofuran-4-yl)-4,4-dimethyl-2-[1-(quinolin-8-ylsulfonyl)piperidin-4-yl]-2,4-dihydro-3H-pyrazol-3-one;

5-(7-Methoxy-2,2-dimethyl-2,3-dihydro-1-benzofuran-4-yl)-4,4-dimethyl-2-[1-(naphthalen-2-ylsulfonyl)piperidin-4-yl]-2,4-dihydro-3H-pyrazol-3-one;

2-{1-[(2-Fluorophenyl)sulfonyl]piperidin-4-yl}-5-(7-methoxy-2,2-dimethyl-2,3-dihydro-1-benzofuran-4-yl)-4,4-dimethyl-2,4-dihydro-3H-pyrazol-3-one;

5-(7-Methoxy-2,2-dimethyl-2,3-dihydro-1-benzofuran-5-yl)-4,4-dimethyl-2-{1-[(3-methylphenyl)sulfonyl]piperidin-4-yl}-2,4-dihydro-3H-pyrazol-3-one;

5-(3,4-Dimethoxyphenyl)-4,4-dimethyl-2-[1-(pyridin-2-ylcarbonyl)piperidin-4-yl]-2,4-dihydro-3H-pyrazol-3-one;

5-(3,4-Dimethoxyphenyl)-2-{1-[(2-methoxypyridin-3-yl)carbonyl]piperidin-4-yl}-4,4-dimethyl-2,4-dihydro-3H-pyrazol-3-one;

2-{1-[(3,5-Difluoropyridin-2-yl)carbonyl]piperidin-4-yl}-5-(3,4-dimethoxyphenyl)-4,4-dimethyl-2,4-dihydro-3H-pyrazol-3-one;

5-(3,4-Dimethoxyphenyl)-4,4-dimethyl-2-{1-[(3-methylpyridin-2-yl)carbonyl]piperidin-4-yl}-2,4-dihydro-3H-pyrazol-3-one;

5-(3,4-Dimethoxyphenyl)-4,4-dimethyl-2-[1-(quinolin-3-ylcarbonyl)piperidin-4-yl]-2,4-dihydro-3H-pyrazol-3-one;

5-(3,4-Dimethoxyphenyl)-2-{1-[(2,6-dimethoxypyridin-3-yl)carbonyl]piperidin-4-yl}-4,4-dimethyl-2,4-dihydro-3H-pyrazol-3-one;

5-(3,4-Dimethoxyphenyl)-4,4-dimethyl-2-[1-(quinolin-2-ylcarbonyl)piperidin-4-yl]-2,4-dihydro-3H-pyrazol-3-one;

5-[3-(Cyclopropylmethoxy)-4-methoxyphenyl]-2-{1-[(2-methoxyphenyl)carbonyl]piperidin-4-yl}-4,4-dimethyl-2,4-dihydro-3H-pyrazol-3-one;

5-(3,4-Dimethoxyphenyl)-4,4-dimethyl-2-[1-(1,8-naphthyridin-2-ylcarbonyl)piperidin-4-yl]-2,4-dihydro-3H-pyrazol-3-one;

2-[1-(3-Chloroisonicotinoyl)piperidin-4-yl]-5-(3,4-dimethoxyphenyl)-4,4-dimethyl-2,4-dihydro-3H-pyrazol-3-one;

5-(3,4-Dimethoxyphenyl)-4,4-dimethyl-2-(1-{[4-(trifluoromethyl)pyridin-3-yl]carbonyl}piperidin-4-yl)-2,4-dihydro-3H-pyrazol-3-one;

5-(3,4-Dimethoxyphenyl)-4,4-dimethyl-2-[1-(1,6-naphthyridin-5-ylcarbonyl)piperidin-4-yl]-2,4-dihydro-3H-pyrazol-3-one;

5-(3,4-Dimethoxyphenyl)-4,4-dimethyl-2-[1-(quinoxalin-2-ylcarbonyl)piperidin-4-yl]-2,4-dihydro-3H-pyrazol-3-one;

5-(3,4-Dimethoxyphenyl)-2-[1-(isoquinolin-1-ylcarbonyl)piperidin-4-yl]-4,4-dimethyl-2,4-dihydro-3H-pyrazol-3-one;

2-{1-[3-(Cyclopropylmethoxy)-4-(difluoromethoxy)benzoyl]piperidin-4-yl}-5-(3,4-dimethoxyphenyl)-4,4-dimethyl-2,4-dihydro-3H-pyrazol-3-one;

5-(3,4-Dimethoxyphenyl)-4,4-dimethyl-2-[1-(quinolin-8-ylcarbonyl)piperidin-4-yl]-2,4-dihydro-3H-pyrazol-3-one;

5-(3,4-Dimethoxyphenyl)-4,4-dimethyl-2-[1-(2-piperidin-1-ylisonicotinoyl)piperidin-4-yl]-2,4-dihydro-3H-pyrazol-3-one;

5-(3,4-Dimethoxyphenyl)-4,4-dimethyl-2-[1-(quinolin-4-ylcarbonyl)piperidin-4-yl]-2,4-dihydro-3H-pyrazol-3-one;

5-(3,4-Dimethoxyphenyl)-4,4-dimethyl-2-[1-(2-morpholin-4-ylisonicotinoyl)piperidin-4-yl]-2,4-dihydro-3H-pyrazol-3-one;

5-(3,4-Dimethoxyphenyl)-2-[1-(isoquinolin-5-ylcarbonyl)piperidin-4-yl]-4,4-dimethyl-2,4-dihydro-3H-pyrazol-3-one;

5-(3,4-Dimethoxyphenyl)-4,4-dimethyl-2-[1-(quinolin-5-ylcarbonyl)piperidin-4-yl]-2,4-dihydro-3H-pyrazol-3-one;
5-(3,4-Dimethoxyphenyl)-4,4-dimethyl-2-[1-(quinolin-7-ylcarbonyl)piperidin-4-yl]-2,4-dihydro-3H-pyrazol-3-one;
5-(3,4-Dimethoxyphenyl)-4,4-dimethyl-2-[1-(quinolin-6-ylcarbonyl)piperidin-4-yl]-2,4-dihydro-3H-pyrazol-3-one;
5-(3,4-Dimethoxyphenyl)-2-[1-(isoquinolin-4-ylcarbonyl)piperidin-4-yl]-4,4-dimethyl-2,4-dihydro-3H-pyrazol-3-one;
5-(3,4-Dimethoxyphenyl)-2-[1-(1H-indol-5-ylcarbonyl)piperidin-4-yl]-4,4-dimethyl-2,4-dihydro-3H-pyrazol-3-one;
5-(3,4-Dimethoxyphenyl)-2-[1-(1H-indol-6-ylcarbonyl)piperidin-4-yl]-4,4-dimethyl-2,4-dihydro-3H-pyrazol-3-one;
5-(3,4-Dimethoxyphenyl)-2-[1-(1H-indol-4-ylcarbonyl)piperidin-4-yl]-4,4-dimethyl-2,4-dihydro-3H-pyrazol-3-one;
5-(3,4-Dimethoxyphenyl)-2-[1-(1H-indol-7-ylcarbonyl)piperidin-4-yl]-4,4-dimethyl-2,4-dihydro-3H-pyrazol-3-one;
5-(3,4-Dimethoxyphenyl)-2-[1-(1H-indol-2-ylcarbonyl)piperidin-4-yl]-4,4-dimethyl-2,4-dihydro-3H-pyrazol-3-one;
5-(3,4-Dimethoxyphenyl)-4,4-dimethyl-2-{1-[(2,4,6-trichlorophenyl)carbonyl]piperidin-4-yl}-2,4-dihydro-3H-pyrazol-3-one;
5-(3,4-Dimethoxyphenyl)-4,4-dimethyl-2-[1-(phenylcarbonyl)piperidin-4-yl]-2,4-dihydro-3H-pyrazol-3-one;
5-(3,4-Dimethoxyphenyl)-2-{1-[(2,4-dimethoxyphenyl)carbonyl]piperidin-4-yl}-4,4-dimethyl-2,4-dihydro-3H-pyrazol-3-one;
5-(3,4-Dimethoxyphenyl)-2-{1-[(3-methoxyphenyl)carbonyl]piperidin-4-yl}-4,4-dimethyl-2,4-dihydro-3H-pyrazol-3-one;
5-(3,4-Dimethoxyphenyl)-2-{1-[(3-fluorophenyl)carbonyl]piperidin-4-yl}-4,4-dimethyl-2,4-dihydro-3H-pyrazol-3-one;
5-(3,4-Dimethoxyphenyl)-2-{1-[(4-methoxyphenyl)carbonyl]piperidin-4-yl}-4,4-dimethyl-2,4-dihydro-3H-pyrazol-3-one;
5-(3,4-Dimethoxyphenyl)-4,4-dimethyl-2-[1-(naphthalen-1-ylcarbonyl)piperidin-4-yl]-2,4-dihydro-3H-pyrazol-3-one;
2-{1-[(3-Chlorophenyl)carbonyl]piperidin-4-yl}-5-(3,4-dimethoxyphenyl)-4,4-dimethyl-2,4-dihydro-3H-pyrazol-3-one;
5-(3,4-Dimethoxyphenyl)-2-{1-[(3-ethoxyphenyl)carbonyl]piperidin-4-yl}-4,4-dimethyl-2,4-dihydro-3H-pyrazol-3-one;
2-{1-[(4-Bromophenyl)carbonyl]piperidin-4-yl}-5-(3,4-dimethoxyphenyl)-4,4-dimethyl-2,4-dihydro-3H-pyrazol-3-one;
2-{1-[(2-Bromophenyl)carbonyl]piperidin-4-yl}-5-(3,4-dimethoxyphenyl)-4,4-dimethyl-2,4-dihydro-3H-pyrazol-3-one;
2-(1-{[4-Amino-3-(trifluoromethyl)phenyl]carbonyl}piperidin-4-yl)-5-(3,4-dimethoxyphenyl)-4,4-dimethyl-2,4-dihydro-3H-pyrazol-3-one;
4-({4-[3-(3,4-Dimethoxyphenyl)-4,4-dimethyl-5-oxo-4,5-dihydro-1H-pyrazol-1-yl]piperidin-1-yl}carbonyl)phenyl acetate;
5-(7-Methoxy-2,2-dimethyl-2,3-dihydro-1-benzofuran-4-yl)-2-{1-[(2-methoxyphenyl)carbonyl]piperidin-4-yl}-4,4-dimethyl-2,4-dihydro-3H-pyrazol-3-one;
5-(3,4-Dimethoxyphenyl)-2-{1-[(3-hydroxyphenyl)carbonyl]piperidin-4-yl}-4,4-dimethyl-2,4-dihydro-3H-pyrazol-3-one;
2-({4-[3-(7-Methoxy-2,2-dimethyl-2,3-dihydro-1-benzofuran-4-yl)-4,4-dimethyl-5-oxo-4,5-dihydro-1H-pyrazol-1-yl]piperidin-1-yl}carbonyl)phenyl acetate;
2-[1-(2-Hydroxybenzoyl)piperidin-4-yl]-5-(7-methoxy-2,2-dimethyl-2,3-dihydro-1-benzofuran-4-yl)-4,4-dimethyl-2,4-dihydro-3H-pyrazol-3-one;
2-(1-{[5-(Benzyloxy)-2-chlorophenyl]carbonyl}piperidin-4-yl)-5-(3,4-dimethoxyphenyl)-4,4-dimethyl-2,4-dihydro-3H-pyrazol-3-one;
2-(1-{[2-Chloro-5-(propan-2-yloxy)phenyl]carbonyl}piperidin-4-yl)-5-(3,4-dimethoxyphenyl)-4,4-dimethyl-2,4-dihydro-3H-pyrazol-3-one;
5-(3,4-dimethoxyphenyl)-4,4-dimethyl-2-(1-{[3-(propan-2-yloxy)phenyl]carbonyl}piperidin-4-yl)-2,4-dihydro-3H-pyrazol-3-one;
Ethyl [4-chloro-3-({4-[3-(3,4-dimethoxyphenyl)-4,4-dimethyl-5-oxo-4,5-dihydro-1H-pyrazol-1-yl]piperidin-1-yl}carbonyl)phenoxy]acetate;
2-(1-{[5-(Benzyloxy)-2-methylphenyl]carbonyl}piperidin-4-yl)-5-(3,4-dimethoxyphenyl)-4,4-dimethyl-2,4-dihydro-3H-pyrazol-3-one;
5-(3,4-Dimethoxyphenyl)-2-{1-[(5-hydroxy-2-methylphenyl)carbonyl]piperidin-4-yl}-4,4-dimethyl-2,4-dihydro-3H-pyrazol-3-one;
Ethyl [3-({4-[3-(3,4-dimethoxyphenyl)-4,4-dimethyl-5-oxo-4,5-dihydro-1H-pyrazol-1-yl]piperidin-1-yl}carbonyl)-4-methylphenoxy]acetate;
5-(3,4-Dimethoxyphenyl)-4,4-dimethyl-2-(1-{[2-methyl-5-(propan-2-yloxy)phenyl]carbonyl}piperidin-4-yl)-2,4-dihydro-3H-pyrazol-3-one;
2-(1-{[5-(Benzyloxy)-2-methylphenyl]carbonyl}piperidin-4-yl)-5-(7-methoxy-2,2-dimethyl-2,3-dihydro-1-benzofuran-5-yl)-4,4-dimethyl-2,4-dihydro-3H-pyrazol-3-one;
2-{1-[(5-Hydroxy-2-methylphenyl)carbonyl]piperidin-4-yl}-5-(7-methoxy-2,2-dimethyl-2,3-dihydro-1-benzofuran-5-yl)-4,4-dimethyl-2,4-dihydro-3H-pyrazol-3-one;
5-(3,4-Dimethoxyphenyl)-2-{1-[(2-fluoro-5-hydroxyphenyl)carbonyl]piperidin-4-yl}-4,4-dimethyl-2,4-dihydro-3H-pyrazol-3-one;
2-{1-[(5-Amino-2-chlorophenyl)carbonyl]piperidin-4-yl}-5-(3,4-dimethoxyphenyl)-4,4-dimethyl-2,4-dihydro-3H-pyrazol-3-one;
N-[4-chloro-3-({4-[3-(3,4-dimethoxyphenyl)-4,4-dimethyl-5-oxo-4,5-dihydro-1H-pyrazol-1-yl]piperidin-1-yl}carbonyl)phenyl]acetamide;
2-({4-[3-(3,4-Dimethoxyphenyl)-4,4-dimethyl-5-oxo-4,5-dihydro-1H-pyrazol-1-yl]piperidin-1-yl}carbonyl)phenyl acetate;
5-(3,4-Dimethoxyphenyl)-2-{1-[(2-hydroxyphenyl)carbonyl]piperidin-4-yl}-4,4-dimethyl-2,4-dihydro-3H-pyrazol-3-one;
5-(3,4-Dimethoxyphenyl)-4,4-dimethyl-2-(1-{[3-(2,2,2-trifluoroethoxy)phenyl]-carbonyl}piperidin-4-yl)-2,4-dihydro-3H-pyrazol-3-one;
2-(1-{[2-(Cyclopentyloxy)phenyl]carbonyl}piperidin-4-yl)-5-(3,4-dimethoxyphenyl)-4,4-dimethyl-2,4-dihydro-3H-pyrazol-3-one;

2-[2-({4-[3-(3,4-Dimethoxyphenyl)-4,4-dimethyl-5-oxo-4,5-dihydro-1H-pyrazol-1-yl]piperidin-1-yl}carbonyl)phenoxy]acetamide;

and salts thereof.

12. A pharmaceutical composition comprising at least one of the compounds of formula 1 or a salt, a stereoisomer or a salt of a stereoisomer thereof according to claim 1 together with at least one pharmaceutically acceptable auxiliary.

13. A fixed combination comprising at least one compound of formula 1 or a salt, a stereoisomer or a salt of a stereoisomer thereof according to claim 1, at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, and at least one pharmaceutically acceptable auxiliary.

14. A non-fixed combination comprising at least one compound of formula 1 or a salt, a stereoisomer or a salt of a stereoisomer thereof according to claim 1, at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, and at least one pharmaceutically acceptable auxiliary.

15. A kit of parts comprising at least one compound of formula 1 or a salt, a stereoisomer or a salt of a stereoisomer thereof according to claim 1, at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 5 phosphodiesterase inhibitors, immunosuppressants, vitamin D analogues, HMG-CoA reductase-inhibitors, lung surfactants and antibiotics, and at least one pharmaceutically acceptable auxiliary.

* * * * *